United States Patent
Sano et al.

(10) Patent No.: US 11,504,920 B2
(45) Date of Patent: Nov. 22, 2022

(54) METHOD FOR MANUFACTURING CUFF FOR BLOOD PRESSURE MEASUREMENT DEVICE

(71) Applicants: OMRON Corporation, Kyoto (JP); OMRON HEALTHCARE Co., Ltd., Kyoto (JP)

(72) Inventors: Yoshihiko Sano, Kyoto (JP); Takayuki Matsuoka, Kyoto (JP); Minoru Taniguchi, Kyoto (JP); Yuichiro Arima, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 17/304,504

(22) Filed: Jun. 22, 2021

(65) Prior Publication Data
US 2021/0308954 A1 Oct. 7, 2021

Related U.S. Application Data

(63) Continuation of application No. PCT/JP2019/048031, filed on Dec. 9, 2019.

(30) Foreign Application Priority Data

Dec. 27, 2018 (JP) .............................. JP2018-246134

(51) Int. Cl.
*A61B 5/022* (2006.01)
*B29C 65/00* (2006.01)
*A44C 5/00* (2006.01)

(52) U.S. Cl.
CPC ............ *B29C 66/43* (2013.01); *A44C 5/0007* (2013.01); *A61B 5/022* (2013.01); *B29C 66/439* (2013.01);
(Continued)

(58) Field of Classification Search
CPC .... B29C 66/439; B29C 66/4326; A61B 5/022
(Continued)

(56) References Cited

U.S. PATENT DOCUMENTS 6,139,482 A * 10/2000 Lafleur .............. B65D 88/1612
493/217
9,155,477 B2 10/2015 Kim
(Continued)

FOREIGN PATENT DOCUMENTS

JP 2001-224558 A 8/2001
JP 2003-144398 A 5/2003
(Continued)

OTHER PUBLICATIONS

Translation of International Preliminary Report on Patentability and Written Opinion of the International Searching Authority dated Jul. 8, 2021 in International (PCT) Application No. PCT/JP2019/048031.

*Primary Examiner* — Scott W Dodds
(74) *Attorney, Agent, or Firm* — Wenderoth, Lind & Ponack, L.L.P.

(57) ABSTRACT

Provided is a method for manufacturing a cuff including a first outer layer, a first intermediate layer, a second intermediate layer, and a second outer layer, the method including disposing each of two non-bridge welded sheet members between the sheet member of the first intermediate layer bridge welded with the sheet member of the first outer layer and the sheet member of the first intermediate layer bridge welded with the sheet member of the second intermediate layer and between the sheet member of the second intermediate layer bridge welded with the sheet member of the first intermediate layer and the sheet member of the second intermediate layer bridge welded with the sheet member of
(Continued)

the second outer layer, and welding the four sheet members constituting the intermediate layers.

5 Claims, 44 Drawing Sheets

(52) U.S. Cl.
CPC ....... *B29C 66/8511* (2013.01); *A61B 2562/12* (2013.01)

(58) Field of Classification Search
USPC .................................................. 156/292, 182
See application file for complete search history.

(56) References Cited

U.S. PATENT DOCUMENTS

| | | | | |
|---|---|---|---|---|
| 2006/0135873 A1* | 6/2006 | Karo | .................. | A61B 5/02233 |
| | | | | 600/499 |
| 2018/0153418 A1* | 6/2018 | Sullivan | ............. | A61B 5/02233 |

FOREIGN PATENT DOCUMENTS

| | | |
|---|---|---|
| JP | 2006-174860 A | 7/2006 |
| WO | 2018/146968 A1 | 8/2018 |

* cited by examiner

[FIG. 1]
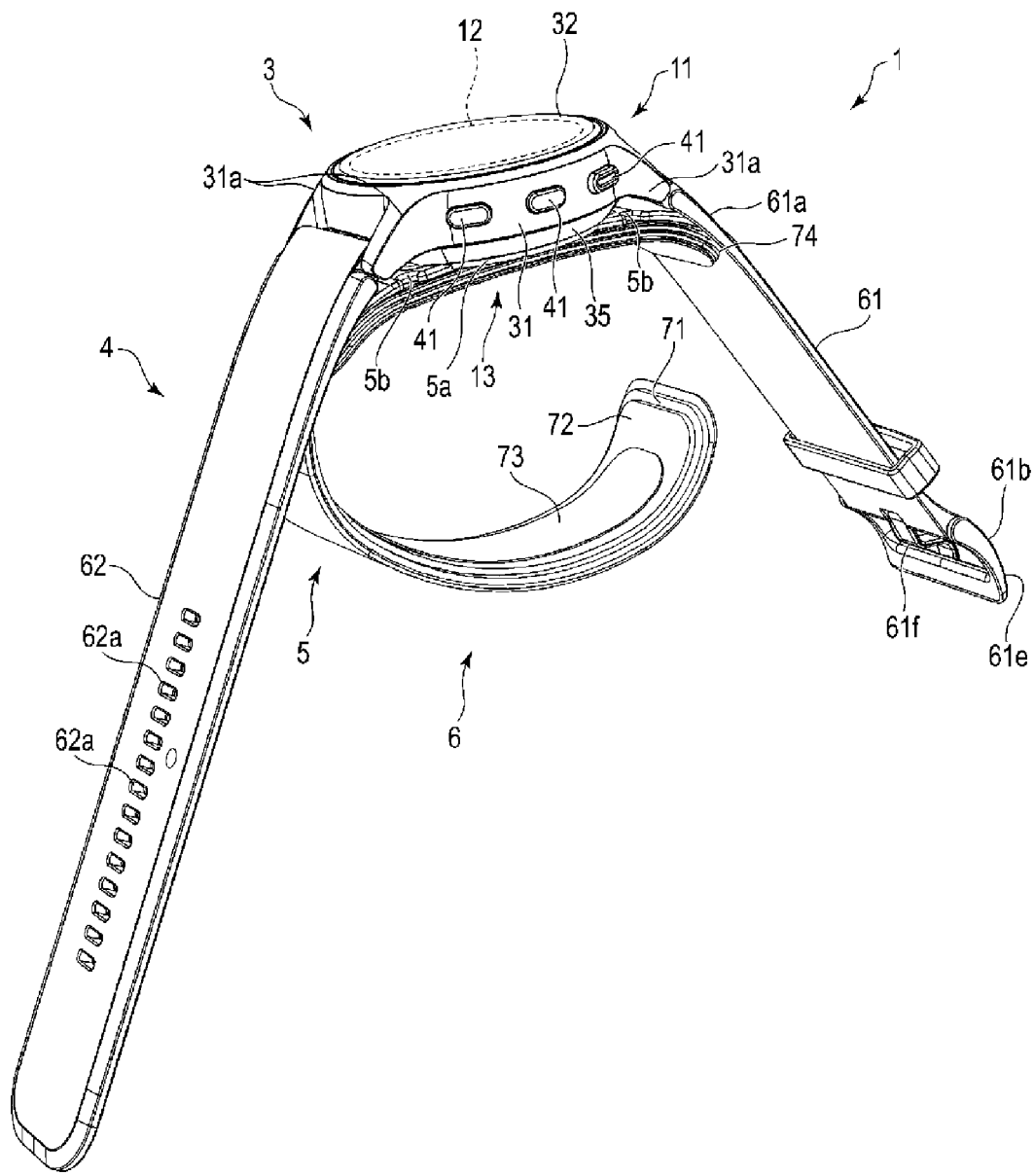

[FIG. 2]
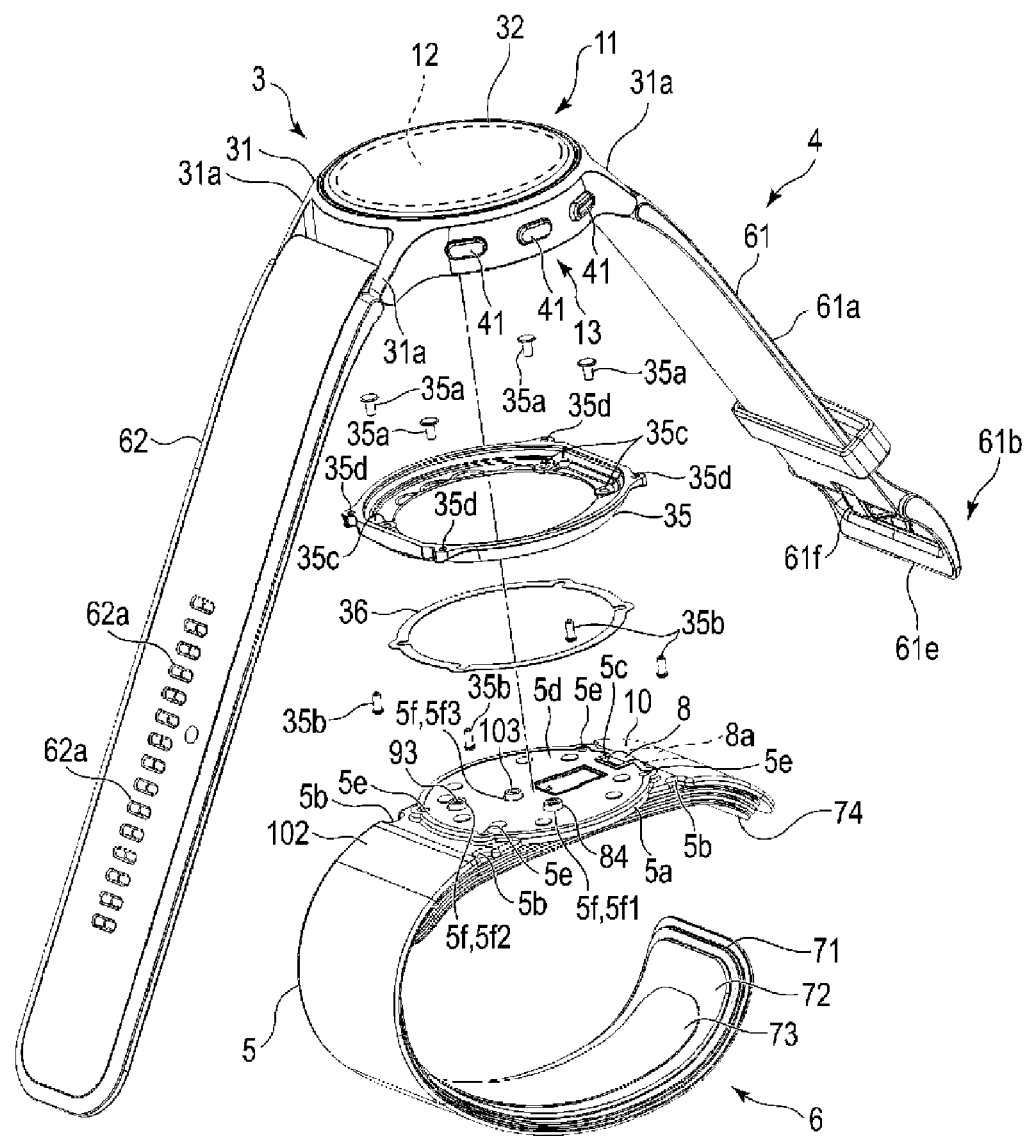

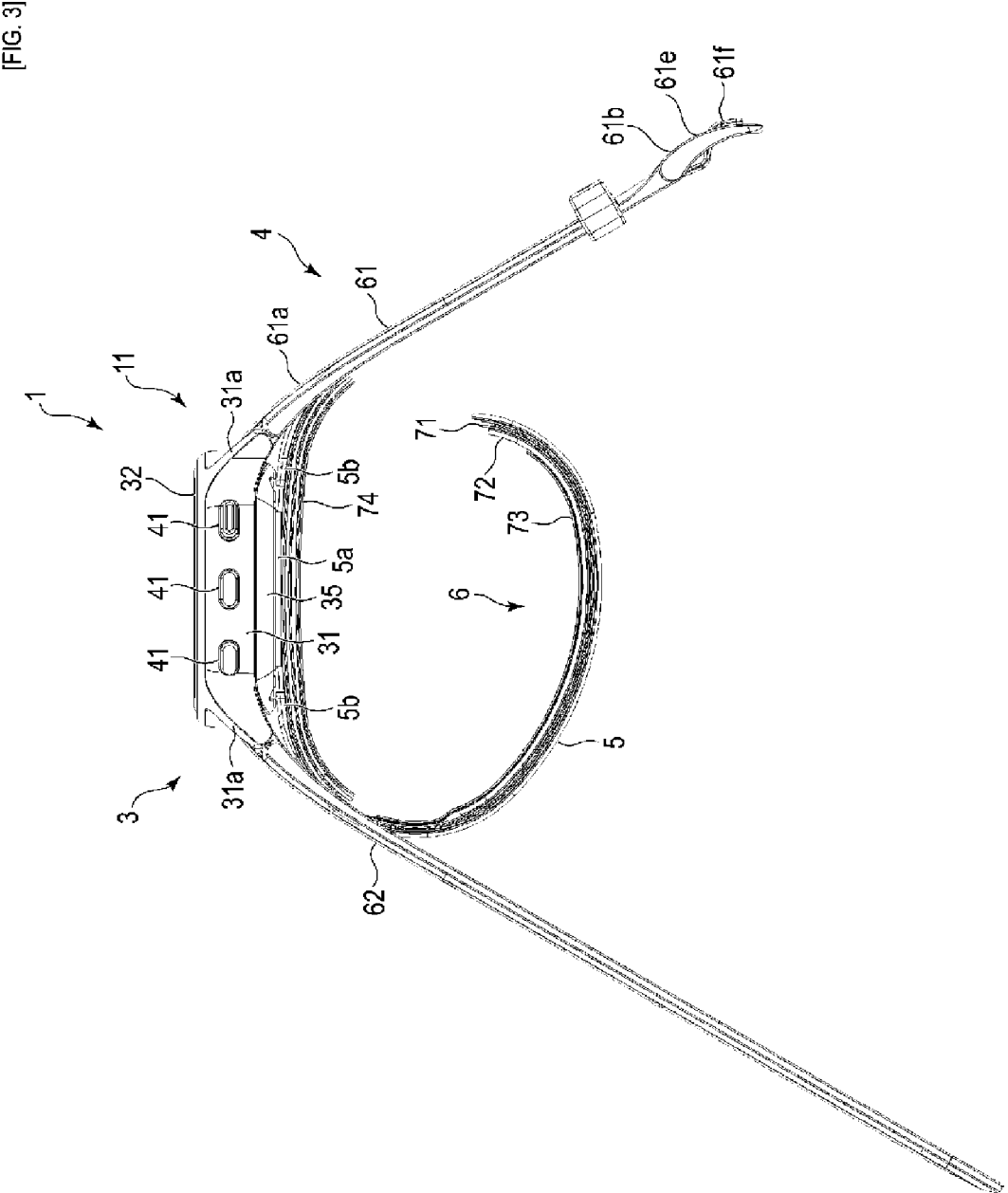

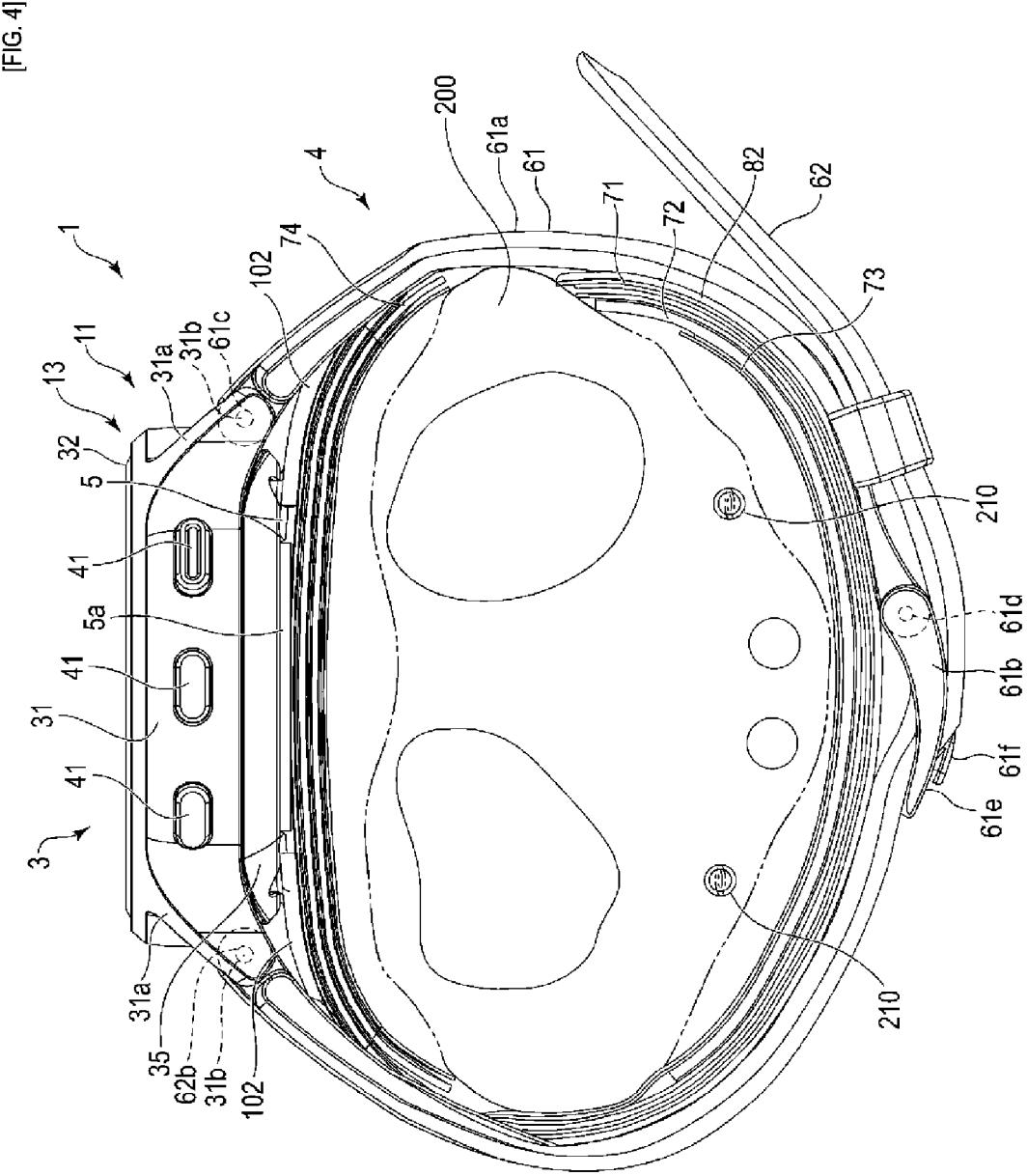
[FIG. 4]

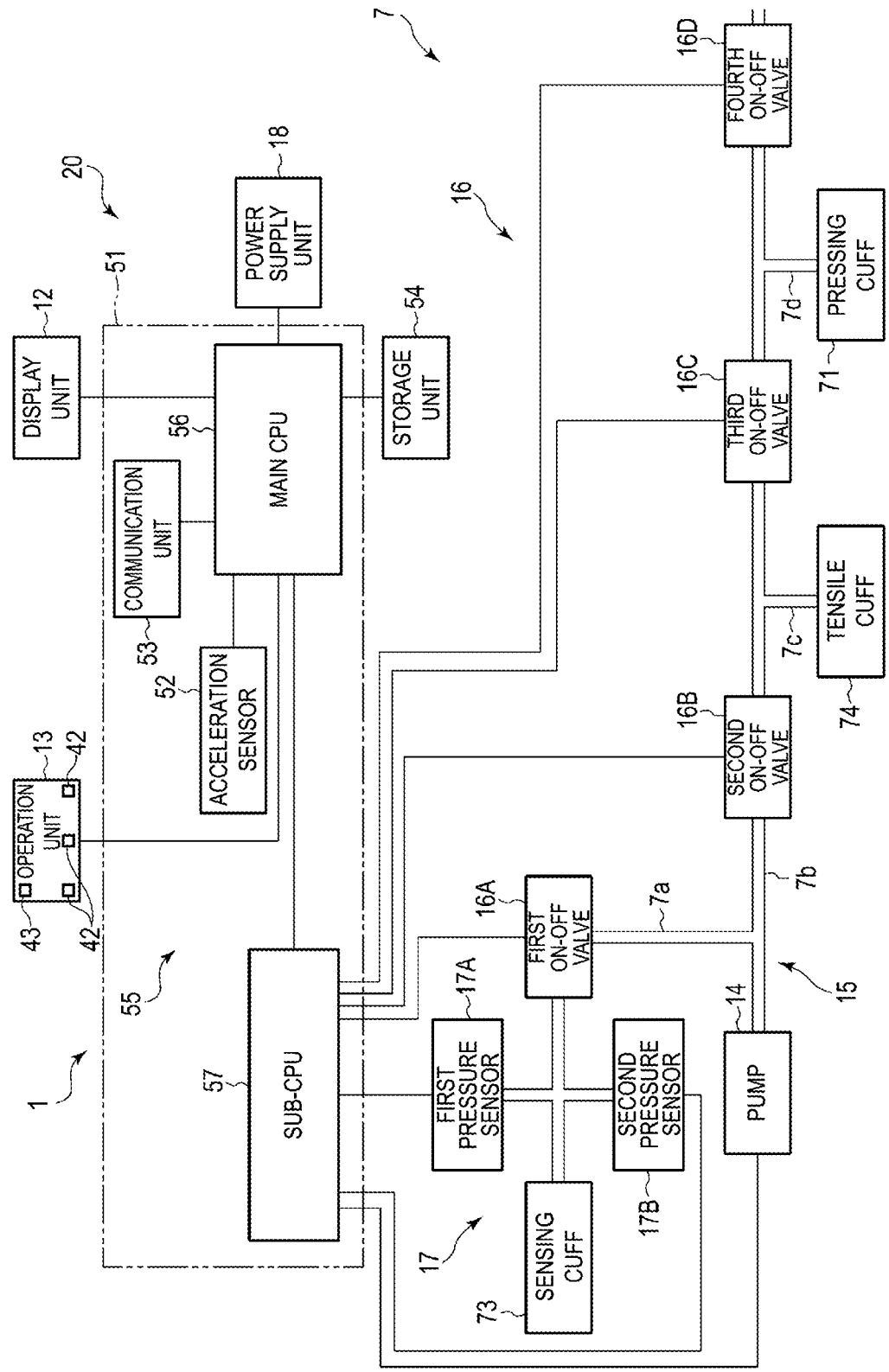
[FIG. 5]

[FIG. 6]
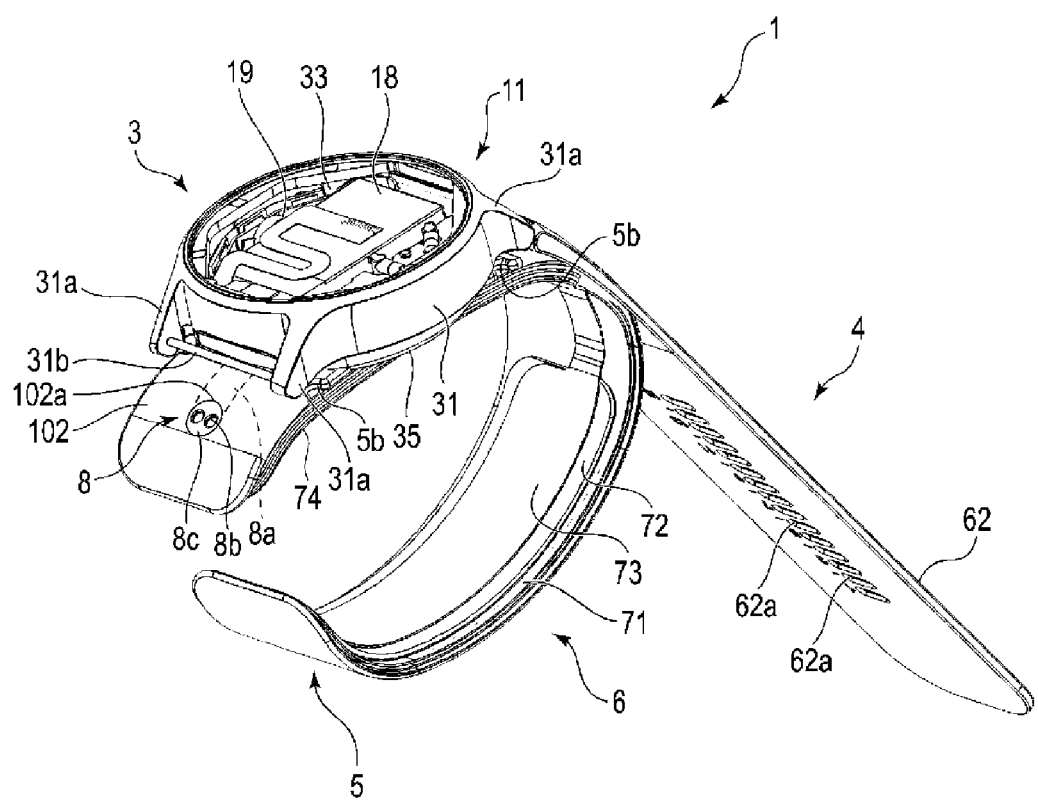

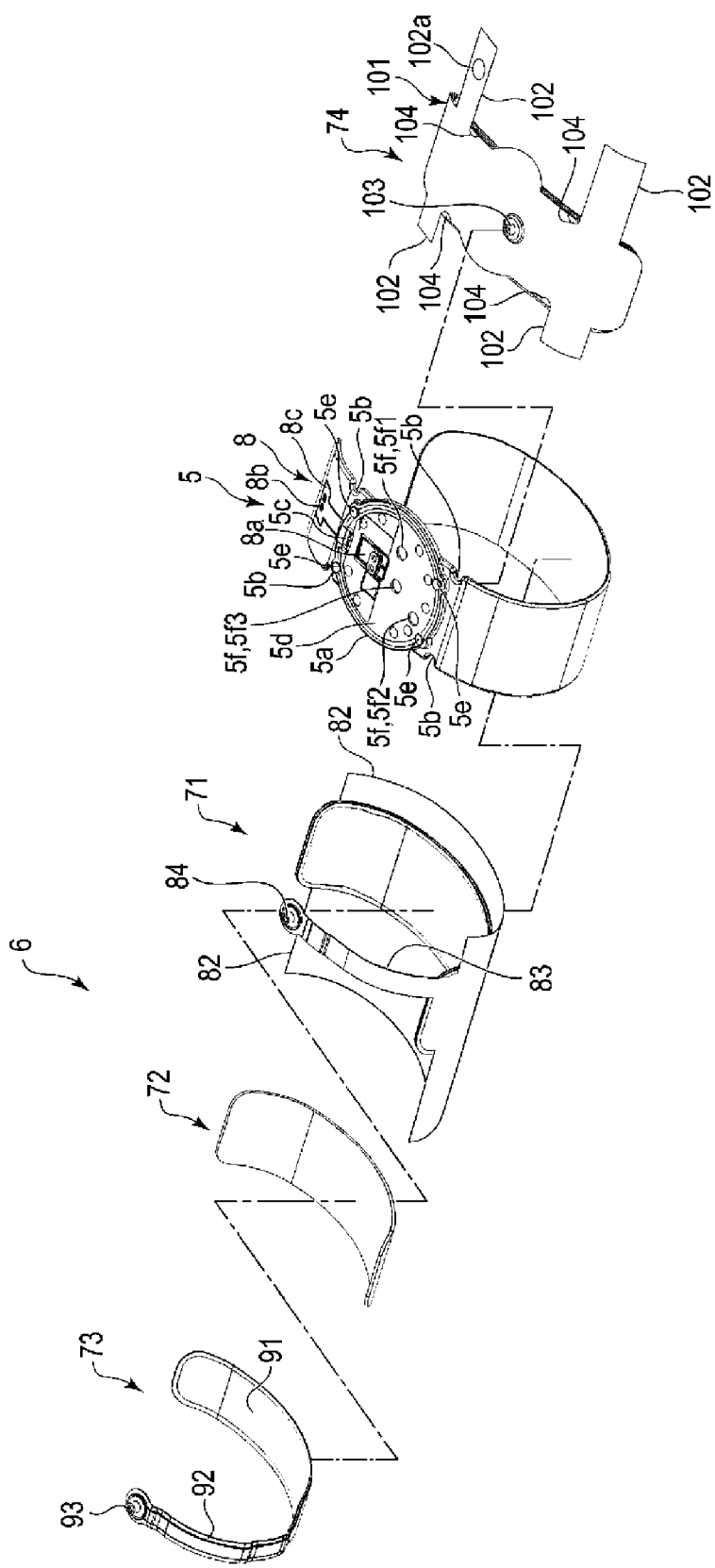
[FIG. 7]

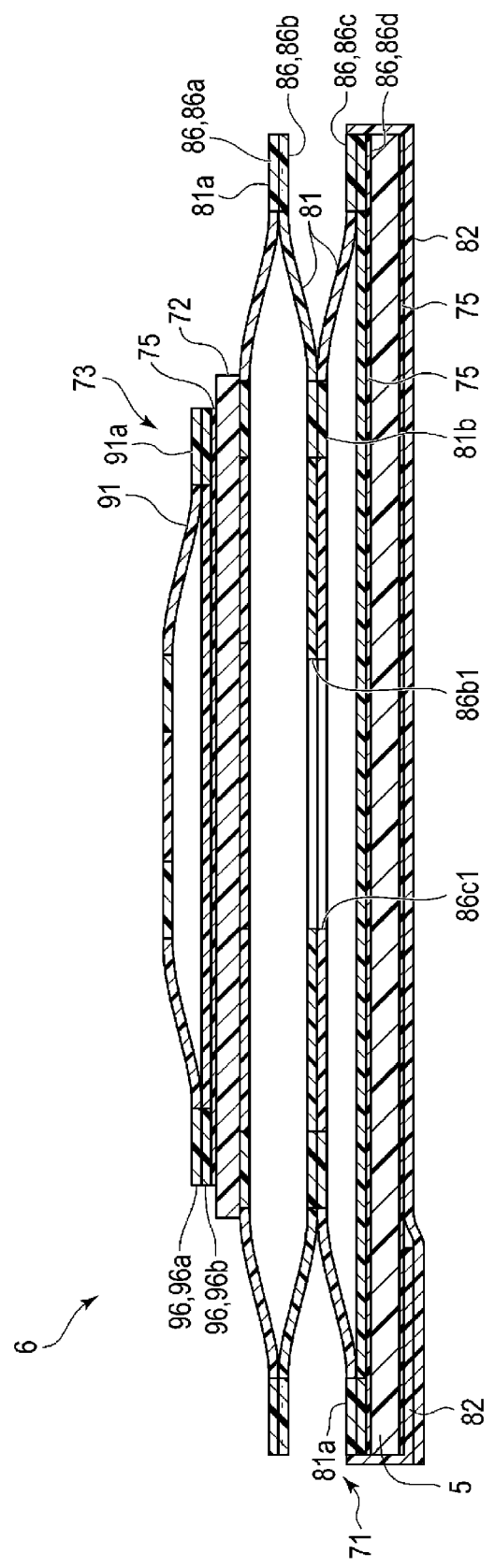
[FIG. 8]

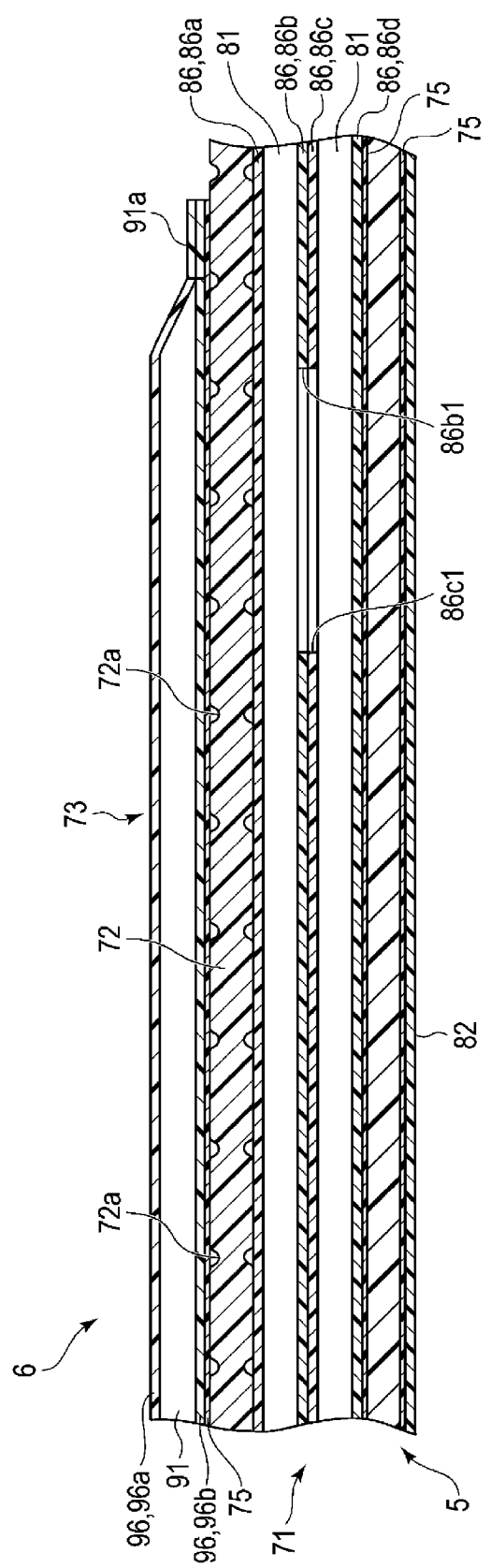
[FIG. 9]

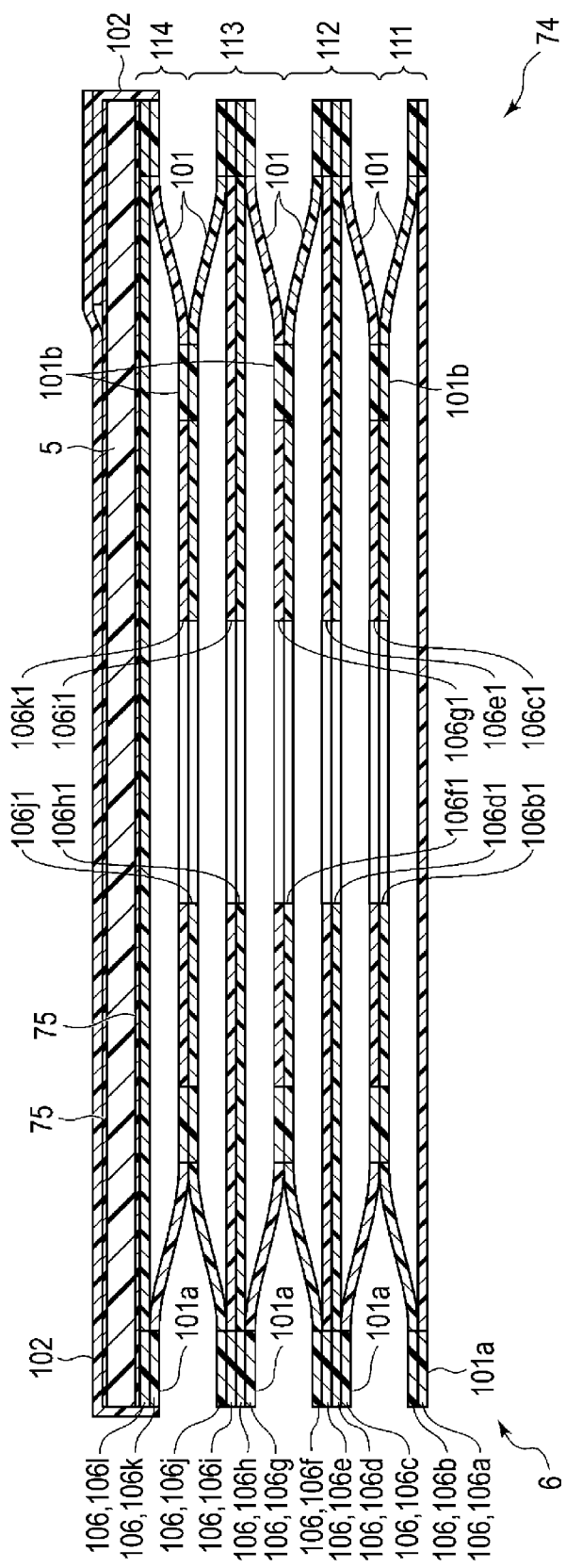
[FIG. 10]

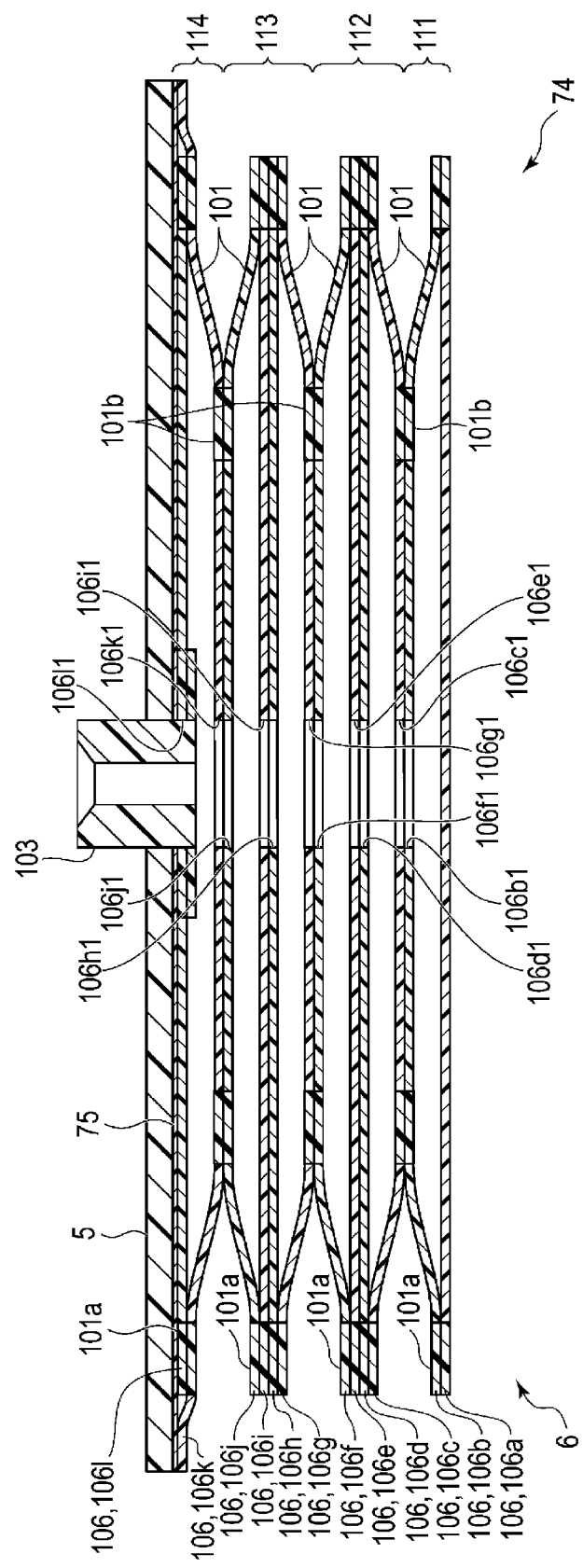
[FIG. 11]

[FIG. 12]
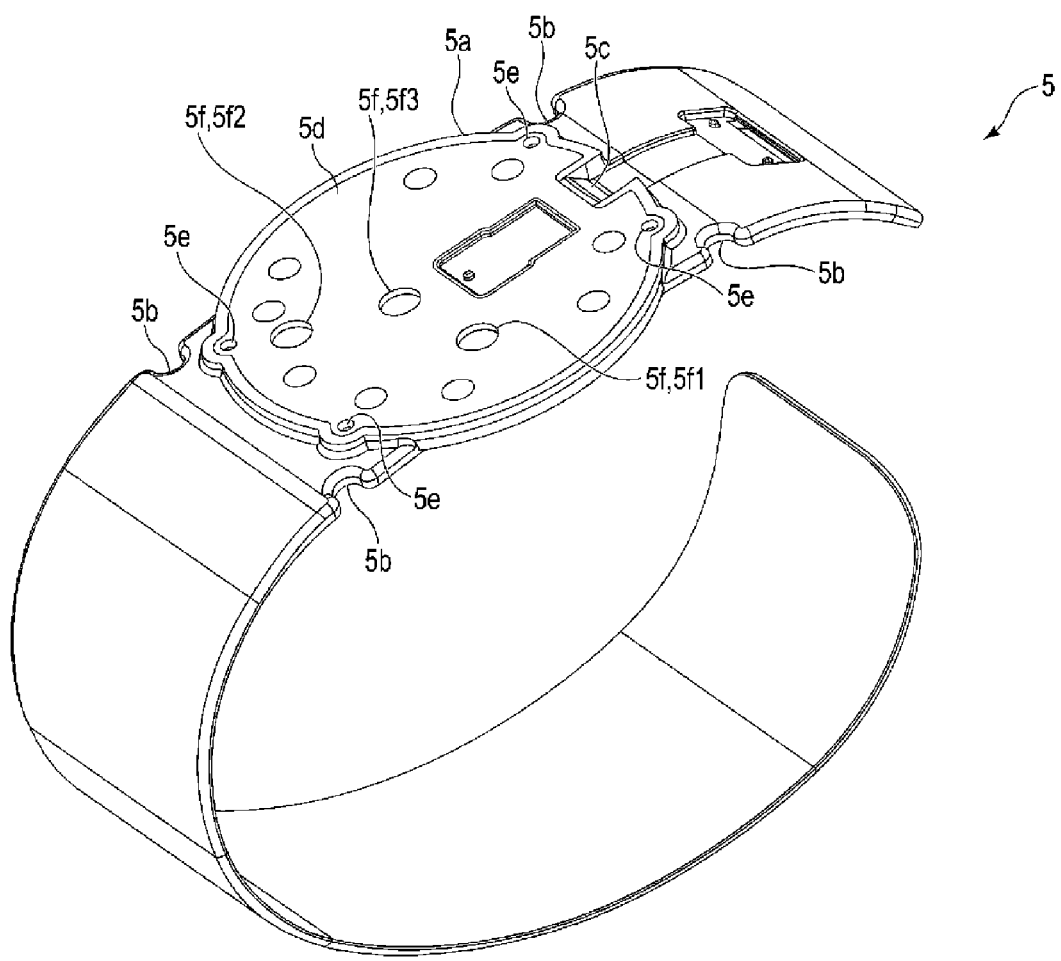

[FIG. 13]
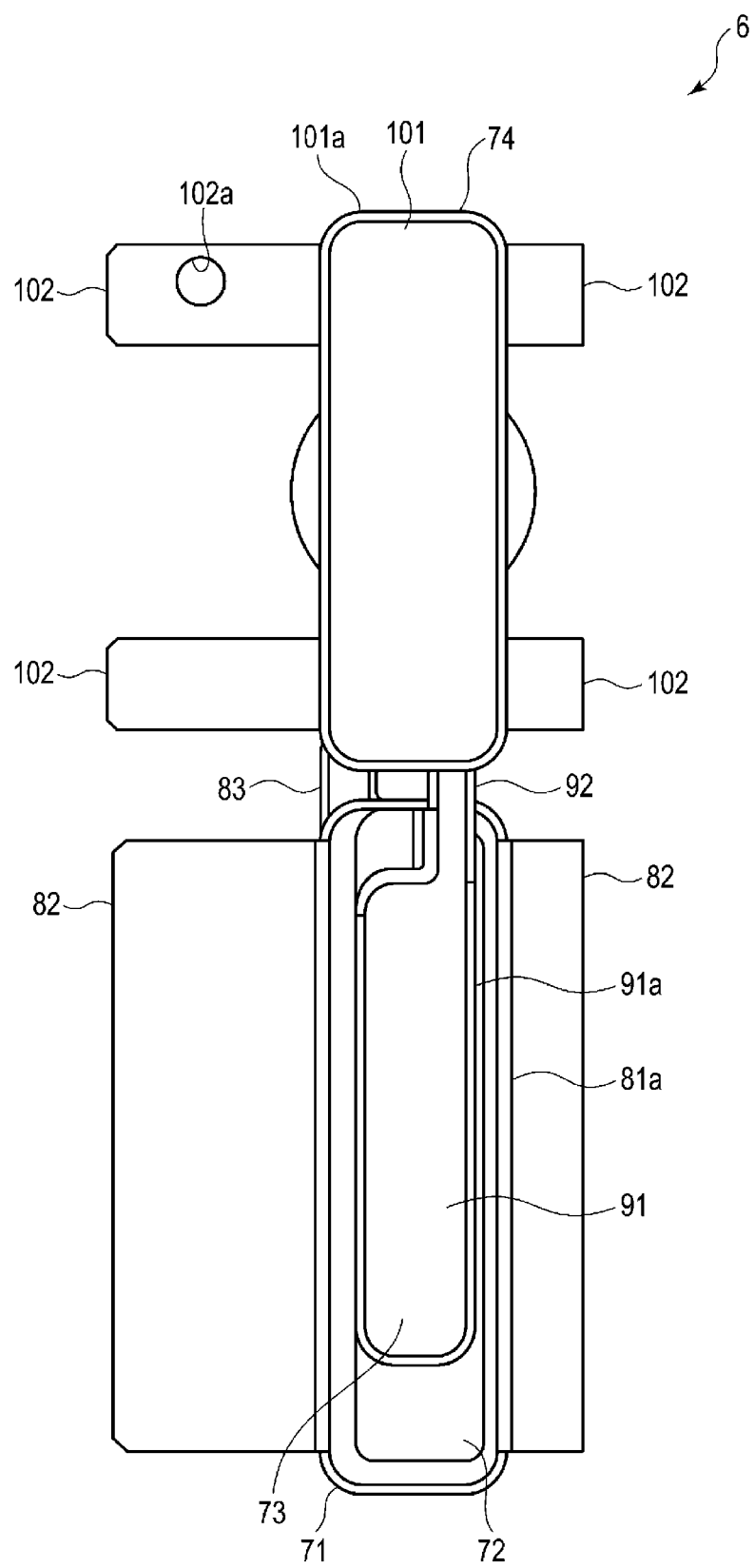

[FIG. 14]
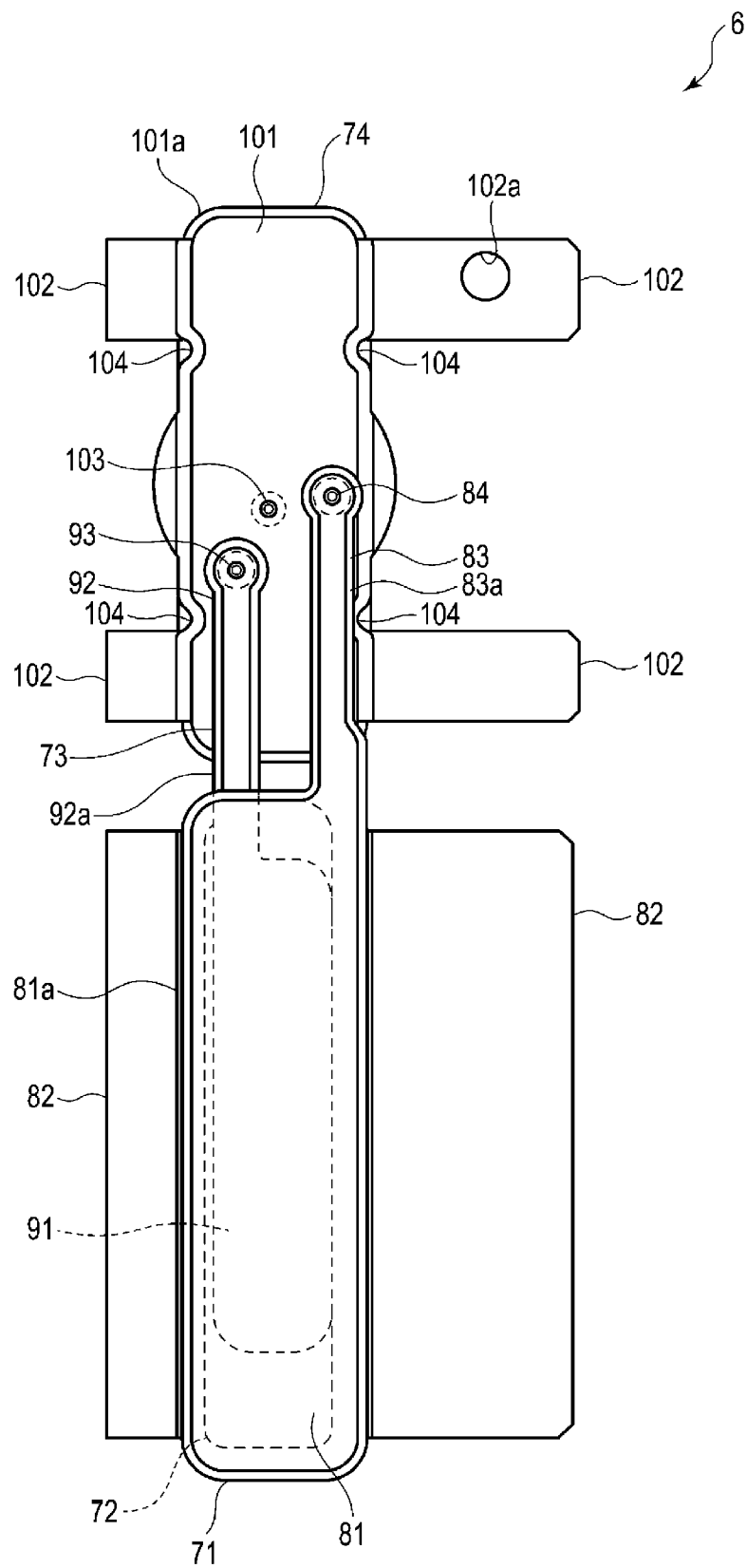

[FIG. 15]
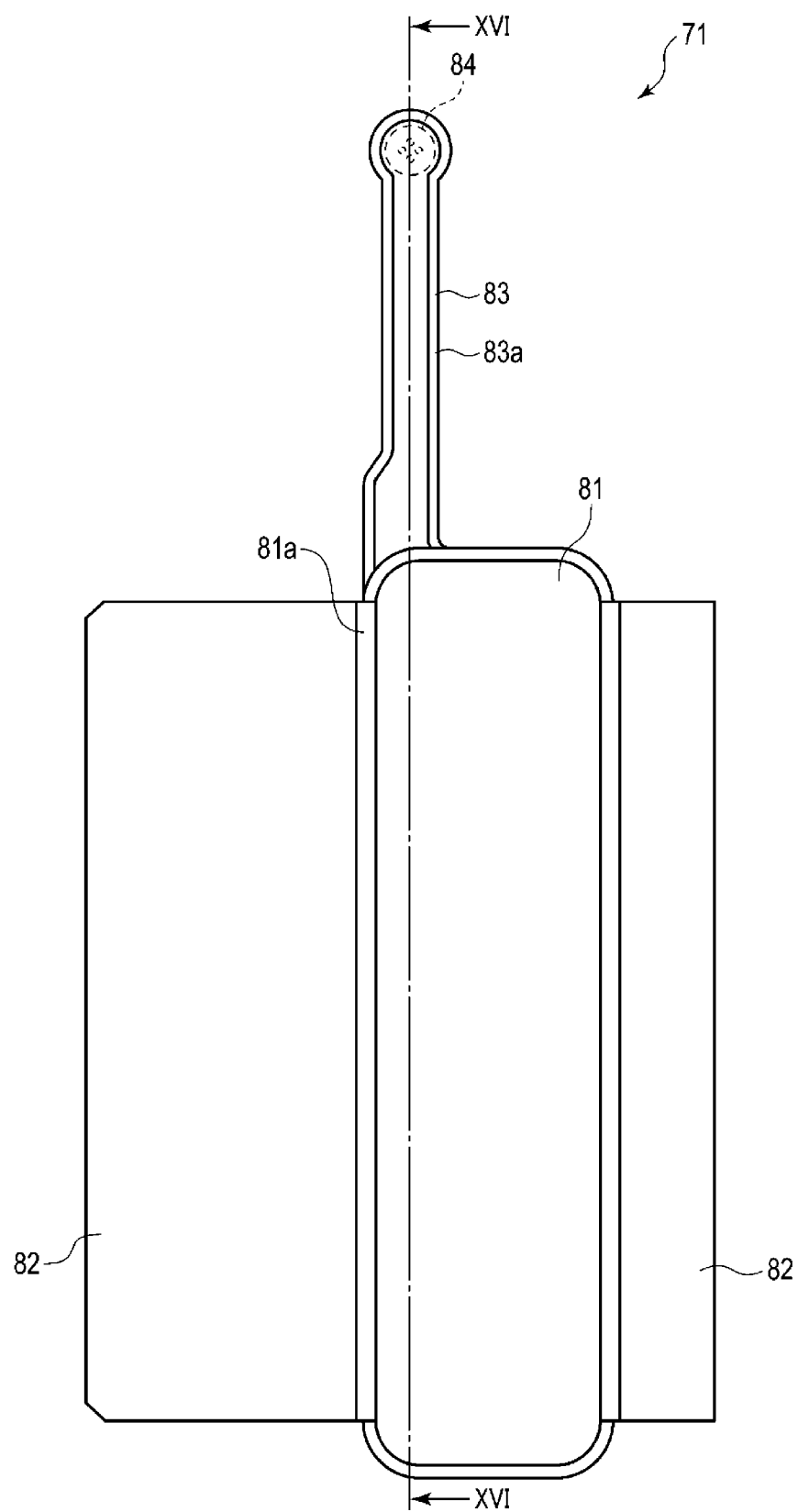

[FIG. 16]
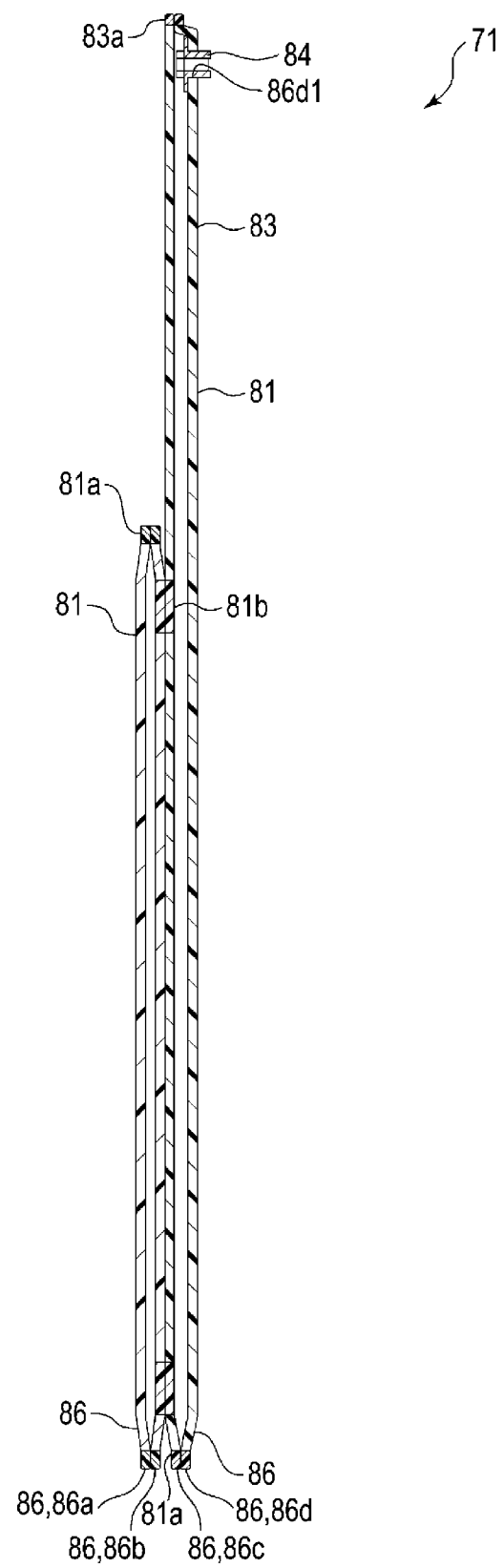

[FIG. 17]
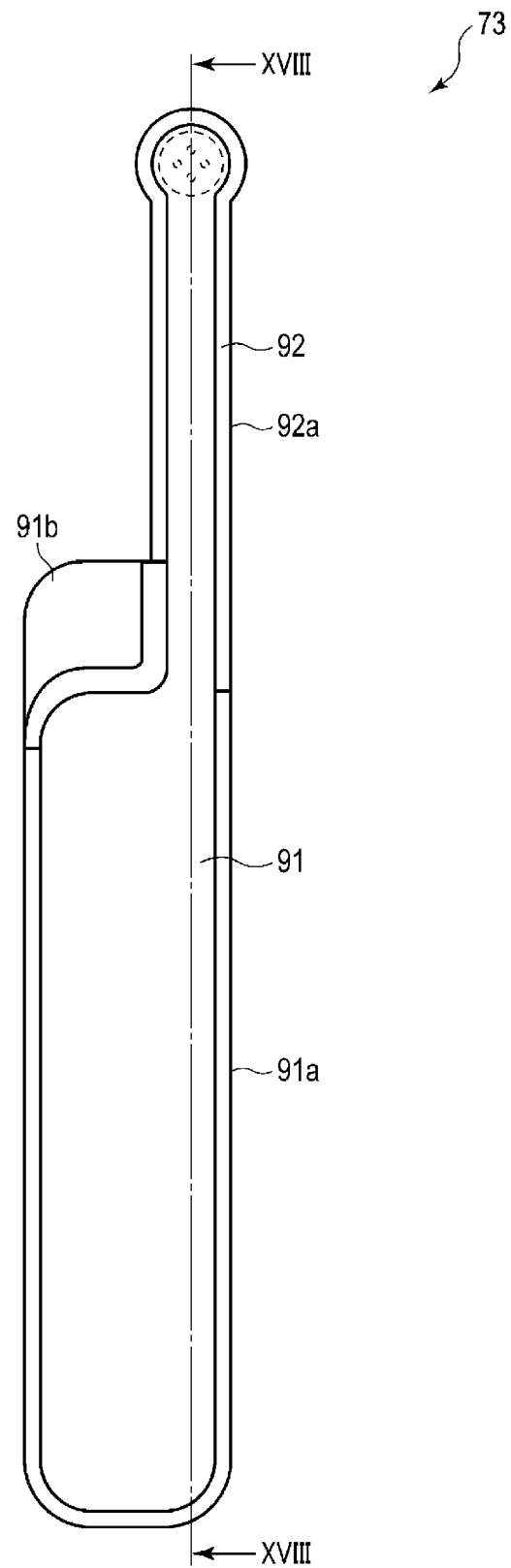

[FIG. 18]
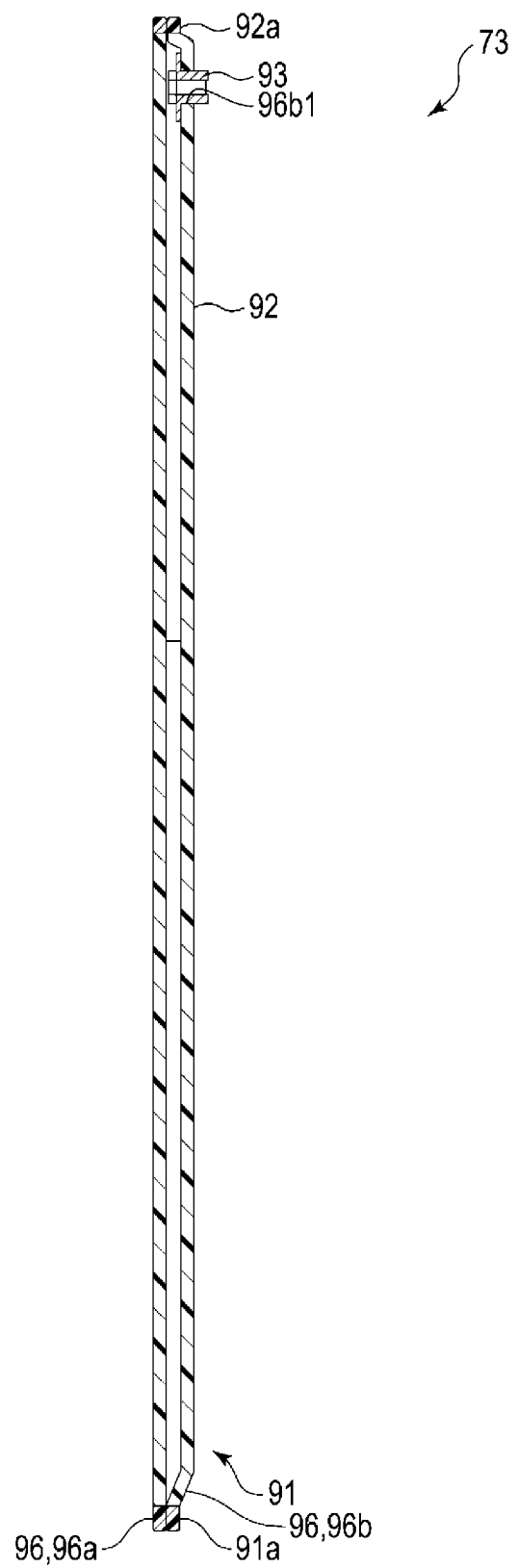

[FIG. 19]
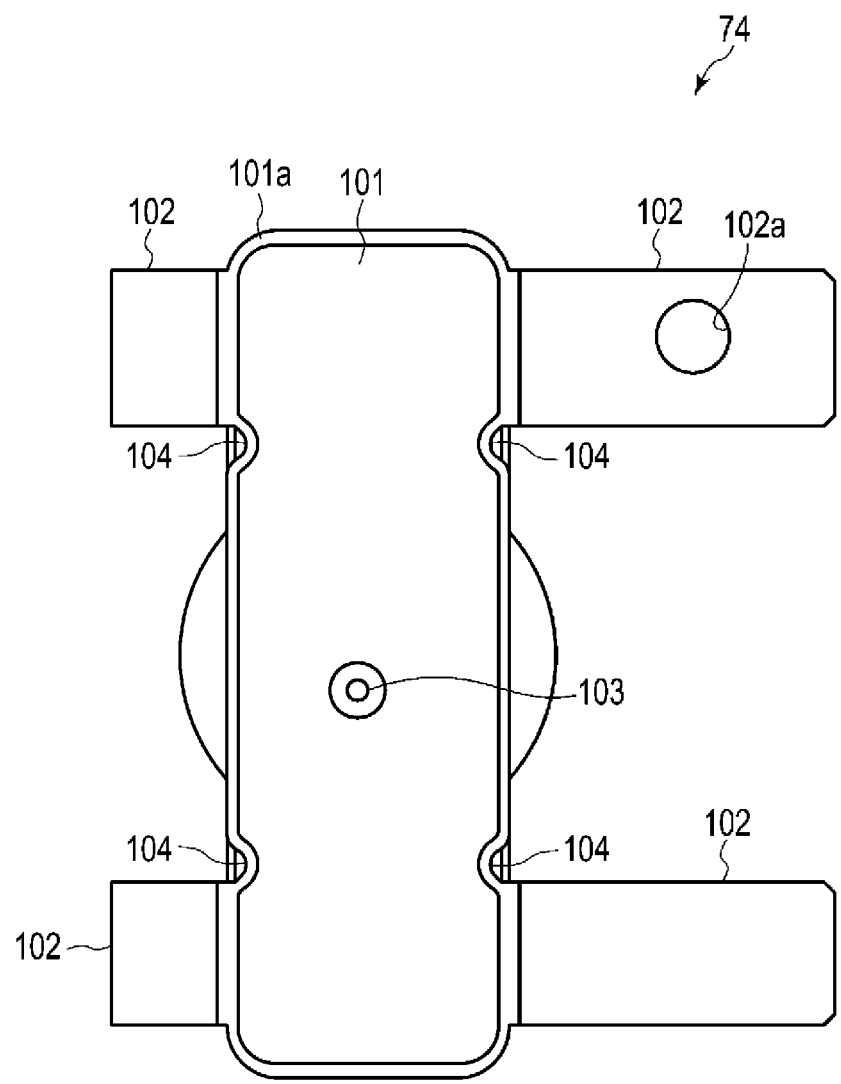

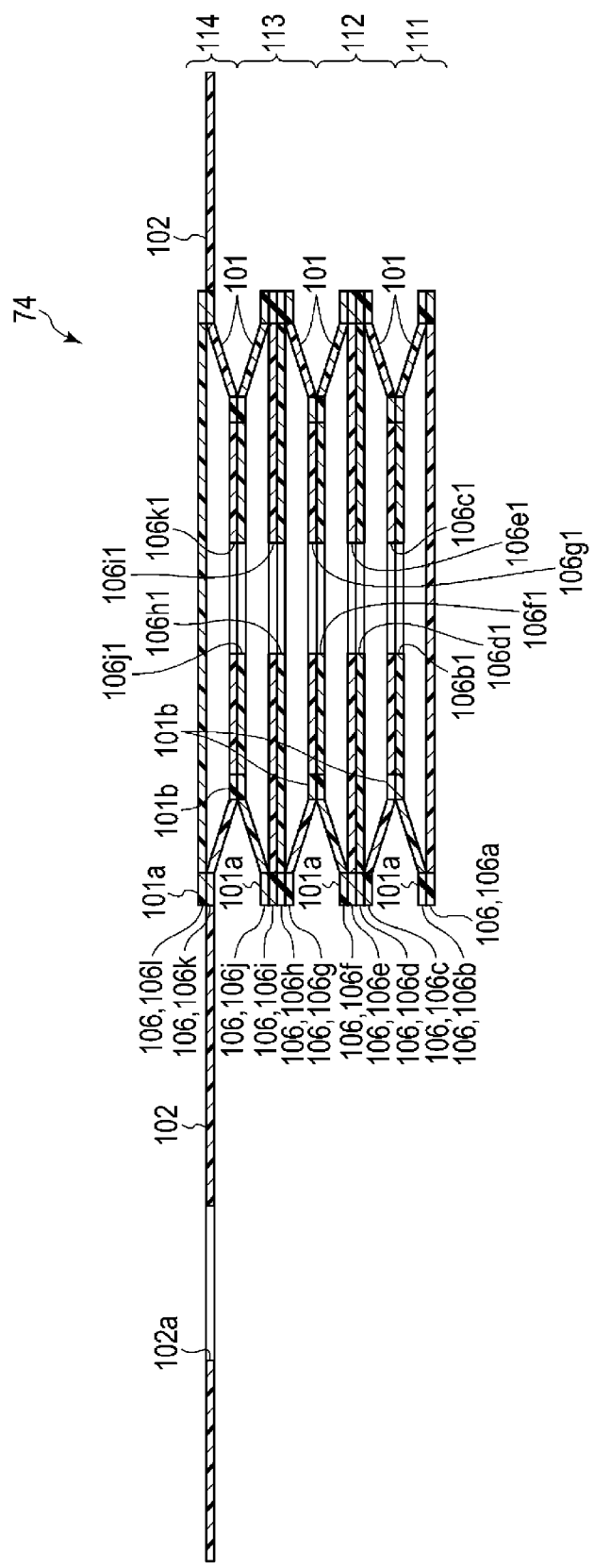

[FIG. 21]
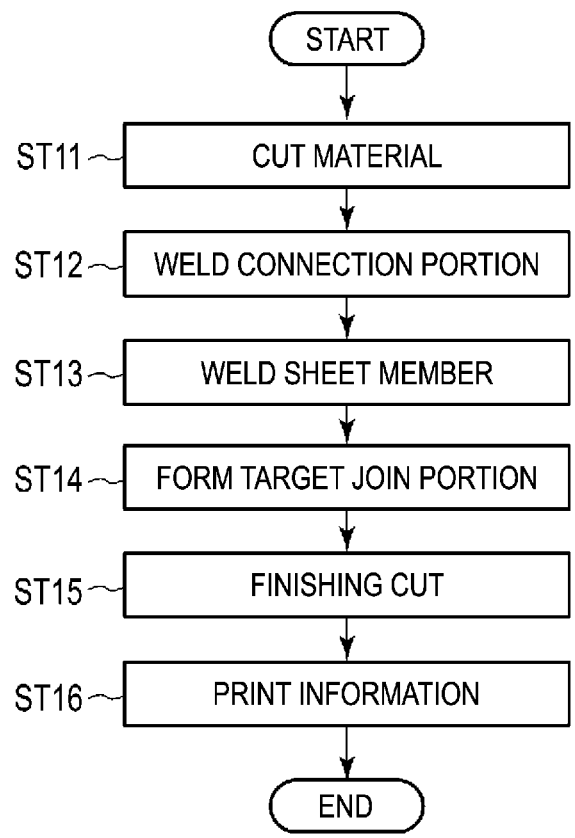

[FIG. 22]
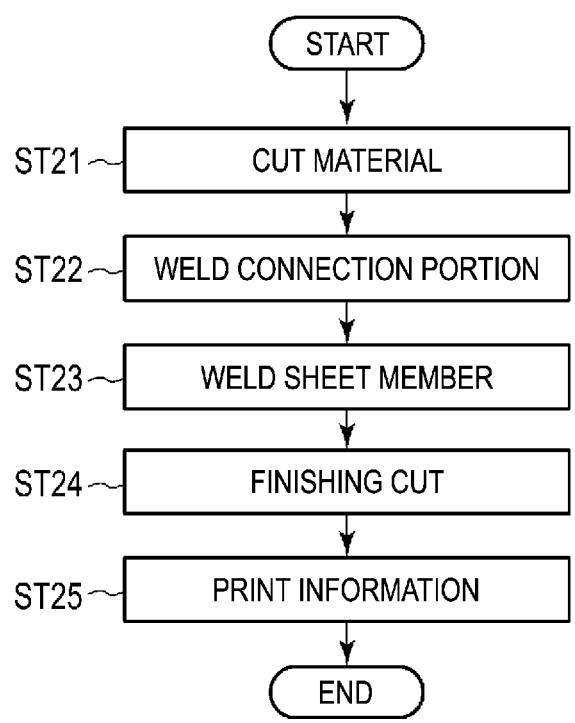

[FIG. 23]
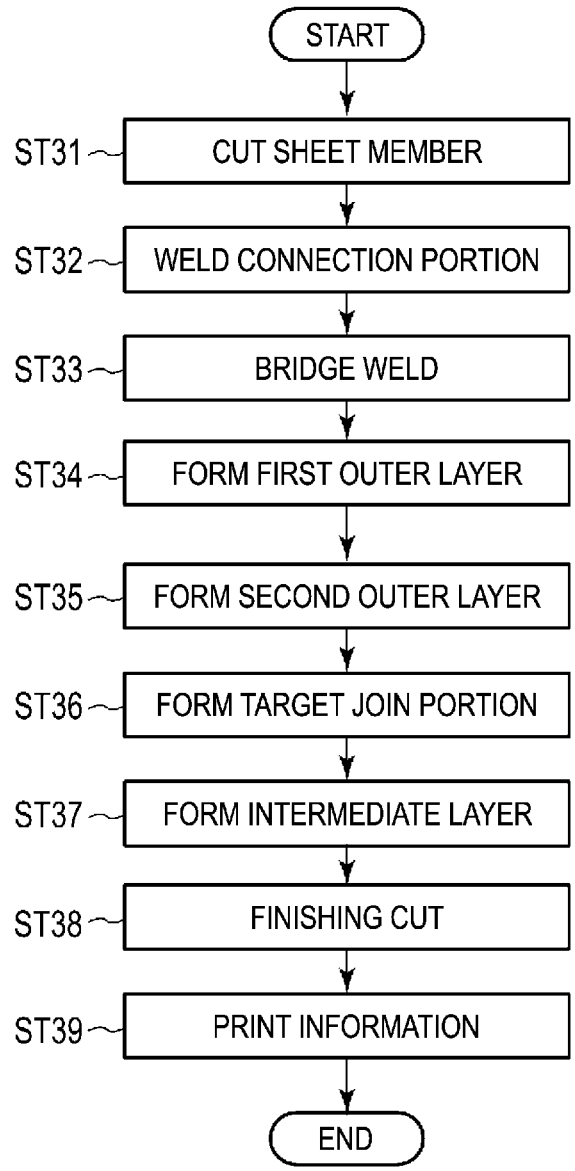

[FIG. 24]
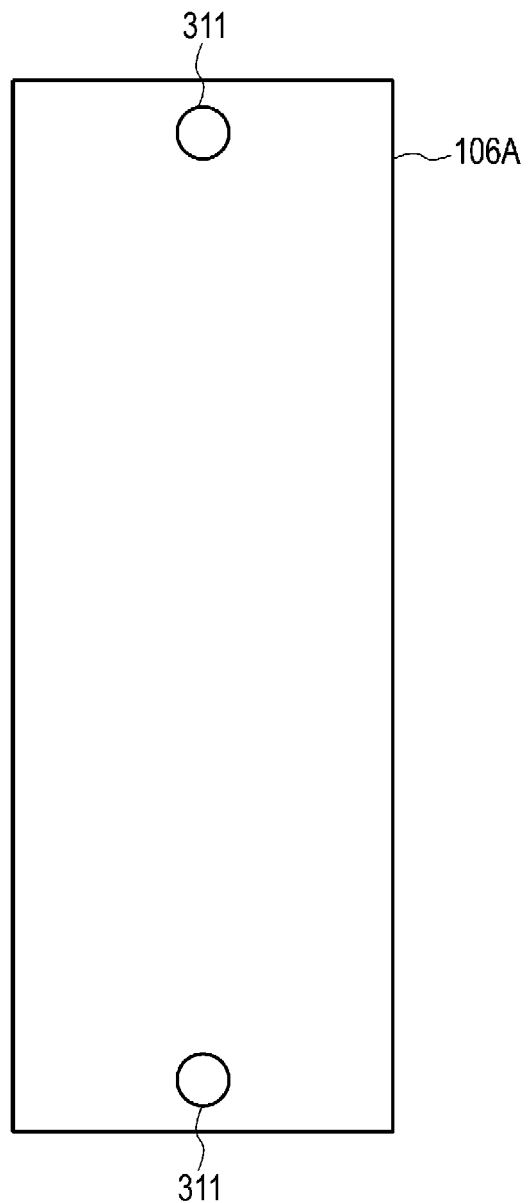

[FIG. 25]
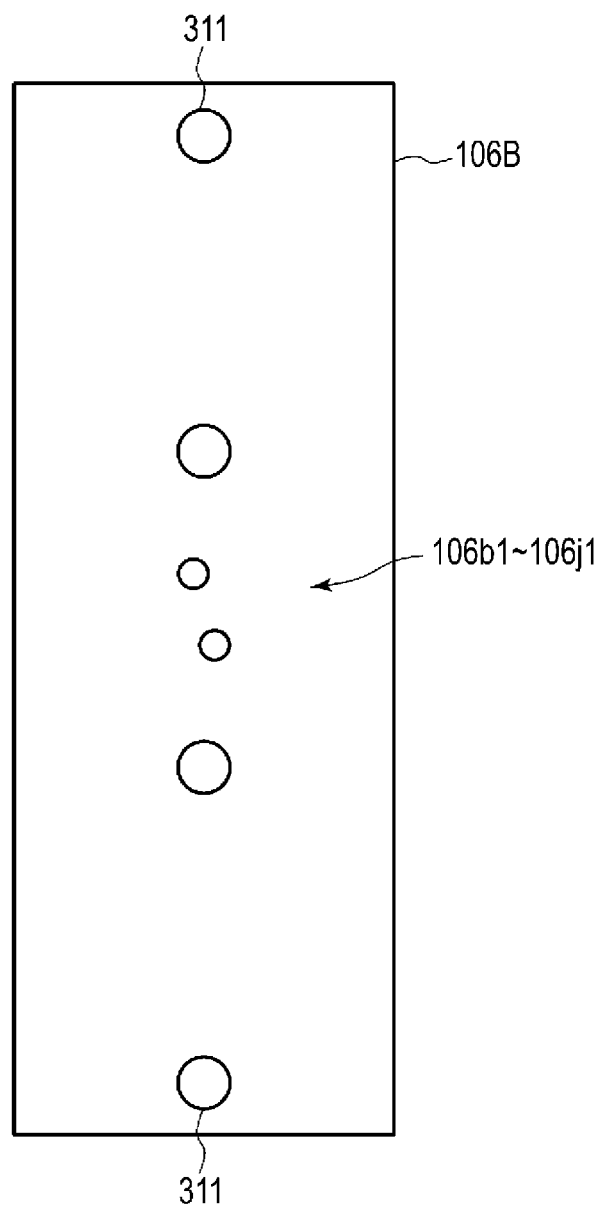

[FIG. 26]
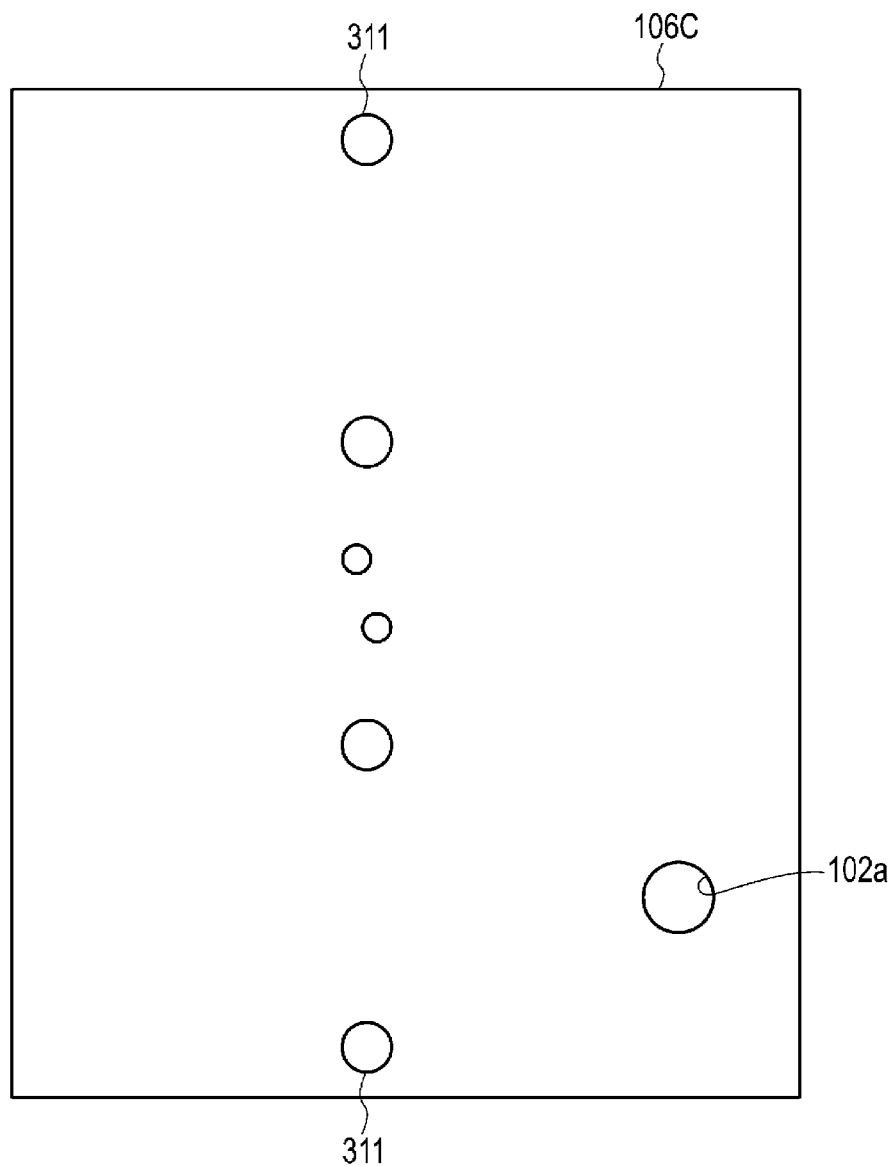

[FIG. 27]
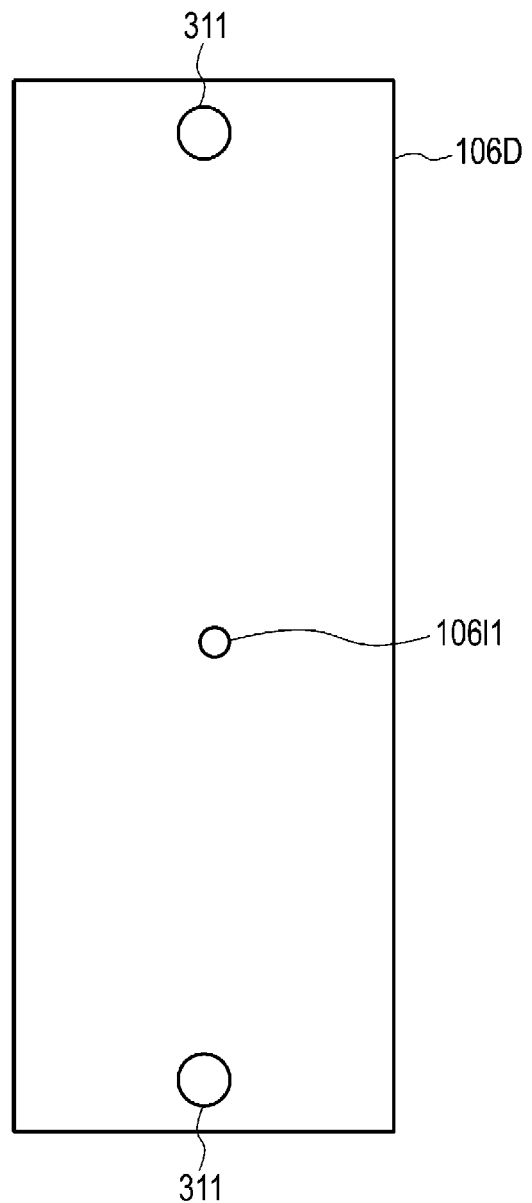

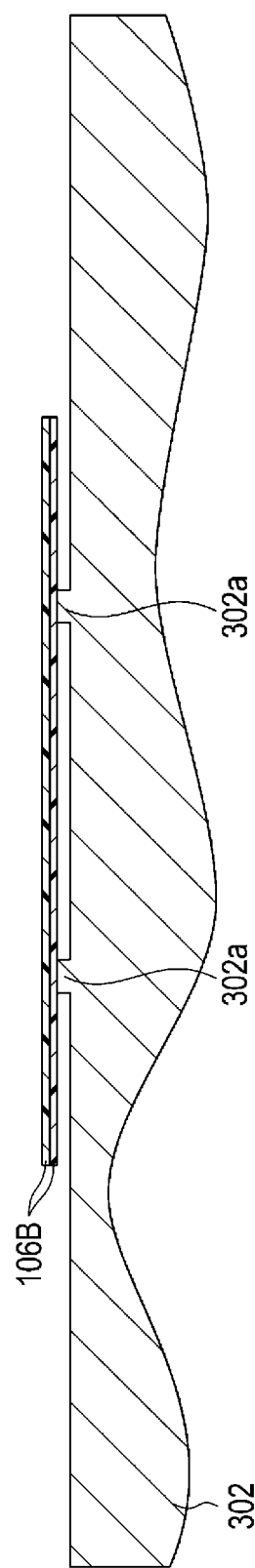
[FIG. 28]

[FIG. 29]
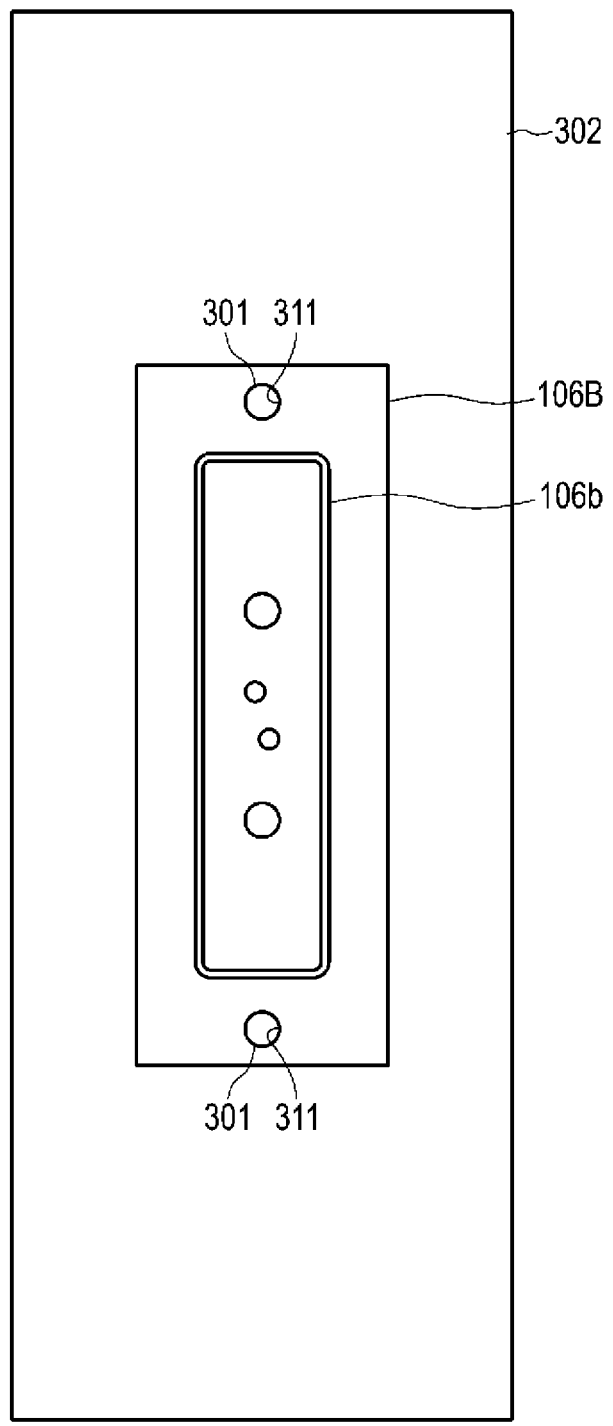

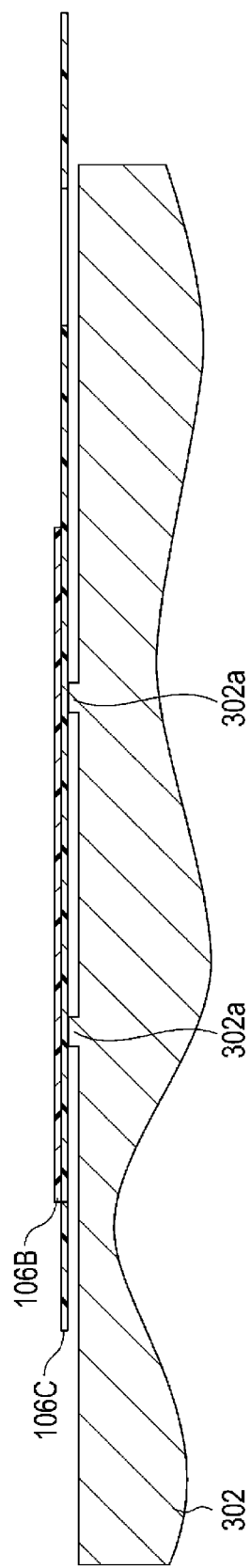
[FIG. 30]

[FIG. 31]
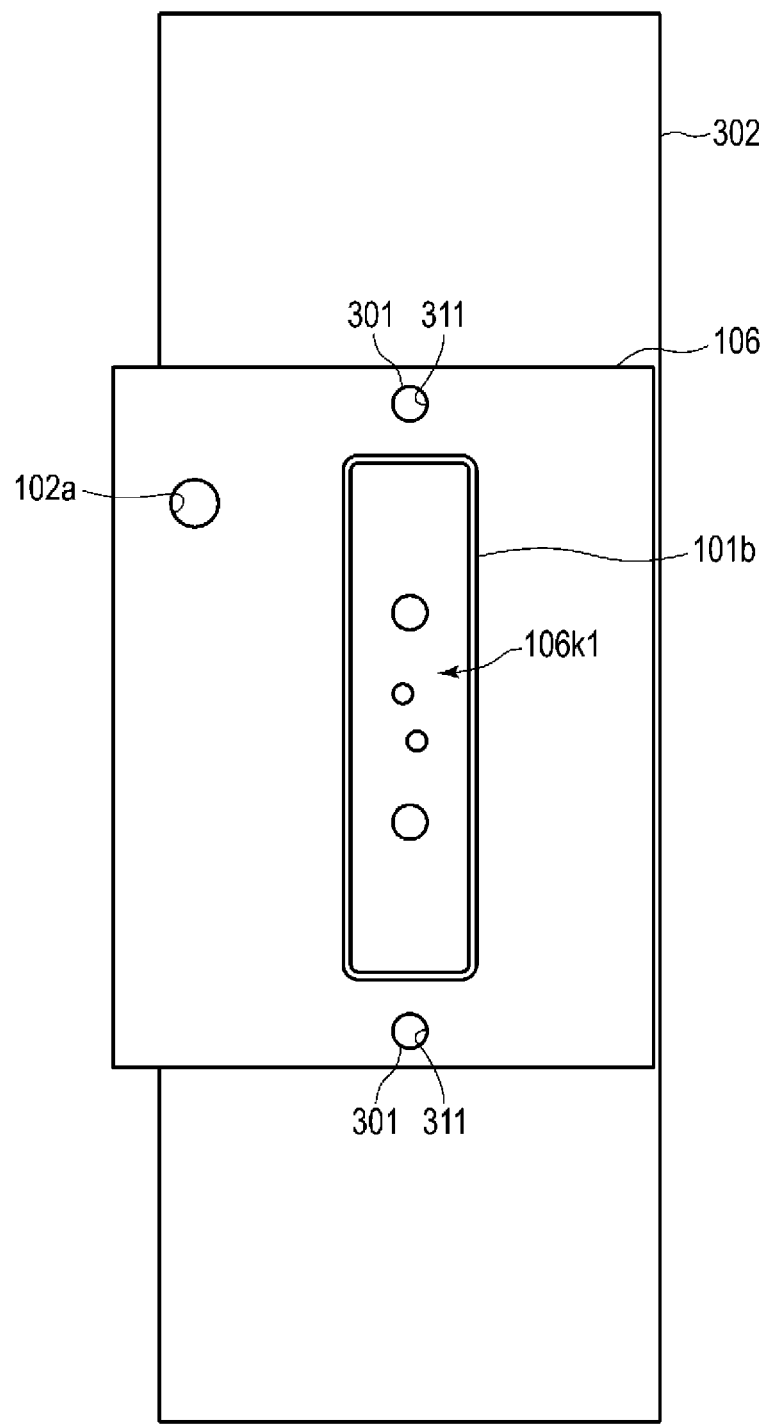

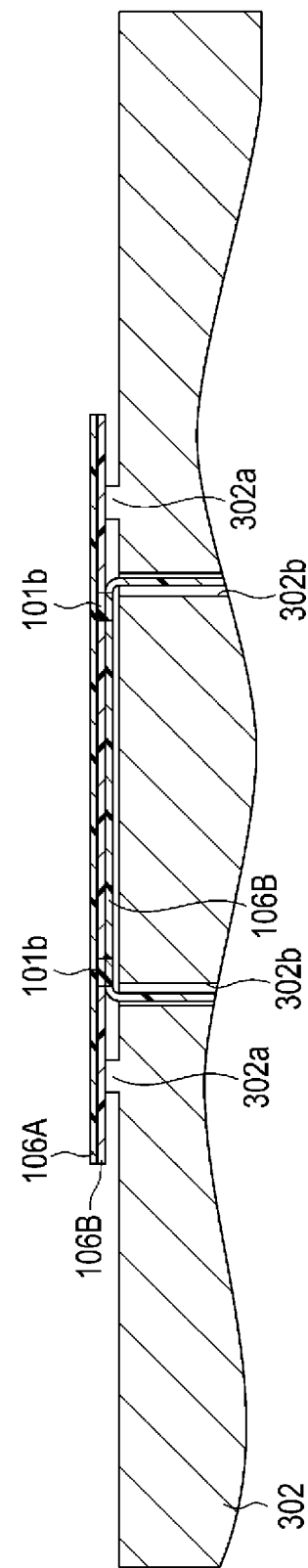
[FIG. 32]

[FIG. 33]
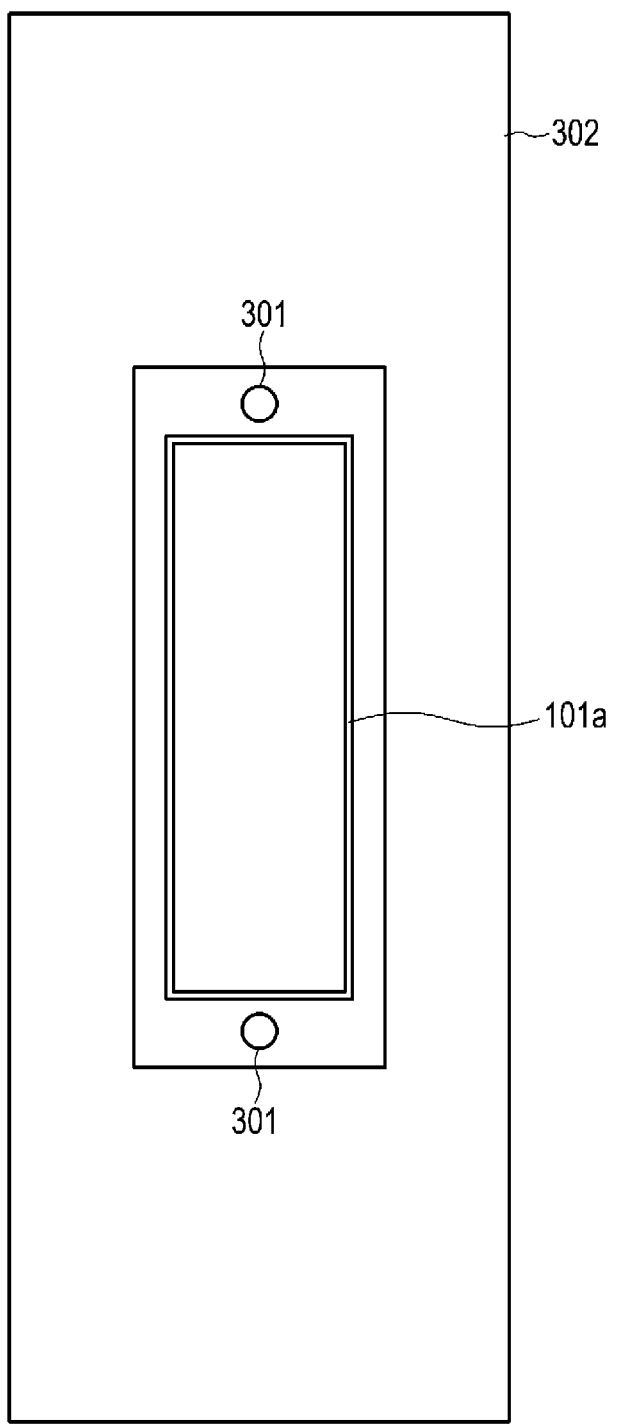

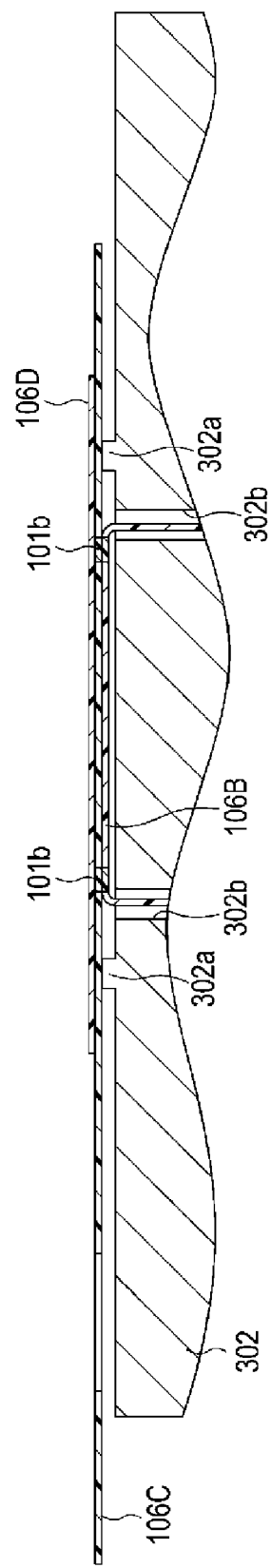
[FIG. 34]

[FIG. 35]
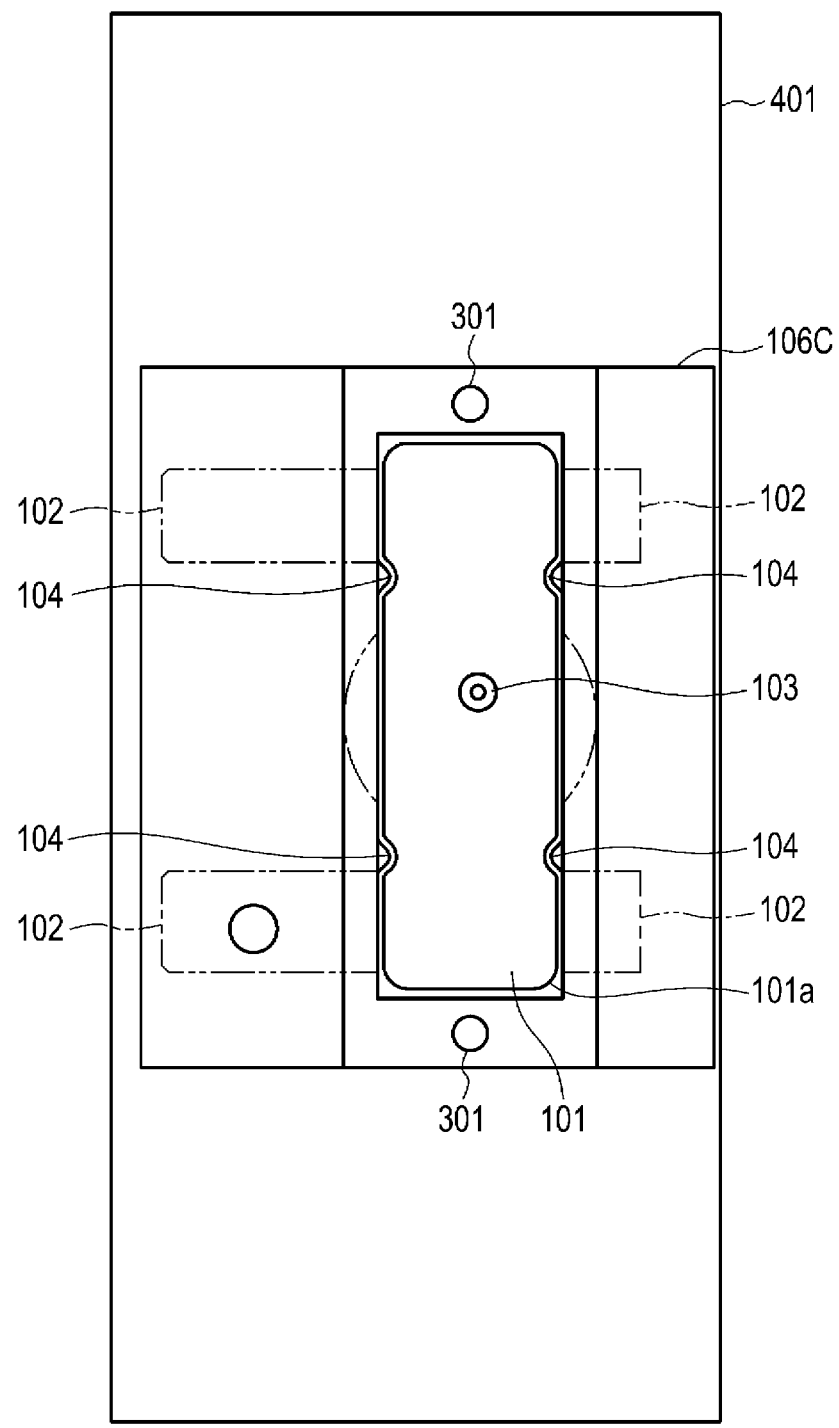

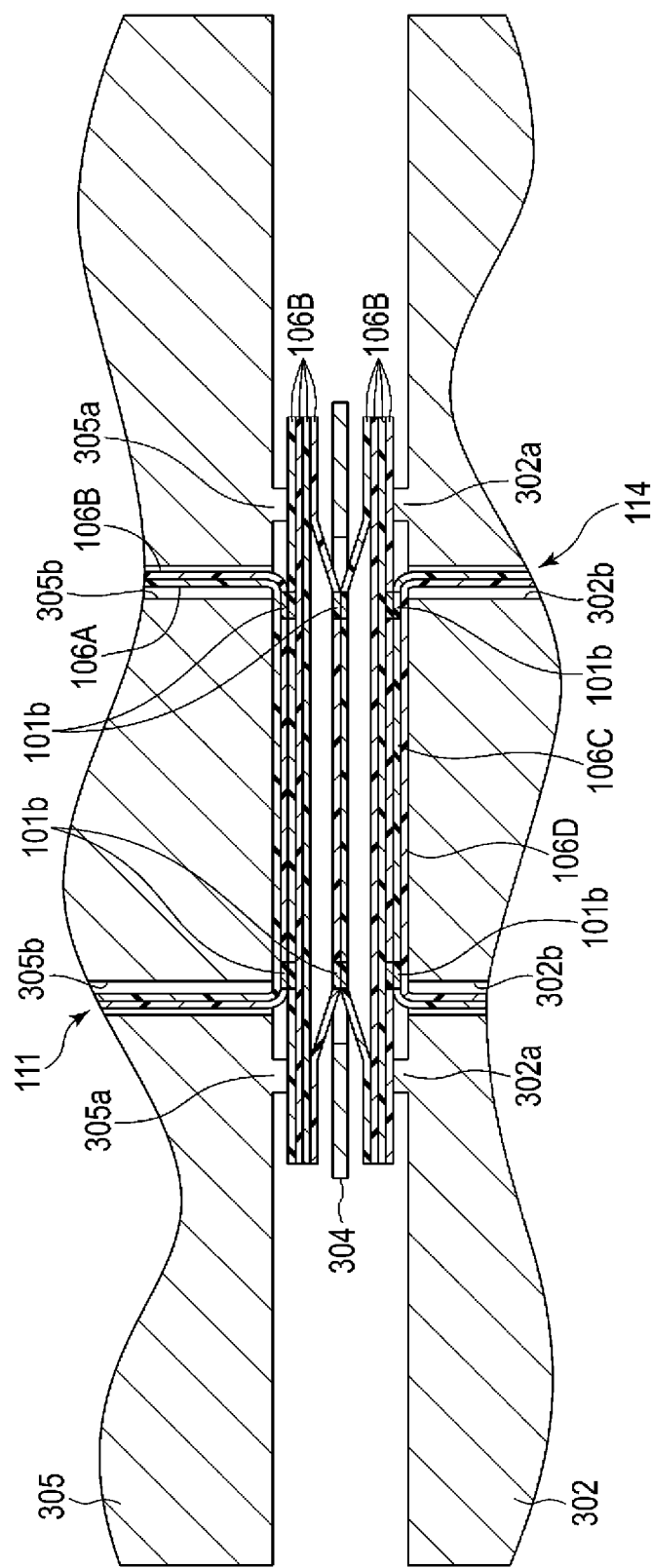

[FIG. 37]
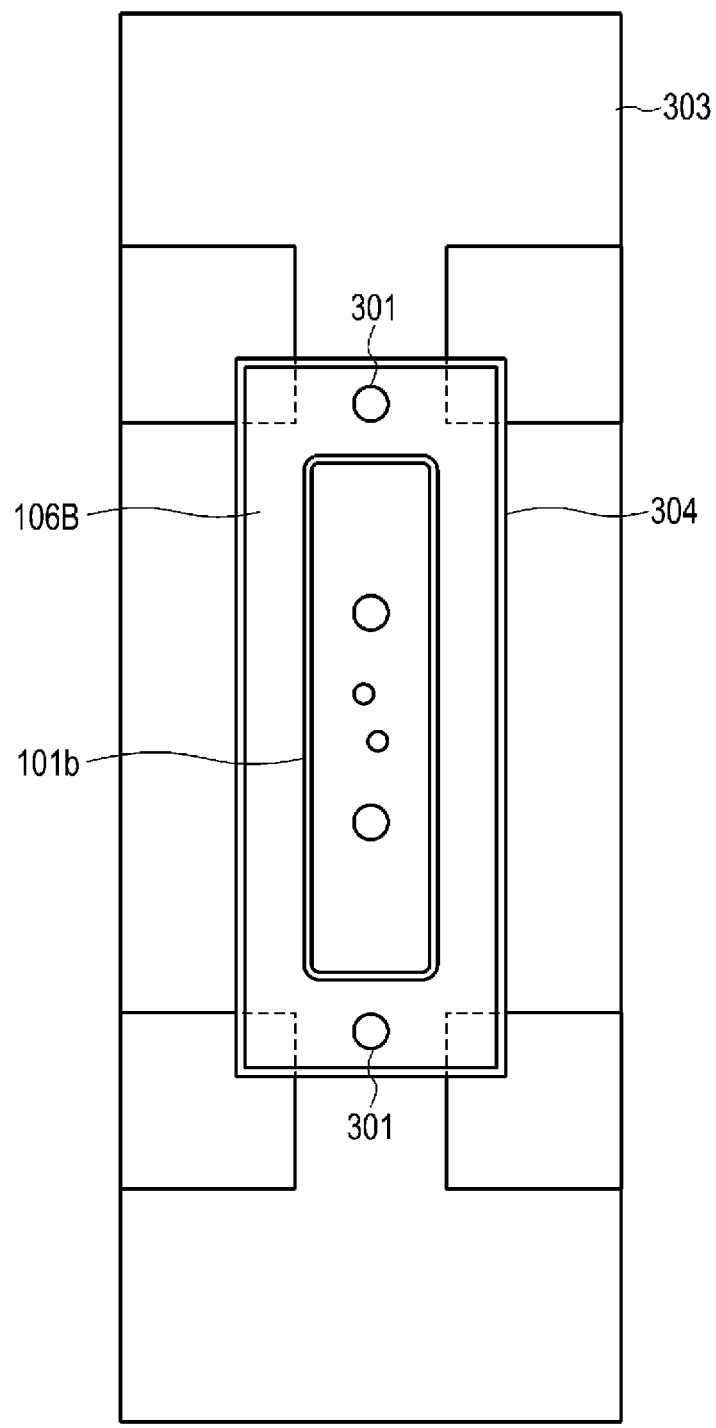

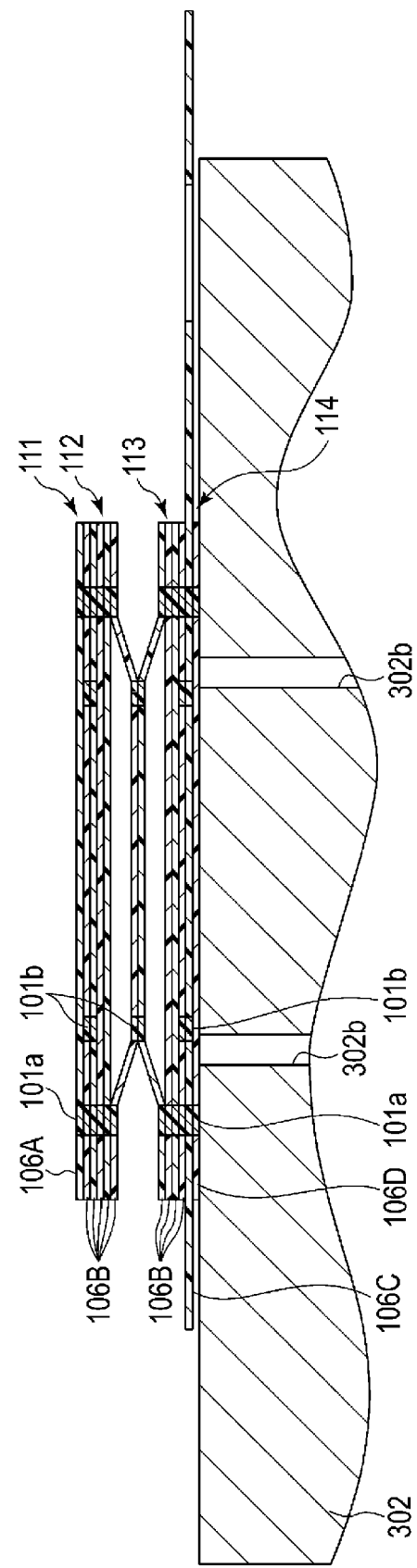

[FIG. 39]
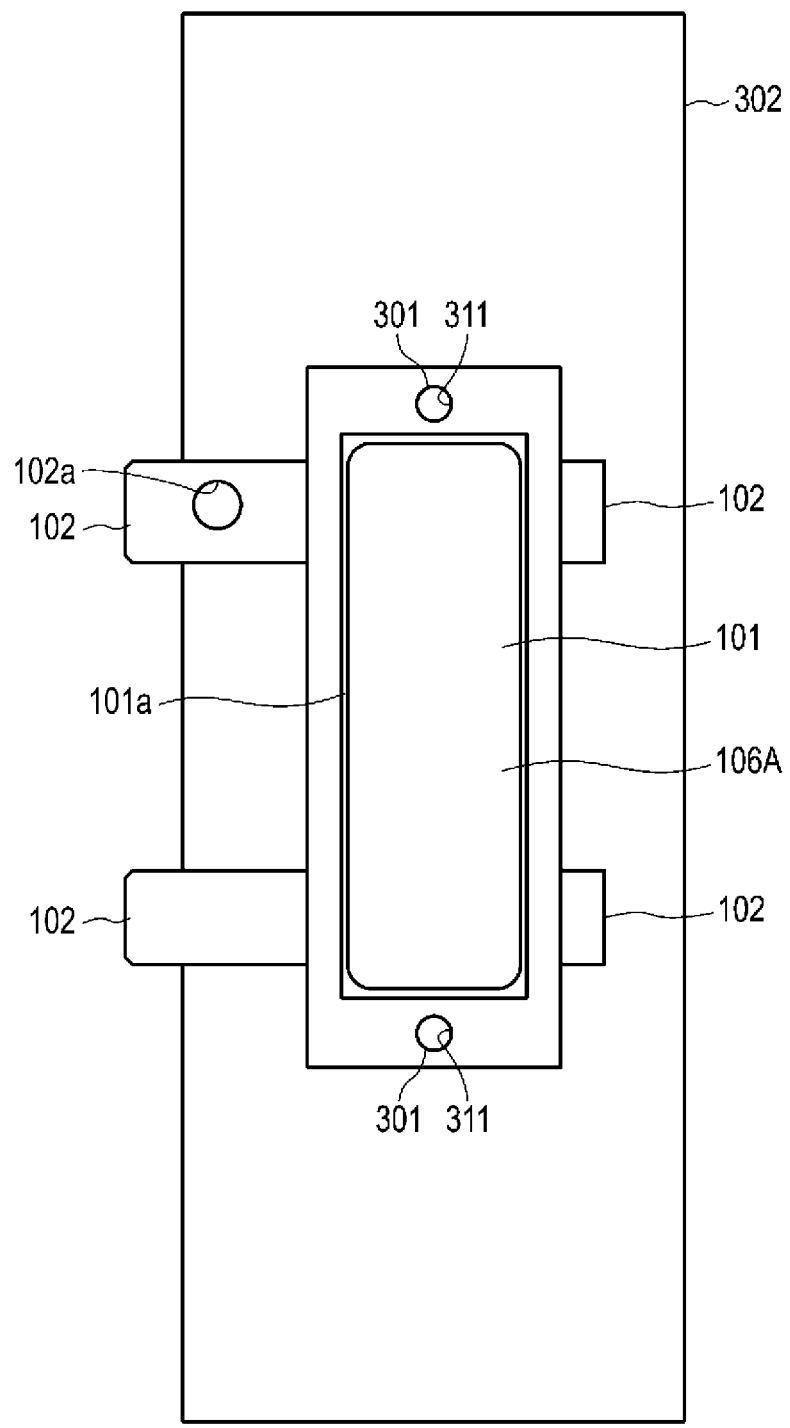

[FIG. 40]
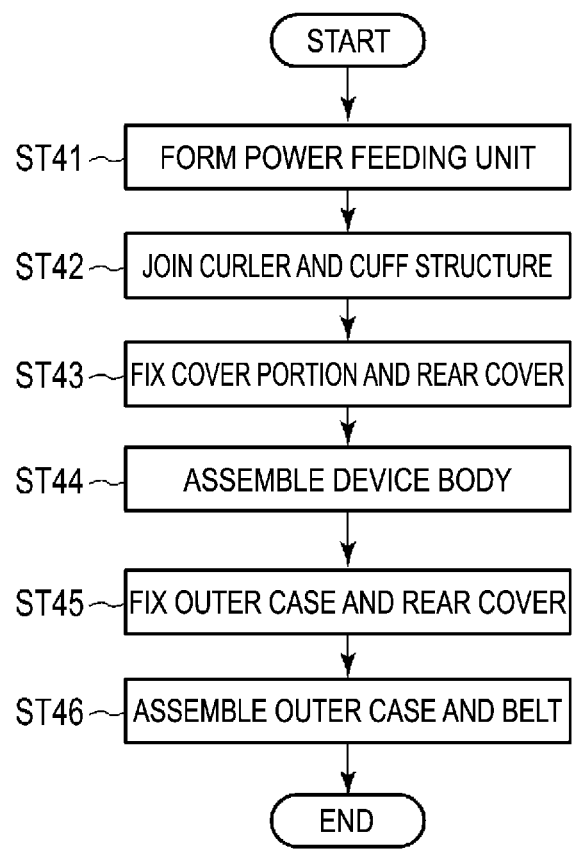

[FIG. 41]
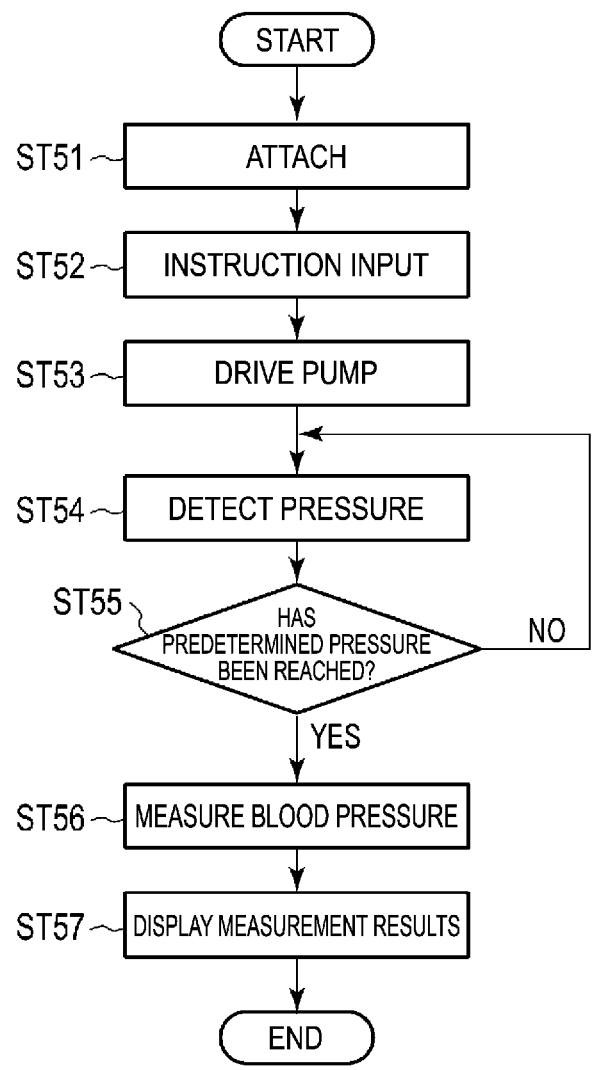

[FIG. 42]
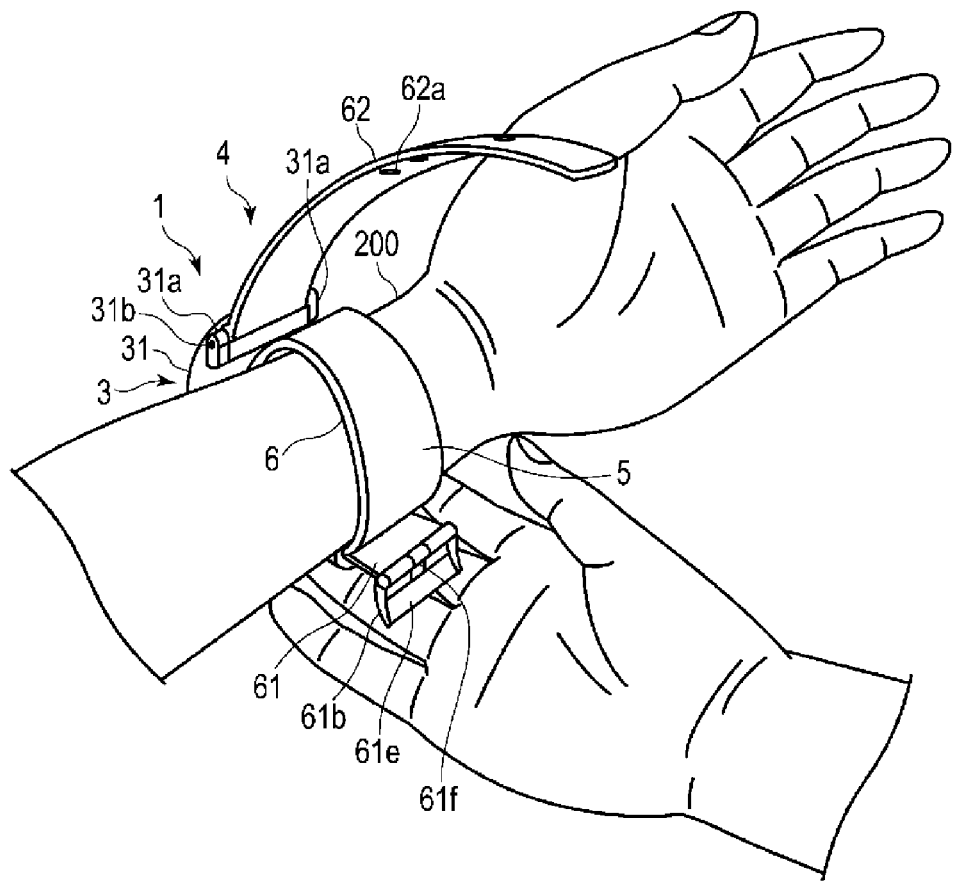

[FIG. 43]
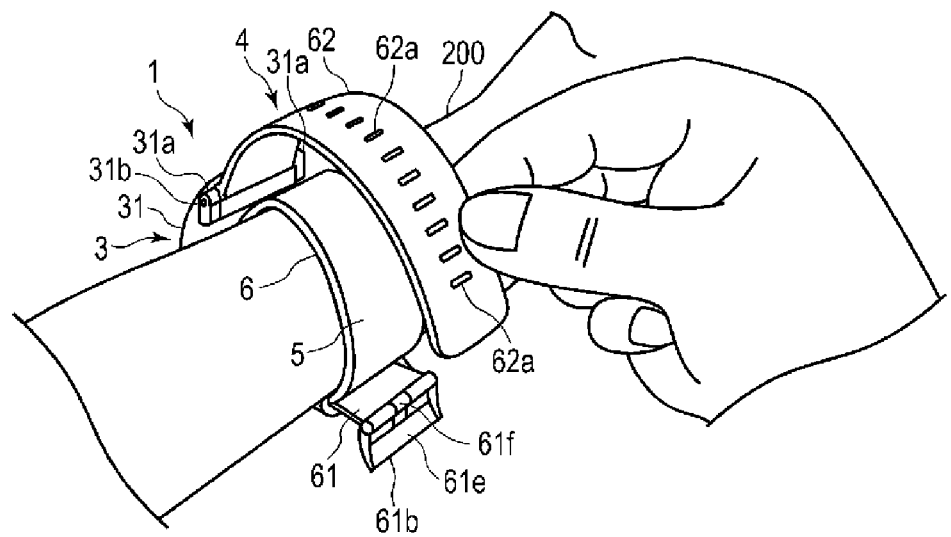
[FIG. 44]
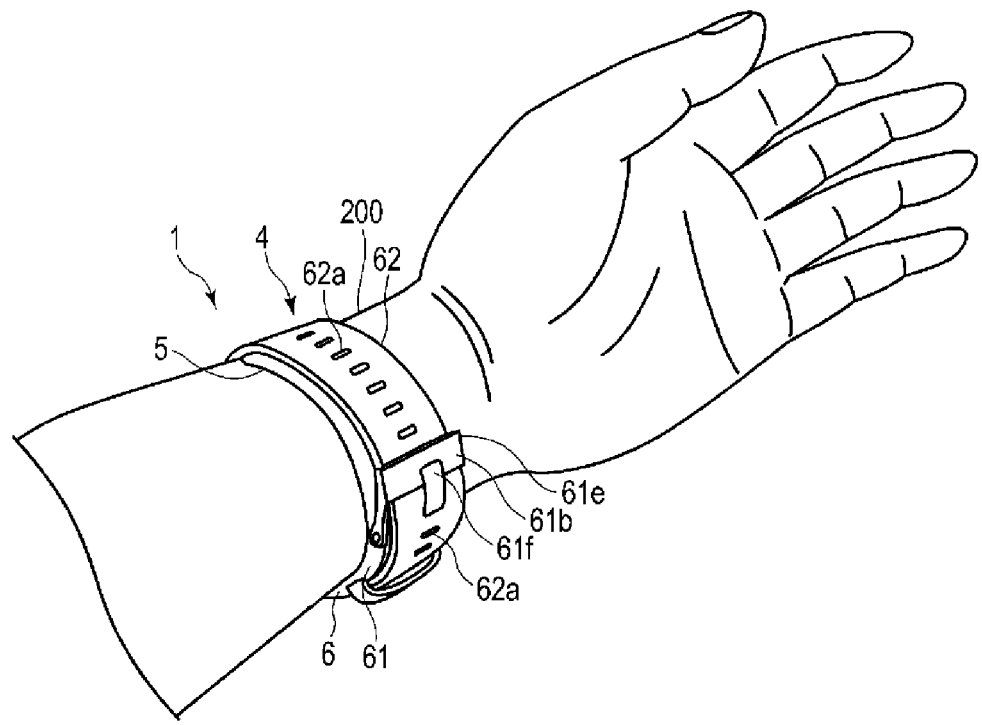

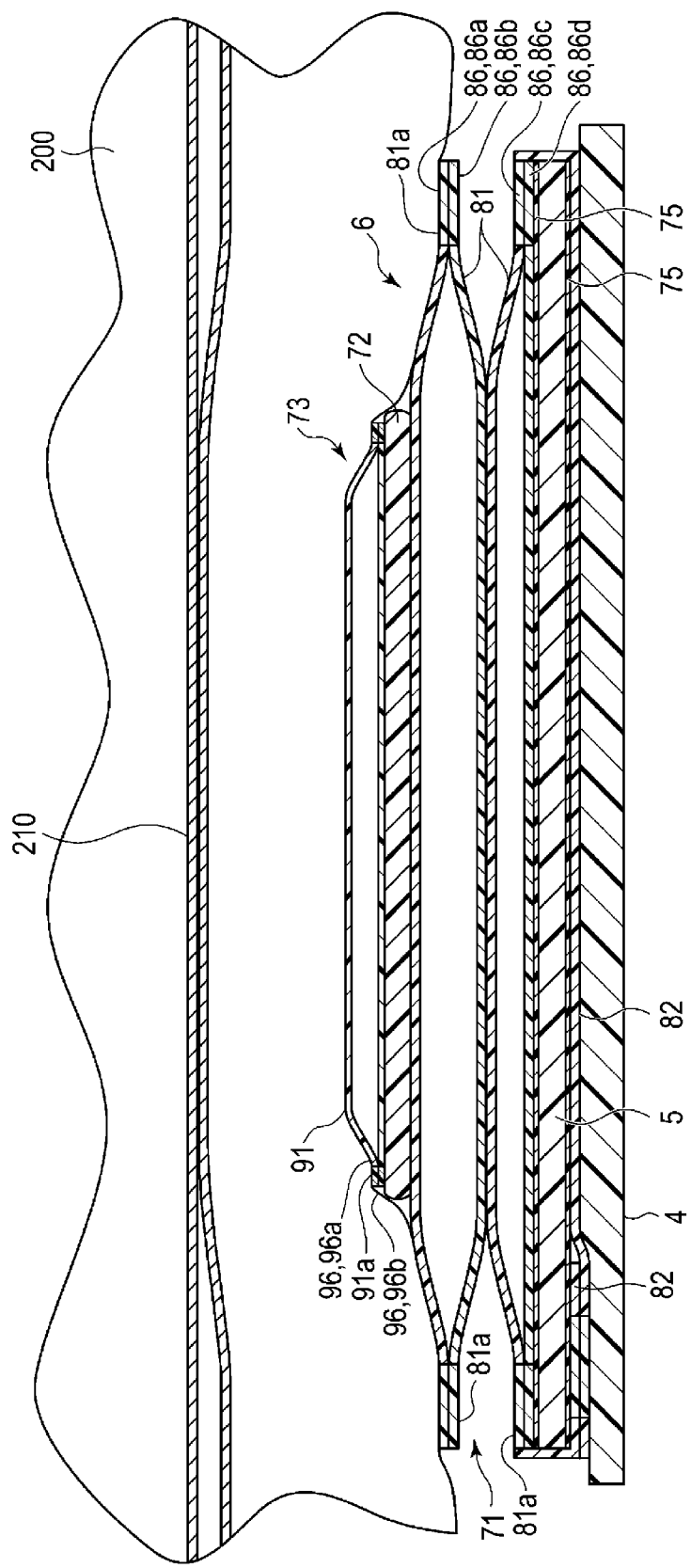
[FIG. 45]

METHOD FOR MANUFACTURING CUFF FOR BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/048031, filed Dec. 9, 2019, which application claims priority to Japan Patent Application No. 2018-246134, filed Dec. 27, 2018, which applications are incorporated herein by reference in their entireties.

TECHNICAL FIELD

The present invention relates to a method for manufacturing a cuff used in a blood pressure measurement device.

BACKGROUND ART

In recent years, blood pressure measurement devices for measuring blood pressure are being used to monitor health status at home, as well as in medical facilities. A blood pressure measurement device detects vibration of the artery wall to measure blood pressure by, for example, inflating and contracting a cuff wrapped around the upper arm or the wrist of a living body and detecting the pressure of the cuff using a pressure sensor. An example of a cuff used in such a blood pressure measurement device is the known technology described in JP 2006-174860 A in which the cuff includes three-layer bag-like structures.

Also, a wearable device attached to the wrist has been proposed for the blood pressure measurement device described above, and there has been a demand for further miniaturization. Furthermore, for compact blood pressure measurement devices, there is a demand to add more layers to the cuff to achieve a suitable blood pressure measurement accuracy even with a smaller sized cuff.

CITATION LIST

Patent Literature

Patent Document 1: JP 2006-174860 A

SUMMARY OF INVENTION

Technical Problem

However, as the number of layers of cuffs increases, the cuff may expand in the direction orthogonal to the stack direction, i.e., bulge laterally, when the cuff is inflated, causing the cuff to be unable to suitably press against the wrist. In addition, because the bag-like structure is formed from two sheet members, a process of welding together the bag-like structures is necessary each time a layer is added. This problematically increases the number of manufacturing processes.

Thus, an object of the present invention is to provide a method for manufacturing a cuff for a blood pressure measurement device including a plurality of bag-like structures that can prevent lateral bulging and can reduce the number of manufacturing processes.

Solution to Problem

According to an aspect, a method for manufacturing a cuff for a blood pressure measurement device including six-layer bag-like structures each formed from two sheet members, a first outer layer including one of the bag-like structures, a first intermediate layer constituted by two-layer of the bag-like structures and stacked on the first outer layer, a second intermediate layer constituted by two-layer of the bag-like structures and stacked on the first intermediate layer, and a second outer layer constituted by one of the bag-like structures and stacked on the second intermediate layer. The method includes, bridge welding together, each on the inside from an outer peripheral edge shape of the bag-like structures, the sheet member, facing the first intermediate layer, of the first outer layer and the sheet member, facing the first outer layer, of the bag-like structure, facing the first outer layer, of the first intermediate layer, the sheet member, facing the second intermediate layer, of the bag-like structure, facing the second intermediate layer, of the first intermediate layer and the sheet member, facing the first intermediate layer, of the bag-like structure, facing the first intermediate layer, of the second intermediate layer, and the sheet member, facing the second outer layer, of the bag-like structure, facing the second outer layer, of the second intermediate layer and the sheet member, facing the second intermediate layer, of the second outer layer, disposing each of two of the sheet members not bridge welded between the sheet member of the first intermediate layer bridge welded with the sheet member of the first outer layer and the sheet member of the first intermediate layer bridge welded with the sheet member of the second intermediate layer and between the sheet member of the second intermediate layer bridge welded with the sheet member of the first intermediate layer and the sheet member of the second intermediate layer bridge welded with the sheet member of the second outer layer, and welding the four sheet members constituting the first intermediate layer and the four sheet members constituting the second intermediate layer each in an outer peripheral edge shape of the bag-like structures.

Here, the fluid includes a liquid and air. The cuff is wrapped around the wrist or the like of a living body to measure blood pressure and includes a single or multi-layer bag-like structure that is inflated by being supplied with a fluid. The bag-like structure is inflated by fluid, and is an air bag in a case where the fluid is air.

The first outer layer is the first layer on the end portion side in the stacking direction of the six-layer bag-like structures. Also, the first intermediate layer includes the second and third bag-like structures stacked on the first bag-like structure. Also, the second intermediate layer includes the fourth and fifth bag-like structures connected to the third bag-like structure. The second outer layer is the sixth layer on the other end portion side in the stacking direction of the six-layer bag-like structures.

Additionally, bridge welding is welding to join adjacent bag-like structures, in which the sheet members are welded together on the inside from the weld portion on the outer peripheral edge of the bag-like structures.

According to this aspect, in a case of manufacturing a cuff including six-layer bag-like structures, the second and third bag-like structures corresponding to the first intermediate layer and the fourth and fifth bag-like structures corresponding to the second intermediate layer are each formed by welding four sheet members all together. Thus, the welding processes can be reduced.

In addition, opposing sheet members of the first layer and the second layer, opposing sheet members of the third layer and the fourth layer, and opposing sheet members of the fifth layer and the sixth layer are bridge welded together in advance. Thus, the bag-like structures can be easily formed without needing to weld together the formed bag-like structures. Additionally, for bridge welding to weld together the sheet members of the adjacent bag-like structures, only three section are welded in the stacking direction, allowing the processes for welding together the bag-like structures to be reduced.

With this method for manufacturing the cuff for the blood pressure measurement device, the manufacturing processes can be reduced, and manufacture is made easy. In addition, because the second and third bag-like structures and the fourth and fifth bag-like structures are integrally constituted by the weld portion of the outer peripheral edge of the cuff, even in a case where a six-layer bag-like structure is provided, the weld portion of the outer peripheral edge of the bag-like structures are at four sections. That is, even with six-layer bag-like structures, the cuff has a four layer structure constituted of the two outer layers and the two intermediate layers. Thus, the second and third bag-like structures and the fourth and fifth bag-like structures are suppressed from deforming in the direction orthogonal to the stacking direction. Thus, when the cuff is provided on the blood pressure measurement device and the blood pressure measurement device is attached on the wrist and inflated, lateral bulging in the cuff can be prevented from occurring.

In the method for manufacturing the cuff for the blood pressure measurement device according to the one aspect described above, the method for manufacturing the cuff for the blood pressure measurement device is provided, which further includes, disposing an intermediate electrode having a plate-like shape between the sheet member of the first intermediate layer and the sheet member of the second intermediate layer that are bridge welded, disposing the sheet members being bridge welded and the sheet members being non-bridge welded between a lower mold and an upper mold, the sheet members being bridge welded constituting the first outer layer, the first intermediate layer, the second intermediate layer, and the second outer layer, and welding the four sheet members constituting the first intermediate layer and the four sheet members constituting the second intermediate layer with the lower mold, the intermediate electrode, and the upper mold.

According to this aspect, because the intermediate electrode is disposed between the sheet members of the third bag-like structure and the fourth bag-like structure, the four sheet members constituting the second and third bag-like structures and the four sheet members constituting the fourth and fifth bag-like structures can respectively be welded. Accordingly, the method for manufacturing the cuff is made easier, and because the lower mold, the upper mold, and the intermediate electrode can be used as an electrode for welding, the manufacturing device can be given a simpler configuration.

In the method for manufacturing the cuff for the blood pressure measurement device according to the one aspect described above, the method for manufacturing the cuff for the blood pressure measurement device is provided, which further includes welding the four sheet members constituting the first intermediate layer and the four sheet members constituting the second intermediate layer at the same time.

According to this aspect, the manufacturing processes can be reduced by welding the first intermediate layer and the second intermediate layer at the same time.

In the method for manufacturing the cuff for the blood pressure measurement device according to the one aspect described above, the method for manufacturing the cuff for the blood pressure measurement device is provided, which further includes, disposing the sheet members in the sheet members of the first outer layer being bridge welded, forming the first outer layer by welding two of the sheet members, being disposed in an outer peripheral edge shape of the bag-like structures, disposing the sheet members in the sheet members of the second outer layer being bridge welded, forming the second outer layer by welding two of the sheet members, being disposed in an outer peripheral edge shape of the bag-like structures, and welding, after the first outer layer and the second outer layer are formed, the four sheet members constituting the first intermediate layer and the four sheet members constituting the second intermediate layer with the lower mold, the intermediate electrode, and the upper mold.

According to this aspect, by forming the first outer layer and the second outer layer in advance, compared to a case where the first outer layer and the second outer layer are formed after forming the first intermediate layer and the second intermediate layer, the outer peripheral edge of the bag-like structures is welded with the lower mold, the upper mold, and the intermediate electrode, with easier work of escaping from each of the molds.

In the method for manufacturing the cuff for the blood pressure measurement device according the one aspect described above, the method for manufacturing the cuff for the blood pressure measurement device is provided, which further includes, disposing two sheet members constituting a bag-like structure, bridge welding two sets of the two sheet members on the inside from an outer peripheral edge shape of the bag-like structures, disposing two of the sheet members being non-bridge welded between the two sheet members being bridge welded of the two sets, welding, from among the two sheet members being bridge welded of the two sets, two of the sheet members facing the two sheet members disposed between the two sheet members being bridge welded of the two sets and two of the sheet members disposed between the two sheet members being bridge welded of the two sets, in an outer peripheral edge shape of the bag-like structures.

According to this aspect, because the two adjacent bag-like structures can be formed by integrally welding the four sheet members, the welding processes can be reduced, and deformation in the direction orthogonal to the stacking direction of the two adjacent bag-like structures can be suppressed. Thus, when the cuff is provided on the blood pressure measurement device and attached on the wrist and inflated, lateral bulging in the cuff can be prevented.

Advantageous Effects of Invention

The present invention can provide a method for manufacturing a cuff for a blood pressure measurement device that can prevent lateral bulging and can reduce the number of manufacturing processes.

BRIEF DESCRIPTION OF DRAWINGS

FIG. 1 is a perspective view illustrating a configuration of a blood pressure measurement device according to a first embodiment of the present invention.

FIG. 2 is an exploded perspective view illustrating the configuration of the blood pressure measurement device.

FIG. 3 is a side view illustrating the configuration of the blood pressure measurement device.

FIG. 4 is an explanatory diagram illustrating a state in which the blood pressure measurement device is attached to the wrist.

FIG. 5 is a block diagram illustrating the configuration of the blood pressure measurement device.

FIG. 6 is a perspective view illustrating the configuration of the blood pressure measurement device.

FIG. 7 is an exploded perspective view illustrating the configuration of a curler and a cuff structure of the blood pressure measurement device.

FIG. 8 is a cross-sectional view illustrating the configuration of the curler and the cuff structure of the blood pressure measurement device.

FIG. 9 is a cross-sectional view illustrating the configuration of the curler and the cuff structure of the blood pressure measurement device.

FIG. 10 is a cross-sectional view illustrating the configuration of a tensile cuff of the blood pressure measurement device.

FIG. 11 is a cross-sectional view illustrating the configuration of the tensile cuff of the blood pressure measurement device.

FIG. 12 is a perspective view illustrating the configuration of the curler of the blood pressure measurement device.

FIG. 13 is a plan view illustrating a configuration of a cuff structure of the blood pressure measurement device.

FIG. 14 is a plan view illustrating the configuration of the cuff structure.

FIG. 15 is a plan view illustrating a configuration of a pressing cuff of the blood pressure measurement device.

FIG. 16 is a cross-sectional view illustrating the configuration of the pressing cuff.

FIG. 17 is a plan view illustrating the configuration of a sensing cuff of the blood pressure measurement device.

FIG. 18 is a cross-sectional view illustrating the configuration of the sensing cuff.

FIG. 19 is a plan view illustrating the configuration of the tensile cuff of the blood pressure measurement device.

FIG. 20 is a cross-sectional view illustrating the configuration of the tensile cuff of the blood pressure measurement device.

FIG. 21 is a flowchart illustrating an example of a method for manufacturing the sensing cuff.

FIG. 22 is a flowchart illustrating an example of a method for manufacturing the tensile cuff.

FIG. 23 is a flowchart illustrating an example of a method for manufacturing the pressing cuff.

FIG. 24 is a plan view illustrating the configuration of a first sheet.

FIG. 25 is a plan view illustrating the configuration of a second sheet.

FIG. 26 is a plan view illustrating the configuration of a third sheet.

FIG. 27 is a plan view illustrating the configuration of a fourth sheet.

FIG. 28 is an explanatory diagram illustrating an example of the processes of a method for manufacturing the tensile cuff.

FIG. 29 is an explanatory diagram illustrating an example of the processes of the method for manufacturing the tensile cuff.

FIG. 30 is an explanatory diagram illustrating an example of the processes of the method for manufacturing the tensile cuff.

FIG. 31 is an explanatory diagram illustrating an example of the processes of the method for manufacturing the tensile cuff.

FIG. 32 is an explanatory diagram illustrating an example of the processes of the method for manufacturing the tensile cuff.

FIG. 33 is an explanatory diagram illustrating an example of the processes of the method for manufacturing the tensile cuff.

FIG. 34 is an explanatory diagram illustrating an example of the processes of the method for manufacturing the tensile cuff.

FIG. 35 is an explanatory diagram illustrating an example of the processes of the method for manufacturing the tensile cuff.

FIG. 36 is an explanatory diagram illustrating an example of the processes of the method for manufacturing the tensile cuff.

FIG. 37 is an explanatory diagram illustrating an example of the processes of the method for manufacturing the tensile cuff.

FIG. 38 is an explanatory diagram illustrating an example of the processes of the method for manufacturing the tensile cuff.

FIG. 39 is an explanatory diagram illustrating an example of the processes of the method for manufacturing the tensile cuff.

FIG. 40 is a flowchart illustrating an example of a method for manufacturing the blood pressure measurement device.

FIG. 41 is a flowchart illustrating an example of usage of the blood pressure measurement device.

FIG. 42 is a perspective view illustrating an example in which the blood pressure measurement device is attached to the wrist.

FIG. 43 is a perspective view illustrating an example in which the blood pressure measurement device is attached to the wrist.

FIG. 44 is a perspective view illustrating an example in which the blood pressure measurement device is attached to the wrist.

FIG. 45 is a cross-sectional view schematically illustrating a state in which the blood pressure measurement device is attached to the wrist.

DESCRIPTION OF EMBODIMENTS

An example of a blood pressure measurement device 1 according to an embodiment of the present invention is described below using FIGS. 1 to 20.

FIG. 1 is a perspective view illustrating a configuration of the blood pressure measurement device 1 according to a first embodiment of the present invention. FIG. 2 is an exploded perspective view illustrating the configuration of the blood pressure measurement device 1. FIG. 3 is a side view illustrating the configuration of the blood pressure measurement device 1. FIG. 4 is an explanatory diagram illustrating a state in which the blood pressure measurement device 1 is attached to the wrist 200. FIG. 5 is a block diagram illustrating the configuration of the blood pressure measurement device 1. FIG. 6 is a perspective view illustrating the configuration of the blood pressure measurement device 1 with some configurations removed. FIG. 7 is an exploded perspective view illustrating the configuration of a curler 5 and a cuff structure 6 of the blood pressure measurement device 1. FIG. 8 is a cross-sectional view illustrating the configuration of the curler 5 and the cuff structure 6 of the blood pressure measurement device 1. FIG. 9 is a cross-sectional view illustrating the configuration of the curler 5 and the cuff structure 6 of the blood pressure measurement device 1. FIG. 10 is a cross-sectional view illustrating the configuration of a tensile cuff 74 of the blood pressure measurement device 1. FIG. 11 is a cross-sectional view illustrating the configuration of a tensile cuff 74 of the blood pressure measurement device 1. FIG. 12 is a perspective view illustrating the configuration of the curler 5 of the blood pressure measurement device 1. FIG. 13 is a plan view illustrating a configuration of the cuff structure 6 of the blood pressure measurement device 1 from the wrist 200 side. FIG. 14 is a plan view illustrating the configuration of the curler 5 of the cuff structure 6 on the inner circumferential surface side.

FIG. 15 is a plan view illustrating the configuration of a pressing cuff 71 of the blood pressure measurement device 1. FIG. 16 is a cross-sectional view illustrating the configuration of the pressing cuff 71, which is a line cross-section along XVI-XVI illustrated in FIG. 15. FIG. 17 is a plan view illustrating the configuration of a sensing cuff 73 of the blood pressure measurement device 1. FIG. 18 is a cross-sectional view illustrating the configuration of the sensing cuff 73 of the blood pressure measurement device 1, which is a line cross-section along XVIII-XVIII illustrated in FIG. 17. FIG. 19 is a plan view illustrating the configuration of the tensile cuff 74 of the blood pressure measurement device 1. FIG. 20 is a cross-sectional view illustrating the configuration of the tensile cuff 74.

The blood pressure measurement device 1 is an electronic blood pressure measurement device attached to a living body. The present embodiment will be described using an electronic blood pressure measurement device having an aspect of a wearable device attached to the wrist 200 of the living body.

As illustrated in FIGS. 1 to 6, the blood pressure measurement device 1 includes a device body 3, a belt 4 that fixes the device body 3 at the wrist, the curler 5 disposed between the belt 4 and the wrist, the cuff structure 6 including the pressing cuff 71, the sensing cuff 73, and the tensile cuff 74, a fluid circuit 7 fluidly connecting the device body 3 and the cuff structure 6, and a power feeding unit 8 provided on the curler 5.

As illustrated in FIGS. 1 to 6, the device body 3 includes, for example, a case 11, a display unit 12, an operation unit 13, a pump 14, the flow path portion 15, the on-off valve 16, the pressure sensor 17, a power supply unit 18, a vibration motor 19, and a control substrate 20. The device body 3 supplies a fluid to the cuff structure 6 using the pump 14, the on-off valve 16, the pressure sensor 17, the control substrate 20, and the like.

As illustrated in FIGS. 1 to 3, the case 11 includes an outer case 31, a windshield 32 covering an opening of the outer case 31 on the opposite side (outer side) to the wrist 200, a base portion 33 provided inside the outer case 31 on the wrist 200 side, a rear cover 35 covering the wrist 200 side of the outer case 31, and a sealing member 36 provided on the lower surface of the rear cover 35.

The outer case 31 is formed in a cylindrical shape. The outer case 31 includes pairs of lugs 31a provided at respective symmetrical positions in the circumferential direction of an outer circumferential surface, and spring rods 31b each provided between each of the two pairs of lugs 31a. The windshield 32 is, for example, a circular glass plate.

The base portion 33 holds the display unit 12, the operation unit 13, the pump 14, the on-off valve 16, the pressure sensor 17, the power supply unit 18, the vibration motor 19, and the control substrate 20. Additionally, the base portion 33 constitutes a portion of the flow path portion 15 that makes the pump 14 and the cuff structure 6 fluidly continuous.

The rear cover 35 is constituted in an annular shape with an open center. The rear cover 35 covers the end portion on the outer peripheral edge side of the outer case 31 on the wrist 200 side. With the rear cover 35 configured as such being integrally assembled with the curler 5, the central opening is covered by the curler 5, and the rear cover 35 together with the curler 5 forms a rear lid covering the end portion of the outer case 31 on the wrist 200 side. Specifically, the rear cover 35 is fixed to the curler 5 with four first joining members 35a and fixed to the end portion of the outer case 31 on the wrist 200 side with four second joining members 35b. The rear cover 35 includes four hole portions 35c into which the first joining members 35a that are provided at the bottom portion and fixed to the curler 5 are inserted, and four hole portions 35d provided at four portions of the outer circumferential portion that radially project out, into which the second joining members 35b that are fixed to the outer case 31 are inserted.

The first joining members 35a and the second joining members 35b are members, such as a screw, a bolt, a machine screw, a rive, for mechanically joining two components. In the present embodiment, the first joining members 35a and the second joining members 35b are screws.

The sealing member 36 is a double-sided tape, for example, formed in the shape of the region of the rear cover 35 that comes into contact with the curler 5. The sealing member 36 seals between the curler 5 and the rear cover 35 by being provided between the curler 5 and the rear cover 35.

The display unit 12 is disposed on the base portion 33 of the outer case 31 and directly below the windshield 32. As illustrated in FIG. 5, the display unit 12 is electrically connected to the control substrate 20. The display unit 12 is, for example, a liquid crystal display or an organic electroluminescence display. The display unit 12 displays various types of information including the date and time and measurement results of blood pressure values such as the systolic blood pressure and diastolic blood pressure, heart rate, and the like.

The operation unit 13 is configured to be capable of receiving an instruction input from a user. For example, the operation unit 13 includes a plurality of buttons 41 provided on the case 11, a sensor 42 that detects operation of the buttons 41, and a touch panel 43 provided on the display unit 12 or the windshield 32, as illustrated in FIGS. 1 and 5. When operated by the user, the operation unit 13 converts an instruction into an electrical signal. The sensor 42 and the touch panel 43 are electrically connected to the control substrate 20 to output electrical signals to the control substrate 20.

As the plurality of buttons 41, for example, three buttons are provided. The buttons 41 are supported by the base portion 33 and protrude from the outer circumferential surface of the outer case 31. The plurality of buttons 41 and a plurality of the sensors 42 are supported by the base portion 33. The touch panel 43 is integrally provided on the windshield 32, for example.

The pump 14 is, for example, a piezoelectric pump. The pump 14 compresses air and supplies compressed air to the cuff structure 6 through the flow path portion 15. The pump 14 is electrically connected to the control substrate 20.

The flow path portion 15 constitutes the flow path connecting from the pump 14 to the pressing cuff 71 and the tensile cuff 74 and a flow path connecting from the pump 14 to the sensing cuff 73, as illustrated in FIG. 5. Additionally, the flow path portion 15 constitutes a flow path connecting from the pressing cuff 71 and the tensile cuff 74 to the atmosphere, and a flow path connecting from the sensing cuff 73 to the atmosphere. The flow path portion 15 is a flow path of air constituted by a hollow portion, a groove, a flow path tank, a tube, or the like provided in the base portion 33 and the like.

The on-off valve 16 opens and closes a portion of the flow path portion 15. Specifically, a plurality of on-off valves 16, specifically four on-off valves 16 are provided, for example, as illustrated in FIG. 5, and selectively open and close the flow path connecting from the pump 14 to the pressing cuff 71 and the tensile cuff 74, the flow path connecting from the pump 14 to the sensing cuff 73, the flow path connecting from the pressing cuff 71 and the tensile cuff 74 to the atmosphere, and the flow path connecting from the sensing cuff 73 to the atmosphere, by the combination of opening and closing of each of the on-off valves 16. As a specific example, the four on-off valves 16 are constituted by the first on-off valve 16A, the second on-off valve 16B, the third on-off valve 16C, and the fourth on-off valve 16D. The first on-off valve 16A opens and closes the flow path connecting the pump 14 and the sensing cuff 73. The second on-off valve 16B opens and closes the flow path connecting the pump 14 and the tensile cuff 74. The second on-off valve 16B and the third on-off valve 16C open and close the flow path connecting the pump 14 and the pressing cuff 71. The second on-off valve 16B, the third on-off valve 16C, and the fourth on-off valve 16D open and close the flow path connecting the pump 14 and the atmosphere.

The pressure sensor 17 at least detects the pressure of the sensing cuff 73. The pressure sensor 17 is provided with the first pressure sensor 17A and the second pressure sensor 17B, for example. The pressure sensor 17 converts a detected pressure into an electrical signal, and outputs the electrical signal to the control substrate 20. For example, the first pressure sensor 17A and the second pressure sensor 17B are provided in the flow path connecting the first on-off valve 16A of the flow path portion 15 and the sensing cuff 73. The flow path is continuous through the pressing cuff 71, the sensing cuff 73, and the tensile cuff 74 to the pump 14 by the opening and closing of each of the on-off valves, and thus the pressure in these flow paths corresponds to the pressure in the internal space of the pressing cuff 71, the sensing cuff 73, and the tensile cuff 74 connecting to the pump 14.

Specifically, for example, the pressure sensor 17 detects the pressure of the sensing cuff 73, i.e., the pressure of the flow path portion 15 connecting the pump 14 and the sensing cuff 73, when the first on-off valve 16A is open and the second on-off valve 16B is closed. Also, the pressure sensor 17 detects the pressure of the sensing cuff 73 and the tensile cuff 74, i.e., the pressure of the flow path portion 15 connecting the pump 14, the sensing cuff 73, and the tensile cuff 74, when the first on-off valve 16A and the second on-off valve 16B are open and the third on-off valve 16C is closed. Furthermore, the pressure sensor 17 detects the pressure of the pressing cuff 71, the sensing cuff 73, and the tensile cuff 74, i.e., the pressure of the flow path portion 15 connecting the pump 14, the pressing cuff 71, the sensing cuff 73, and the tensile cuff 74, when the first on-off valve 16A, the second on-off valve 16B, and the third on-off valve 16C are open and the fourth on-off valve 16D is open or closed.

The power supply unit 18 is, for example, a secondary battery such as a lithium ion battery. The power supply unit 18 is electrically connected to the control substrate 20, as illustrated in FIG. 5. The power supply unit 18 supplies power to the control substrate 20.

As illustrated in FIG. 5, the control substrate 20 includes, for example, a substrate 51, an acceleration sensor 52, a communication unit 53, a storage unit 54, and a control unit 55. The control substrate 20 is constituted by the acceleration sensor 52, the communication unit 53, the storage unit 54, and the control unit 55 that are mounted on the substrate 51.

The substrate 51 is fixed to the base portion 33 of the case 11 using screws or the like.

The acceleration sensor 52 is, for example, a 3-axis acceleration sensor. The acceleration sensor 52 outputs, to the control unit 55, an acceleration signal representing acceleration of the device body 3 in three directions orthogonal to one another. For example, the acceleration sensor 52 is used to measure, from the detected acceleration, the amount of activity of a living body to which the blood pressure measurement device 1 is attached.

The communication unit 53 is configured to be capable to transmit and receive information to and from an external device wirelessly or by wire. For example, the communication unit 53 transmits information controlled by the control unit 55, and information of a measured blood pressure value, a pulse, and the like to an external device via a network, and receives a program or the like for software update from an external device via a network and sends the program or the like to the control unit 55.

In the present embodiment, the network is, for example, the Internet, but is not limited to this. The network may be a network such as a Local Area Network (LAN) provided in a hospital or may be direct communication with an external device using a cable or the like including a terminal of a predetermined standard such as a USB. Thus, the communication unit 53 may be configured to include a plurality of wireless antennas, micro-USB connectors, or the like.

The storage unit 54 pre-stores program data for controlling the overall blood pressure measurement device 1 and a fluid circuit 7, settings data for setting various functions of the blood pressure measurement device 1, calculation data for calculating a blood pressure value and a pulse from pressure measured by the pressure sensors 17, and the like. Additionally, the storage unit 54 stores information such as a measured blood pressure value and a measured pulse.

The control unit 55 is constituted by one or more CPUs, and controls operation of the overall blood pressure measurement device 1 and operation of the fluid circuit. The control unit 55 is electrically connected to and supplies power to the display unit 12, the operation unit 13, the pump 14, each of the on-off valves 16 and the pressure sensors 17. Additionally, the control unit 55 controls operation of the display unit 12, the pump 14, and the on-off valves 16, based on electrical signals output by the operation unit 13 and the pressure sensors 17.

For example, as illustrated in FIG. 5, the control unit 55 includes a main Central Processing Unit (CPU) 56 that controls operation of the overall blood pressure measurement device 1, and a sub-CPU 57 that controls operation of the fluid circuit 7. For example, the main CPU 56 obtains measurement results such as blood pressure values, for example, the systolic blood pressure and the diastolic blood pressure, and the heart rate, from electrical signals output by the pressure sensor 17, and outputs an image signal corresponding to the measurement results to the display unit 12.

For example, the sub-CPU 57 drives the pump 14 and the on-off valves 16 to feed compressed air to the pressing cuff 71 and the sensing cuff 73 when an instruction to measure the blood pressure is input from the operation unit 13. In addition, the sub-CPU 57 controls driving and stopping of the pump 14 and opening and closing of the on-off valves 16 based on electrical signal output by the pressure sensors 17.

The sub-CPU 57 controls the pump 14 and the on-off valves 16 to selectively feed compressed air to the pressing cuff 71 and the sensing cuff 73 and selectively depressurize the pressing cuff 71 and the sensing cuff 73.

As illustrated in FIGS. 1 to 4, the belt 4 includes a first belt 61 provided on the first pair of lugs 31a and a first spring rod 31b, and a second belt 62 provided on the second pair of lugs 31a and a second spring rod 31b. The belt 4 is wrapped around the wrist 200 with a curler 5 in between.

The first belt 61 is referred to as a so-called a parent and is configured like a band capable of being joined to the second belt 62. As illustrated in FIGS. 1 to 3, the first belt 61 includes a belt portion 61a and a buckle 61b. The belt portion 61a is configured like a band. The belt portion 61a is formed of an elastically deformable resin material. In addition, the belt portion 61a is flexible and includes a sheet-like insert member inside the belt portion 61a for suppressing stretching in the longitudinal direction of the belt portion 61a. The belt portion 61a includes a first hole portion 61c that is formed at one end portion and extends orthogonal to the longitudinal direction of the belt portion 61a, and a second hole portion 61d that is formed at the other end portion and extends orthogonal to the longitudinal direction of the first belt 61.

As illustrated in FIGS. 4 and 6, the first hole portion 61c is provided at the end portion of the belt portion 61a The first hole portion 61c has an inner diameter at which the spring rod 31b can be inserted into the first hole portion 61c and at which the first belt 61 can rotate with respect to the spring rod 31b. In other words, the first belt 61 is rotatably held by the outer case 31 by disposing the first hole portion 61c between the pair of lugs 31a and around the spring rod 31b.

As illustrated in FIGS. 1 and 3, the second hole portion 61d is provided at the leading end of the belt portion 61a The buckle 61b is attached to the second hole portion 61d.

As illustrated in FIGS. 1 and 3, the buckle 61b includes a frame body 61e in a rectangular frame shape and a prong 61f rotatably attached to the frame body 61e. A side of the frame body 61e to which the prong 61f is attached is inserted into the second hole portion 61d, and the frame body 61e is mounted rotatably with respect to the belt portion 61a.

The second belt 62 is referred to as a so-called blade tip, and is configured in a band-like shape having a width at which the second belt 62 can be inserted into the frame body 61e. The second belt 62 is formed of an elastically deformable resin material. In addition, the second belt 62 is flexible and includes a sheet-like insert member inside the second belt 62 for suppressing stretching in the longitudinal direction of the second belt 62.

In addition, as illustrated in FIGS. 1 and 2, the second belt 62 includes a plurality of small holes 62a into which the prong 61f is inserted. Additionally, the second belt 62 includes a third hole portion 62b provided at first end portion of the second belt 62 and extending orthogonally to the longitudinal direction of the second belt 62. The third hole portion 62b has an inner diameter at which the spring rod 31b can be inserted into the third hole portion 62b and at which the second belt 62 can rotate with respect to the spring rod 31b. In other words, the second belt 62 is rotatably held by the outer case 31 by disposing the third hole portion 62b between the pair of lugs 31a and around the spring rod 31b.

The second belt 62 is inserted into the frame body 61e, and the prong 61f is inserted into the small hole 62a, and thus the first belt 61 and the second belt 62 are integrally connected together, and the belt 4 as described above, together with the outer case 31, comes to have an annular shape following along the circumferential direction of the wrist 200. By shaping the belt 4 in an annular shape following along the circumferential direction of the wrist 200, the curler 5 is pressed and elastically deformed to follow along the circumferential direction of the wrist of the wearer of the blood pressure measurement device 1.

As illustrated in FIGS. 1 to 4, the curler 5 is configured in a band-like shape that curves in such a manner as to follow along the circumferential direction of the wrist 200. The curler 5 is formed with a first end and a second end spaced apart from each other. For example, a first end side outer surface of the curler 5 is fixed to the rear cover 35 of the device body 3. The curler 5 is disposed at a position where the first end and the second end protrude more to one side of the wrist 200 than the rear cover 35. Accordingly, the curler 5 is disposed with the first end and the second end to one side of the wrist 200 when the blood pressure measurement device 1 is attached to the wrist 200. Furthermore, the first end and the second end of the curler 5 are located adjacent to each other at a predetermined distance from each other. The curler 5 is formed of a resin material, for example. In a specific example, the curler 5 is formed of a polypropylene with a thickness of approximately 1 mm.

In a specific example, as illustrated in FIGS. 1 to 4, the curler 5 is configured in a band-like shape that curves following along the circumferential direction of the wrist. Furthermore, the curler 5 includes the disk-like cover portion 5a provided at a position facing the hand back side of the wrist 200 on the first end side, and constitutes the rear lid together with the rear cover 35, and an escape portion 5b that is provided in the peripheral region of the cover portion 5a and allows the second joining members 35b that fix the outer case 31 and the rear cover 35 to be moveable. For example, the cover portion 5a and the adjacent portion of the cover portion 5a of the curler 5 are formed in a plate-like shape, and the first and second end sides is formed curving with a predetermined curvature more than the cover portion 5a. Furthermore, the length of the curler 5 from the cover portion 5a to the first end is less than the length from the cover portion 5a to the second end. In a specific example, the shorter side of the curler 5 from the cover portion 5a to the first end is disposed on the hand back side of the wrist, and the longer side from the cover portion 5a to the second end extends from the hand back side of the wrist, passing through one side, to the hand palm-side of the wrist 200.

Additionally, as illustrated in FIG. 12, the curler 5 is formed in a shape with the second end located at the inner circumferential surface side of the first end side when the first end and the second end are brought close. In a specific example, the width of the curler 5 in the width direction of the wrist 200 is set to be greater on the hand back side of the wrist 200 than on the hand palm-side of the wrist 200. Furthermore, the radius of curvature of the first end of the curler 5 on the hand back side of the wrist 200 is set to be greater than the radius of curvature of the second end on the hand palm-side of the wrist 200. According to such a configuration, when both end sides of the curler 5 are brought to abut, the second end is disposed further to the inward side of the curler 5 than the first end. Furthermore, the curler 5 is provided with a recess 5c provided adjacent to the cover portion 5a on a portion of the cover portion 5a, on the outer surface on the first end side from the cover portion 5a, and also on the outer surface on the shorter side extending from the cover portion 5a.

The cover portion 5a includes an insert member 5d for reinforcement which is inserted. The cover portion 5a is fixed to the wrist 200 side of the outer case 31 with the fixed rear cover 35 in between. The cover portion 5a includes screw holes 5e provided at positions facing the four hole portions 35c of the rear cover 35, into which the first joining members 35a for fixing the rear cover 35 are screwed, and includes three hole portions 5f for connecting the cuff structure 6 to the device body 3.

The escape portion 5b is a relief for disposing the second joining members 35b in the rear cover 35 and for disposing a tool for rotating the second joining members 35b in a manner so that the second joining members 35b do not interfere with the curler 5 when the rear cover 35 is fixed to the outer case 31 from the rear cover 35 side with the second joining members 35b.

The three hole portions 5f include a first hole portion 5f1 formed with an inner diameter into which a connection portion 84 described below of the pressing cuff 71 can be inserted, a second hole portion 5f2 formed with an inner diameter into which a connection portion 93 described below of the sensing cuff 73 can be inserted, and the third hole portion 5f3 formed with an inner diameter into which the connection portion 103 described below of the tensile cuff 74 can be inserted. In the present embodiment, the second hole portion 5f2 is disposed in the cover portion 5a closer to the second end side on the hand palm-side of the curler 5 than the first hole portion 5f1 and the third hole portion 5f3.

The curler 5 with such a configuration is fixed to the outer case 31 with the first end and the second end orientated to face the second belt 62 of the belt 4. Also, the curler 5 at least at the position facing the hand palm-side of the wrist 200 curves along the circumferential direction along with the hand palm-side of the wrist 200, and thus the cuff structure 6 facing the hand palm-side of the wrist 200 is held in a curved state following along the shape of the hand palm-side of the wrist 200.

The curler 5 has a hardness appropriate to provide flexibility and shape retainability. Here, "flexibility" refers to deformation of the shape of the curler 5 in a radial direction at the time of application of an external force of the belt 4 to the curler 5. For example, "flexibility" refers to deformation of the shape of the curler 5 in a side view in which the curler 5 approaches the wrist, is along the shape of the wrist, or follows to the shape of the wrist when the curler 5 is pressed by the belt 4. Furthermore, "shape retainability" refers to the ability of the curler 5 to maintain a pre-imparted shape when no external force is applied to the curler 5. For example, "shape retainability" refers to, in the present embodiment, the ability of the curler 5 to maintain the shape in a shape curving along the circumferential direction of the wrist.

The cuff structure 6 is disposed on an inner circumferential surface of the curler 5, and is held along the shape of the inner circumferential surface of the curler 5. As a specific example, the cuff structure 6 is held by disposing the pressing cuff 71 and the tensile cuff 74 on the inner circumferential surface of the curler 5, and fixing the cuff structure 6 by a joining layer 75 provided between the curler 5 and the pressing cuff 71 and the tensile cuff 74. In the present embodiment, the joining layer 75 is adhesive or double-sided tape.

As illustrated in FIGS. 1 to 6, 13, and 14, the cuff structure 6 includes the pressing cuff 71, a back plate 72, the sensing cuff 73, and the tensile cuff 74. Also, the cuff structure 6 is provided with the joining layer 75 for joining components each other and joining the curler 5 and the cuffs 71 and 74. The cuff structure 6 is fixed to the curler 5. The cuff structure 6 includes the pressing cuff 71, the back plate 72, and the sensing cuff 73 that are stacked one another and disposed on the curler 5, and the tensile cuff 74 that is spaced apart from the pressing cuff 71, the back plate 72, and the sensing cuff 73 and disposed on the curler 5.

In a specific example, as illustrated in FIG. 4, the cuff structure 6 is fixed to the inner circumferential surface of the curler 5 on the hand palm-side of the wrist 200 with the pressing cuff 71, the back plate 72, and the sensing cuff 73 stacked in this order from the inner circumferential surface of the curler 5 toward the wrist 200 side. In addition, the cuff structure 6 includes the tensile cuff 74 disposed on the inner circumferential surface of the curler 5 on the hand back side of the wrist 200. Each of the members of the cuff structure 6 is fixed to an adjacent member of the cuff structure 6 in a stacking direction by the joining layer 75.

The pressing cuff 71 is fluidly connected to the pump 14 through the flow path portion 15. The pressing cuff 71 is inflated to pressing the back plate 72 and the sensing cuff 73 toward the wrist 200 side. As illustrated in FIGS. 8, 9, and 13 to 16, the pressing cuff 71 includes a plurality of, for example, two-layer air bags 81, a target join portion 82 provided on the air bag 81 facing the curler 5, a flow path body (first flow path body) 83 communicating with air bags 81, and the connection portion (first connection portion) 84 provided in the leading end of the flow path body 83. The pressing cuff 71 with such a configuration is configured by integrally welding a plurality of sheet members 86 together.

Here, the air bags 81 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. The plurality of air bags 81 are stacked and are in fluid communication with one another in the stacking direction.

Each of the air bags 81 is formed in a rectangular bag-like shape that is long in one direction. Additionally, the air bags 81 are set so that the width in the lateral direction is the same as the width in the lateral direction of the curler 5. The air bags 81 are each constituted by, for example, combining two sheet members 86 and, as illustrated in FIGS. 8 and 13 to 16, welding a weld portion 81a using heat into a rectangular frame shape long in one direction. In addition, the two-layer air bags 81 are constituted by forming with integrally combining two air bags 81 by welding using heat, or with welding together a pair of sheet members 86 facing adjacent air bag 81 and welding to the air bag 81. In a specific example, the two-layer air bags 81 are fluidly continuous through openings provided in the sheet members 86 facing one another. In addition, in the two-layer air bags 81, by bridge welding the opposing sheet members 86 together with a quadrilateral frame shape smaller than the weld portion 81a located on the outer peripheral edge and surrounding the plurality of openings with this bridge weld portion (join portion) 81b, the adjacent air bags 81 are integrally formed and make fluidly continuous on the inner side of the bridge weld portion 81b. Here, bridge in bridge welding and the bridge weld portion means integrally joining adjacent air bags 81.

A single or a plurality of target join portions 82 are provided at at least a portion of the edge portion of the air bag 81 disposed adjacent to the curler 5. The target join portion 82 is formed by a portion of the sheet member 86 forming the air bag 81.

An example of the present embodiment will be described using the examples illustrated in FIGS. 7 to 9 and 13 to 15 in which one target join portion 82 is provided on the edge portion in the lateral direction of each of the air bags 81.

Note that, for example, the target join portion 82 may be divided in the longitudinal direction of the air bag 81 by a slit, or a plurality of target join portions 82 may be provided in the longitudinal direction of the air bag 81. The target join portion 82 is at least joined to the outer circumferential surface of the curler 5 when the pressing cuff 71 is disposed on the inner circumferential surface of the curler 5. Furthermore, for example, two target join portions 82 are stacked and welded.

Note that the two target join portions 82 are set to have a different length to the length in the lateral direction of the air bags 81, for example. In this example, the two target join portions 82 are stacked and welded at the first end side in the lateral direction of the curler 5. Note that as long as the two target join portions 82 are able to be disposed with the leading end on the outer circumferential surface of the curler 5, the length is able to be set as appropriate, and the two target join portions 82 may be stackable or not. However, in a case where the length is set to a stackable length, the length is preferably a length such that the leading end does not extend further out than the outer edge of the outer circumferential surface of the curler 5.

As illustrated in FIGS. 7 and 13 to 17, the flow path body 83 is integrally provided on a single air bag 81, for example, on a portion of one edge portion in the longitudinal direction of the air bag 81 adjacent to the curler 5. As a specific example, the flow path body 83 is provided at the end portion of the air bag 81 near the device body 3. Additionally, the flow path body 83 is formed in a shape that is long in one direction and has less width than the width of the air bag 81 in the lateral direction and formed with a leading end having a circular shape. The flow path body 83 includes the connection portion 84 on the leading end. The flow path body 83 is connected to the flow path portion 15 through the connection portion 84 and constitutes a flow path between the flow path portion 15 of the device body 3 and the air bag 81.

The flow path body 83 is constituted by welding a portion of sheet members 86, which is adjacent to a region of the sheet members 86 constituting the air bags 81, in a frame shape long in one direction using heat, in a state where the connection portion 84 is disposed on the two sheet members 86. The flow path body 83 with such a configuration is disposed between the inner circumferential surface of the curler 5 and the tensile cuff 74, and the leading end is disposed at a position facing the first hole portion 5/1 on the main surface on the wrist 200 side of the region where the cover portion 5a of the curler 5 is provided.

Note that, a portion of the weld portion 81a, where the two sheet members 86 are welded in a rectangular frame shape, is not welded and the air bags 81 provided with the flow path body 83 are constituted to be continuous with the weld portion 83a constituting the flow path body 83, and thus the air bags 81 are fluidly continuous with the flow path body 83.

The connection portion 84 is, for example, a nipple. The connection portion 84 is provided at the leading end of the flow path body 83. The leading end of the connection portion 84 is exposed from the sheet member 86, facing the curler 5, of the two sheet members 86 constituting the flow path body 83. The connection portion 84 is inserted in the first hole portion 5/1 of the cover portion 5a and is connected to the flow path portion 15.

As a specific example, as illustrated in FIGS. 8, 9, and 45, the pressing cuff 71 includes a first sheet member 86a, a second sheet member 86b, a third sheet member 86c, and a fourth sheet member 86d in this order from the wrist 200 side. The second sheet member 86b constitutes a first-layer air bag 81 along with the first sheet member 86a, the third sheet member 86c is integrally joined to the second sheet member 86b and constitutes the target join portion 82, and the fourth sheet member 86d constitutes a second-layer air bag 81 and the flow path body 83 along with the third sheet member 86c. Note that the pressing cuff 71 is integrally constituted by joining adjacent sheet members 86 by welding using heat.

The first sheet member 86a and the second sheet member 86b are configured in a similar rectangular shape to the air bags 81, and peripheral edge portions of the four sides are welded to constitute the air bags 81. The second sheet member 86b and the third sheet member 86c are disposed facing each other, and each includes a plurality of openings 86b1 and 86c1 through which the two air bags 81 are fluidly continuous. Additionally, the second sheet member 86b and the third sheet member 86c are integrally joined by the peripheral region of the plurality of openings 86b1 and 86c1 being bridge welded using heat in a quadrilateral frame shape smaller than the welded four sides of the air bags 81.

The third sheet member 86c, for example, is constituted in a shape that allows the air bags 81, the target join portion 82, and the flow path body 83 to be constituted. The fourth sheet member 86d, for example, is constituted in a shape that allows the air bags 81 and the flow path body 83 to be constituted. Furthermore, the fourth sheet member 86d includes a hole portion 86d1 into which the leading end of the connection portion 84 can be inserted, for example.

The air bags 81, the target join portion 82, and the flow path body 83 are constituted by the third sheet member 86c and the fourth sheet member 86d being disposed facing one another, welded using heat along the peripheral edge shape of the air bag 81 and the flow path body 83 so that the air bag 81 and the flow path body 83 are fluidly continuous, and cut in a predetermined shape.

The hole portion 86d1 of the fourth sheet member 86d is disposed with the connection portion 84, and the peripheral region of the hole portion 86d1 is welded to the connection portion 84 using heat. Furthermore, the fourth sheet member 86d is joined with the inner circumferential surface of the curler 5 with the joining layer 75 in between, and the target join portion 82 of the third sheet member 86c is joined to the outer circumferential surface of the curler 5 with the joining layer 75 in between.

As illustrated in FIGS. 8, 9 and 45, the back plate 72 is applied to the outer surface of the first sheet member 86a of the pressing cuff 71 by the joining layer 75. The back plate 72 is formed in a plate shape using a resin material. The back plate 72 is made of polypropylene, for example, and is formed into a plate shape having a thickness of approximately 1 mm. The back plate 72 has shape followability.

Here, "shape followability" refers to a function of the backplate 72 by which the back plate 72 can be deformed in such a manner as to follow the shape of a contacted portion of the wrist 200 to be disposed, the contacted portion of the wrist 200 refers to a region of the wrist 200 that is faced by the back plate 72. Here, the contact as used herein includes both direct contact and indirect contact with the sensing cuff 73 in between.

For example, as illustrated in FIG. 9, the back plate 72 includes a plurality of grooves 72a extending in both main surfaces of the back plate 72 in a direction orthogonal to the longitudinal direction. The plurality of grooves 72a face the corresponding grooves 72a provided in the other main surface in the thickness direction of the back plate 72.

Additionally, the plurality of grooves 72*a* are disposed at equal intervals in the longitudinal direction of the back plate 72.

In the back plate 72, portions including the plurality of grooves 72*a* are thinner than portions including no grooves 72*a* and thus the portions including the plurality of grooves 72*a* are easily deformed. Accordingly, the back plate 72 is deformed in such a manner as to follow to the shape of the wrist 200, and has shape followability of extending in the circumferential direction of the wrist. The back plate 72 is formed such that the length of the back plate 72 is sufficient to cover the hand palm-side of the wrist 200. The back plate 72 transfers the pressing force from the pressing cuff 71 to the back plate 72 side main surface of the sensing cuff 73 in a state in which the back plate 72 is extending along the shape of the wrist 200.

The sensing cuff 73 is fluidly connected to the pump 14 through the flow path portion 15. The sensing cuff 73 is fixed to the main surface of the back plate 72 on the wrist 200 side. The sensing cuff 73 is in direct contact with a region of the wrist 200 where an artery 210 resides, as illustrated in FIGS. 4 and 45. The artery 210 as used herein is the radial artery and the ulnar artery. The sensing cuff 73 is formed in the same shape as that of the back plate 72 or a shape that is smaller than that of the back plate 72, in the longitudinal direction and the width direction of the back plate 72. The sensing cuff 73 is inflated to compress a hand palm-side region of the wrist 200 in which the artery 210 resides. The sensing cuff 73 is pressed by the inflated pressing cuff 71 toward the wrist 200 side with the back plate 72 in between.

In a specific example, as illustrated in FIGS. 8, 9, 13, 14, 17, and 18, the sensing cuff 73 includes one air bag 91, a flow path body (second flow path body) 92 that communicates with the air bag 91, and the connection portion 93 provided at the leading end in the flow path body 92. One main surface of the air bag 91 of the sensing cuff 73 is fixed to the back plate 72. For example, the sensing cuff 73 is joined to the main surface of the back plate 72 on the wrist 200 side by the joining layer 75. The sensing cuff 73 with such a configuration is constituted by welding two sheet members 96.

Here, the air bag 91 is a bag-like structure, and in the present embodiment, the blood pressure measurement device 1 is configured to use air with the pump 14, and thus the present embodiment will be described using the air bag. However, in a case where a fluid other than air is used, the bag-like structure may be a fluid bag and the like.

The air bag 91 is constituted in a rectangular shape that is long in one direction. The air bags 91 are each constituted by, for example, combining two sheet members 96 long in one direction and, as illustrated in FIGS. 8, 9, 13, 14, 17, and 18, welding a weld portion 91*a* using heat into a rectangular frame shape long in one direction. Also, the air bag 91, for example, includes a junction margin 91*b* for ensuring area for joining the air bag 91 to the back plate 72 using the joining layer 75. The junction margin 91*b* is formed by the sheet member 96 facing the back plate 72, for example.

The flow path body 92 is integrally provided at a portion of one edge portion of the air bag 91 in the longitudinal direction. As a specific example, the flow path body 92 is provided at the end portion of the air bag 91 near the device body 3. Additionally, the flow path body 92 is formed in a shape that is long in one direction and has less width than the width of the air bag 91 in the lateral direction, and formed with a leading end having a circular shape. The flow path body 92 includes the connection portion 93 on the leading end. The flow path body 92 is connected to the flow path portion 15 through the connection portion 93 and constitutes a flow path between the flow path portion 15 of the device body 3 and the air bag 91.

The flow path body 92 is constituted by welding a portion of sheet members 96, which is adjacent to a region of the sheet members 96 constituting the air bag 91, in a frame shape long in one direction using heat, in a state where the connection portion 93 is disposed on the two sheet members 96. Note that, a portion of the weld portion 91*a*, where the two sheet members 96 are welded in a rectangular frame shape, is not welded and the air bag 91 is constituted to be continuous with the weld portion 92*a* constituting the flow path body 92, and thus the air bag 91 and the flow path body 92 are fluidly continuous. The flow path body 92 with such a configuration is disposed between the inner circumferential surface of the curler 5 and the tensile cuff 74, and the leading end is disposed at a position facing the second hole portion 5*f*2 on the main surface on the wrist 200 side of the region where the cover portion 5*a* of the curler 5 is provided.

The connection portion 93 is, for example, a nipple. The connection portion 93 is provided at the leading end of the flow path body 92. Also, the leading end of the connection portion 93 is externally exposed from the sheet member 96 facing the curler 5 and the back plate 72, of the two sheet members 96 constituting the flow path body 92. The connection portion 93 is inserted in the second hole portion 5*f*2 of the cover portion 5*a* and is connected to the flow path portion 15.

In a specific example, the sensing cuff 73 includes a fifth sheet member 96*a* and a sixth sheet member 96*b* in this order from the wrist 200 side as illustrated in FIGS. 8 and 9. Note that the sensing cuff 73 is constituted by joining adjacent sheet members 96 by welding using heat.

For example, the fifth sheet member 96*a* and the sixth sheet member 96*b* are constituted in a shape that allows the air bag 91, the junction margin 91*b*, and the flow path body 92 to be constituted. The air bag 91 and the flow path body 92 are constituted by the fifth sheet member 96*a* and the sixth sheet member 96*b* being disposed facing one another, welded using heat along the peripheral edge shape of the air bag 91 and the flow path body 92 so that the air bag 91 and the flow path body 92 are fluidly continuous, and cut in a predetermined shape.

Furthermore, the sixth sheet member 96*b* includes a hole portion 96*b*1 into which the leading end of the connection portion 93 can be inserted, for example. The connection portion 93 is disposed in the hole portion 96*b*1, and the peripheral region of the hole portion 96*b*1 is welded to the connection portion 93 using heat. The sixth sheet member 96*b* is joined to the inner circumferential surface of the back plate 72 with the joining layer 75 in between.

The tensile cuff 74 is fluidly connected to the pump 14 through the flow path portion 15. As illustrated in FIG. 4, the tensile cuff 74 is inflated to press the curler 5 such that the curler 5 is spaced apart from the wrist 200, pulling the belt 4 and the curler 5 toward the hand back side of the wrist 200. As illustrated in FIGS. 10, 11, 19, and 20, the tensile cuff 74 includes a plurality of, for example, six-layer air bags 101, a target join portion 102 provided on the air bag 101 facing the curler 5, the connection portion (third connection portion) 103 provided on the air bag 101 facing the curler 5, and a cutout portion 104 provided on at least the air bag 101 facing the curler 5. The tensile cuff 74 with such a configuration is constituted by welding a plurality of sheet members 106. In addition, the tensile cuff 74 is fixed to the region where the flow path bodies 83 and 92 are provided and the curler 5, including the cover portion 5*a*, on the hand back side of the wrist 200. In other words, the flow path body 83 of the pressing cuff 71 and the flow path body 92 of the sensing cuff 73 are disposed between the curler 5 on the hand back side of the wrist 200 and the tensile cuff 74.

Additionally, the tensile cuff 74 is configured such that the thickness of the tensile cuff 74 in an inflating direction, in the present embodiment, in the direction in which the curler 5 and the wrist 200 face each other, during inflation, is larger than the thickness of the pressing cuff 71 in the inflating direction during inflation and than the thickness of the sensing cuff 73 in the inflating direction during inflation. Specifically, the air bags 101 of the tensile cuff 74 include more layer structures than the air bags 81 in the pressing cuff 71 and the air bag 91 in the sensing cuff 73, and have thicker thickness than the pressing cuff 71 and the sensing cuff 73 when the air bags 101 are inflated from the curler 5 toward the wrist 200.

As illustrated in FIGS. 10, 11, and 20, in the present embodiment, the tensile cuff 74 including the six-layer air bags 101 includes a first outer layer 111 constituted by one air bag 101, a first intermediate layer 112 constituted by two air bags 101 integrally combining with the first outer layer 111 by welding using heat, a second intermediate layer 113 constituted by two-layer air bags 101 integrally combining with the first intermediate layer 112 by welding using heat, and a second outer layer 114 constituted by one air bag 101 integrally combining with the second intermediate layer 113 by welding using heat.

Here, the air bags 101 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. A plurality of the air bags 101 are stacked and are in fluid communication in the stacking direction.

Each of the air bags 101 is formed in a rectangular bag-like shape that is long in one direction. Additionally, the air bags 101 are set so that the width in the lateral direction is the same as the width in the lateral direction of the curler 5. The air bags 101 are each constituted by, for example, combining two sheet members 106 and, as illustrated in FIGS. 10, 11, 13, 14, 19, and 20, welding a weld portion 101a using heat into a rectangular frame shape long in one direction. The six-layer air bags 101 are fluidly continuous through openings provided in the sheet members 106 facing one another.

In addition, in the six-layer air bags 101, for the first outer layer 111 and the first intermediate layer 112, the first intermediate layer 112 and the second intermediate layer 113, and the second intermediate layer 113 and the second outer layer 114, by bridge welding the opposing sheet members 106 together with a quadrilateral frame shape smaller than the weld portion 81a located on the outer peripheral edge and surrounding the plurality of openings with the bridge weld portion (join portion) 101b, the adjacent air bags 101 are integrally formed and made fluidly continuous on the inner side of the bridge weld portion 101b.

The first outer layer 111 is formed by one air bag 101 disposed on the wrist 200 side. The first outer layer 111 constitutes the first air bag 101 of the six-layer air bags 101 from the wrist 200 side.

The first intermediate layer 112 is stacked on the first outer layer 111. The first intermediate layer 112 is formed by two-layer air bags 101. The first intermediate layer 112 constitutes the second and third air bags 101 of the six-layer air bags 101 from the wrist 200 side. The first intermediate layer 112 is constituted by two-layer air bags 101 integrally welded at the outer peripheral edge. In other words, the first intermediate layer 112 is formed by integrally welding four sheet members 106 in the outer peripheral edge shape of the air bags 101.

The second intermediate layer 113 is stacked on the first intermediate layer 112. The second intermediate layer 113 is formed by two-layer air bags 101. The second intermediate layer 113 constitutes the fourth and fifth air bags 101 of the six-layer air bags 101 from the wrist 200 side. The second intermediate layer 113 is constituted by two-layer air bags 101 integrally welded at the outer peripheral edge. In other words, the second intermediate layer 113 is formed by integrally welding four sheet members 106 in the outer peripheral edge shape of the air bags 101.

The second outer layer 114 is formed by one air bag 101 disposed on the curler 5 side. The second outer layer 114 constitutes the sixth air bag 101 of the six-layer air bags 101 from the wrist 200 side.

A single or a plurality of target join portions 102 are provided at at least a portion of the edge portion of the air bag (the sixth air bag) 101 disposed adjacent to the curler 5. The target join portion 102 is formed by a portion of the sheet member 106 forming the air bag 101.

An example of the present embodiment will be described using examples in which two target join portions 102 are each provided in the longitudinal direction of the air bags 101 on the edge portion in the lateral direction of each of the air bags 101. Note that, for example, the target join portions 102 are provided on the air bags 101 avoiding the positions facing the cover portion 5a of the curler 5. Furthermore, for example, the target join portion 102 includes an escape portion 102a, which is for externally exposing a power feeding terminal 8b described below of the power feeding unit 8 provided on the curler 5, at a portion facing the power feeding terminal 8b. The escape portion 102a, for example, is an opening through which the power feeding terminal 8b can be externally exposed and has a circular shape as an example.

The target join portion 102 is at least joined to the outer circumferential surface of the curler 5 when the tensile cuff 74 is disposed on the inner circumferential surface of the curler 5. Additionally, the target join portions 102 disposed at the same position in the lateral direction of the air bags 101 are stacked and welded.

Note that the two target join portions 102 are set to have a different length to the length in the lateral direction of the air bags 101, for example. In this example, the two target join portions 102 are stacked and welded at the first end side in the lateral direction of the curler 5. Note that as long as the two target join portions 102 are able to be disposed with the leading end on the outer circumferential surface of the curler 5, the length is able to be set as appropriate and the two target join portions 102 may be stackable or not. However, in a case where the length is set to a stackable length, the length is preferably a length such that the leading end does not extend further out than the outer edge of the outer circumferential surface of the curler 5.

The connection portion 103 is, for example, a nipple. The connection portion 103 is provided at a position facing the third hole portion 5f3 of the cover portion 5a in a central region in the longitudinal direction of the air bag 101 disposed adjacent to the curler 5. The leading end of the connection portion 103 is exposed from the sheet member 106 facing the curler 5, of the two sheet members 106 forming the air bag 101. The connection portion 103 is inserted in the third hole portion 5f3 of the cover portion 5a and is connected to the flow path portion 15.

As illustrated in FIG. 19, the cutout portion 104 is provided at a position facing the escape portion 5b provided on the curler 5. The cutout portion 104 is provided on the sixth air bag 101 forming the second outer layer 114.

In a specific example, as illustrated in FIGS. 10, 11, and 20, the tensile cuff 74 includes a seventh sheet member 106a, an eighth sheet member 106b, a ninth sheet member 106c, a tenth sheet member 106d, an eleventh sheet member 106e, a twelfth sheet member 106f, a thirteenth sheet member 106g, a fourteenth sheet member 106h, a fifteenth sheet member 106i, a sixteenth sheet member 106j, a seventeenth sheet member 106k, and an eighteenth sheet member 106l in this order from the wrist 200 side. Note that the tensile cuff 74 is integrally constituted by joining adjacent sheet members 106 by welding using heat.

The seventh sheet member 106a to the eighteenth sheet member 106l are constituted in a similar rectangular shape to the air bags 101. The seventh sheet member 106a and the eighth sheet member 106b are welded using heat along the peripheral edge portion shape on the four sides of the air bags 101 to constitute the first (first layer) air bag 101 from the wrist 200 side. In other words, the seventh sheet member 106a and the eighth sheet member 106b constitute the first outer layer 111.

The eighth sheet member 106b and the ninth sheet member 106c are disposed facing each other, and each includes a plurality of openings 106b1 and 106c1 through which the two air bags 101 are fluidly continuous. Additionally, the eighth sheet member 106b and the ninth sheet member 106c are integrally joined by the peripheral region of the plurality of openings 106b1 and 106c1 being bridge welded using heat in a quadrilateral frame shape smaller than the welded four sides of the air bags 101.

The ninth sheet member 106c and the tenth sheet member 106d are welded using heat along the peripheral edge portion shape on the four sides of the air bags 101 to constitute the second (second layer) air bag 101 from the wrist 200 side.

As illustrated in FIGS. 10, 11, and 20, the tenth sheet member 106d and the eleventh sheet member 106e include a plurality of openings 106d1 and 106e1 disposed facing one another and through which the two air bags 101 are fluidly continuous. The eleventh sheet member 106e and the twelfth sheet member 106f are welded using heat along the peripheral edge portion shape on the four sides of the air bags 101 to constitute the third (third layer) air bag 101 from the wrist 200 side.

The ninth sheet member 106c, the tenth sheet member 106d, the eleventh sheet member 106e, and the twelfth sheet member 106f are integrally welded using heat along the peripheral edge portion shape on the four sides of the air bags 101 to constitute the first intermediate layer 112 in which the second and third air bags 101 are integrally formed.

As illustrated in FIGS. 10, 11, and 20, the twelfth sheet member 106f and the thirteenth sheet member 106g include a plurality of openings 106f1 and 106g1 disposed facing one another and through which the two air bags 101 are fluidly continuous. Additionally, the twelfth sheet member 106f and the thirteenth sheet member 106g are integrally joined by the peripheral region of the plurality of openings 106f1 and 106g1 being bridge welded using heat in a quadrilateral frame shape smaller than the welded four sides of the air bags 101.

The thirteenth sheet member 106g and the fourteenth sheet member 106h are welded using heat along the peripheral edge portion shape on the four sides of the air bags 101 to constitute the fourth (fourth layer) air bag 101 from the wrist 200 side.

As illustrated in FIGS. 10, 11, and 20, the fourteenth sheet member 106h and the fifteenth sheet member 106i include a plurality of openings 106h1 and 106i1 disposed facing one another and through which the two air bags 101 are fluidly continuous. The fifteenth sheet member 106i and the sixteenth sheet member 106j are welded using heat along the peripheral edge portion shape on the four sides of the air bags 101 to constitute the fifth (fifth layer) air bag 101 from the wrist 200 side.

The thirteenth sheet member 106g, the fourteenth sheet member 106h, the fifteenth sheet member 106i, and the sixteenth sheet member 106j are integrally welded using heat along the peripheral edge portion shape on the four sides of the air bags 101 to constitute the second intermediate layer 113 in which the fourth and fifth air bags 101 are integrally formed.

As illustrated in FIGS. 10, 11, and 20, the sixteenth sheet member 106j and the seventeenth sheet member 106k include a plurality of openings 106j1 and 106k1 disposed facing one another and through which the two air bags 101 are fluidly continuous. Also, the seventeenth sheet member 106k, for example, is constituted in a shape that allows the air bag 101 and the target join portion 102 to be constituted. Additionally, the sixteenth sheet member 106j and the seventeenth sheet member 106k are integrally joined by the peripheral region of the plurality of openings 106j1 and 106k1 being bridge welded using heat in a quadrilateral frame shape smaller than the welded four sides of the air bags 101.

The seventeenth sheet member 106k and the eighteenth sheet member 106l are welded using heat along the peripheral edge portion shape on the four sides of the air bag 101 and cut in a predetermined shape to constitute the sixth air bag 101 from the wrist 200 side, which includes the cutout portion 104, and the target join portion 102.

Furthermore, the eighteenth sheet member 106l includes a hole portion 106l1 into which the leading end of the connection portion 103 can be inserted, for example. The eighteenth sheet member 106l is disposed with the connection portion 103 at the hole portion 106l1, and the peripheral region of the hole portion 106l1 is welded to the connection portion 103 using heat. Furthermore, the eighteenth sheet member 106l is joined with the inner circumferential surface of the curler 5 with the joining layer 75 in between, and the target join portion 102 of the seventeenth sheet member 106k is joined to the outer circumferential surface of the curler 5 with the joining layer 75 in between.

Additionally, each of the sheet members 86, 96, and 106 forming the pressing cuff 71, the sensing cuff 73, and the tensile cuff 74 are formed with a thickness of 0.15 mm, for example. Additionally, each of the sheet members 86, 96, and 106 are formed of a thermoplastic resin material. The thermoplastic resin material is a thermoplastic elastomer. Examples of thermoplastic resin material constituting the sheet members 86, 96, and 106 include thermoplastic polyurethane based resin (hereinafter referred to as TPU), polyvinyl chloride resin, ethylene-vinyl acetate resin, thermoplastic polystyrene based resin, thermoplastic polyolefin resin, thermoplastic polyester based resin, and thermoplastic polyamide resin. Note that, in the pressing cuff 71 and the sensing cuff 73, of at least the plurality of sheet members 86 and 106 constituting the air bags 81 and 101, at least the sheet members 86 and 106 welded to the curler 5 are constituted by a material similar to the material of the curler 5.

For example, the sheet members 86, 96, and 106 are formed using a molding method such as T-die extrusion molding or injection molding. After being molded by each molding method, the sheet members 86, 96, and 106 are sized into predetermined shapes, and the sized individual pieces are joined by welding or the like to constitute bag-like structures 81, 91, and 101. A high frequency welder or laser welding is used as the welding method.

The fluid circuit 7 is constituted by the case 11, the pump 14, the flow path portion 15, the on-off valves 16, the pressure sensors 17, the pressing cuff 71, the sensing cuff 73, and the tensile cuff 74. A specific example of the fluid circuit 7 will be described below.

As illustrated in FIG. 5, for example, the fluid circuit 7 includes a first flow path 7a in which the pump 14, the sensing cuff 73, the first pressure sensor 17A and the second pressure sensor 17B are continuous through the first on-off valve 16A, a second flow path 7b which is constituted by branching from the first flow path 7a between the pump 14 and the first on-off valve 16A and is continuous from the pump 14 to the atmosphere through the second on-off valve 16B, the third on-off valve 16C, and the fourth on-off valve 16D sequentially in this order, a third flow path 7c which is constituted by branching from an intermediate portion of the second flow path 7b between the second on-off valve 16B and the third on-off valve 16C and is continuous from the pump 14 to the tensile cuff 74, and a fourth flow path 7d which is constituted by branching from an intermediate portion of the second flow path 7b between the third on-off valve 16C and the fourth on-off valve 16D and is continuous from the pump 14 to the pressing cuff 71.

In the fluid circuit 7 with such a configuration, by the second on-off valve 16B and the third on-off valve 16C being open and the first on-off valve 16A and the fourth on-off valve 16D being closed, the third flow path 7c and the fourth flow path 7d branching from the second flow path 7b are connected to the pump 14, and the pump 14, the pressing cuff 71, and the tensile cuff 74 are fluidly connected.

In the fluid circuit 7, by the first on-off valve 16A, the second on-off valve 16B, and the third on-off valve 16C being open and the fourth on-off valve 16D being closed, the first flow path 7a and the third flow path 7c and the fourth flow path 7d branching from the second flow path 7b are connected to the pump 14, and the pump 14, the pressing cuff 71, and the tensile cuff 74 and the pump 14 and the sensing cuff 73 are fluidly connected. In the fluid circuit 7, by the second on-off valve 16B, the third on-off valve 16C, and the fourth on-off valve 16D being open and the first on-off valve 16A being closed, the second flow path 7b, the third flow path 7c, and the fourth flow path 7d are connected to the pump 14, and the pump 14, the pressing cuff 71, the tensile cuff 74, and the atmosphere are fluidly connected. In the fluid circuit 7, by the first on-off valve 16A, the second on-off valve 16B, the third on-off valve 16C, and the fourth on-off valve 16D being open, the first flow path 7a, the second flow path 7b, the third flow path 7c, and the fourth flow path 7d are connected to the pump 14, and the pump 14, the pressing cuff 71, the sensing cuff 73, the tensile cuff 74, and the atmosphere are fluidly connected.

As illustrated in FIGS. 6 and 7, the power feeding unit 8 is provided in the recess 5c formed in the outer surface of the curler 5 on the first end side that projects from the device body 3. For example, the power feeding unit 8 is configured to be capable to connect to a connector provided on a charging cable of a charger.

As illustrated in FIGS. 3, 6, and 7, the power feeding unit 8 is provided with a wiring portion 8a, the power feeding terminal 8b, and a cover 8c that covers the wiring portion 8a disposed in the recess 5c of the curler 5. The first end of the wiring portion 8a is connected to the power feeding terminal 8b, and the second end is connected to the control unit 55. The power feeding terminal 8b is constituted by two circular terminals, for example. For example, the wiring portion 8a and the power feeding terminal 8b are formed of flexible printed circuits (FPC) and the like including a base film, such as polyimide, provided with an electrically conductive metal film and the like. The cover 8c is formed in the same shape as the recess 5c and covering the recess 5c, and the upper surface runs flush with the outer surface of the curler 5 on the shorter side when the cover 8c is provided in the recess 5c.

Next, an example of a method for manufacturing the blood pressure measurement device 1 will be described using FIGS. 21 to 40.

First, as illustrated in FIG. 21, an example of the method for manufacturing the pressing cuff 71 will be described.

A material is cut (step ST11) to form the sheet members 86 in a predetermined shape. In a specific example, the material is punched out into the sheet members 86a, 86b, 86c, and 86d having a predetermined shape by a pressing machine. Here, the predetermined shape is a shape including the air bags 81, the flow path body 83, and the target join portion 82, as well as welding margin, a dummy portion for alignment in aligning at each of the processing machines, and the like.

Next, the connection portion 84 is welded to the fourth sheet member 86d being cut (step ST12). In a specific example, the connection portion 84 is inserted in the hole portion 86d1 provided on the leading end of the portion constituting the flow path body 83 of the fourth sheet member 86d and the connection portion 84 is welded to the fourth sheet member 86d using a high frequency welding machine.

Next, the sheet members 86a, 86b, 86c, and 86d are integrally welded (step ST13). In a specific example, first, the second sheet member 86b and the third sheet member 86c are sequentially set at a positioning pin of a jig, thus the third sheet member 86c is disposed stacking on top of the second sheet member 86b. Next, the bridge weld portion 81b is formed by welding in a rectangular frame shape using the high frequency welding machine as surrounding around the opening 86b1 and 86c1 of the sheet members 86b and 86c, and the sheet members 86b and 86c are integrally welded. Next, an intermediate electrode is disposed between the welded sheet members 86b and 86c. Then, the first sheet member 86a on the wrist 200 side, the sheet members 86b and 86c disposed with the intermediate electrode, and the fourth sheet member 86d with the connection portion 84 welded thereto are sequentially set at the positioning pin of the jig, thus the sheet members 86a, 86b, 86c, and 86d are disposed stacking on one another. Then, the weld portion 81a is formed by the sheet members 86a, 86b, 86c, and 86d being welded to the peripheral shape of the pressing cuff 71 using the high frequency welding machine, and the sheet members 86a, 86b, 86c, and 86d are integrally welded. In this manner, the air bags 81 and the flow path body 83 are formed.

Next, the target join portion 82 is formed (step ST14). In a specific example, the sheet members 86a, 86b, 86c, and

86*d* welded integrally are set at the positioning pin of the jig and punched out into the shape of the target join portion 82 by a press machine. Next, the sheet members 86*a*, 86*b*, 86*c*, and 86*d* welded integrally are finishing cut (step ST15), and the sheet members 86*a*, 86*b*, 86*c*, and 86*d* welded integrally are formed in the external shape of the pressing cuff 71. In a specific example, the sheet members 86*a*, 86*b*, 86*c*, and 86*d* welded integrally are set at the positioning pin of the jig and punched out into the shape of the pressing cuff 71 by a press machine. Next, information such as a lot number is printed on a prescribed location on the manufactured pressing cuff 71 (step ST16).

Next, as illustrated in FIG. 22, an example of the method for manufacturing the sensing cuff 73 will be described.

A material is cut (step ST21) to form the sheet members 96 in a predetermined shape. In a specific example, the material is punched out into the sheet members 96*a* and 96*b* having a predetermined shape by a press machine. Here, the predetermined shape is a shape including the air bag 91 and the flow path body 92, as well as welding margin, a dummy portion for alignment in aligning at each of the processing machines, and the like.

Next, the connection portion 93 is welded to the sixth sheet member 96*b* being cut (step ST22). In a specific example, the connection portion 93 is inserted in the hole portion 96*b*1 provided on the leading end of the portion constituting the flow path body 92 of the sixth sheet member 96*b* and the connection portion 93 is welded to the sixth sheet member 96*b* using a high frequency welding machine.

Next, the two sheet members 96*a* and 96*b* are integrally welded (step ST23). In a specific example, the fifth sheet member 96*a* and the sixth sheet member 96*b* are sequentially set at a positioning pin of a jig, thus the sixth sheet member 96*b* is disposed stacking on top of the fifth sheet member 96*a*. Then, the weld portion 91*a* is formed by the sheet members 96*a* and 96*b* being welded to the peripheral shape of the sensing cuff 73 using the high frequency welding machine, and the sheet members 96*a* and 96*b* are integrally welded. In this manner, the air bag 91 and the flow path body 92 are formed.

Next, the sheet members 96*a* and 96*b* integrally welded are finishing cut into the external shape of the sensing cuff 73 (step ST24). In a specific example, the sheet members 96*a* and 96*b* welded integrally are set at the positioning pin of the jig and punched out into the shape of the sensing cuff 73 by a press machine. Next, information such as a lot number is printed on a prescribed location on the manufactured sensing cuff 73 (step ST25).

Next, as illustrated in FIGS. 23 to 39, a method for manufacturing the tensile cuff 74 will be described.

A material is cut (step ST31) to form the sheet members 106 in a predetermined shape. Here, the predetermined shape is a shape including the air bags 101 and the target join portion 102, as well as welding margin, a dummy portion for alignment in aligning at each of the processing machines, and the like. In a specific example, as illustrated in FIGS. 24 to 27, a first sheet 106A, a second sheet 106B, a third sheet 106C, and a fourth sheet 106D are each punched out by a press machine from a sheet-like material formed of a thermoplastic resin material.

The first sheet 106A includes a positioning pin hole 311 into which a positioning pin 301 can be inserted, and is a sheet member with a rectangular shape larger than the outer peripheral edge shape of the air bags 101. The first sheet 106A forms the seventh sheet member 106*a*.

The second sheet 106B includes the positioning pin hole 311 into which a positioning pin 301 can be inserted and an opening through which the adjacent air bag 101 is fluidly connected, and is a sheet member with a rectangular shape larger than the outer peripheral edge shape of the air bags 101. The second sheet 106B forms the eighth sheet member 106*b*, the ninth sheet member 106*c*, the tenth sheet member 106*d*, the eleventh sheet member 106*e*, the twelfth sheet member 106*f*, the thirteenth sheet member 106*g*, the fourteenth sheet member 106*h*, the fifteenth sheet member 106*i*, and the sixteenth sheet member 106*j*. In addition, here, the opening of the second sheet 106B constitutes one of the openings 106*b*1 to 106*j*1 of the eighth sheet member 106*b* to the sixteenth sheet member 106*j*.

The third sheet 106C includes the positioning pin hole 311 into which a positioning pin 301 can be inserted and an opening through which the adjacent air bag 101 is fluidly connected, and is a sheet member with a rectangular shape larger than the outer peripheral edge shape of the air bags 101 and the target join portion 102. The third sheet 106C forms the seventeenth sheet member 106*k*. The fourth sheet 106D includes a positioning pin hole 311, into which a positioning pin 301 can be inserted, and the hole portion 106*l*1, into which the connection portion 103 is inserted, and is a sheet member with a rectangular shape larger than the outer peripheral edge shape of the air bags 101.

Next, the connection portion 103 is welded to the fourth sheet 106D (step ST32). In a specific example, the connection portion 103 is inserted in the hole portion 106*l*1 provided in a central region of the fourth sheet 106D and the connection portion 103 is welded to the fourth sheet 106D using a high frequency welding machine.

Next, as illustrated in FIGS. 28 to 31, the two sets of the two second sheets 106B are each bridge welded, and the second sheet 106B and the third sheet 106C are bridge welded (step ST33). Specifically, the two second sheets 106B are stacked, the positioning pin hole 311 of each sheet 106B is disposed at the positioning pin 301, and the two second sheets 106B are disposed at a lower mold 302. Note that the lower mold 302 is provided with an electrode portion 302*a*, which is a projection constituting an electrode. In addition, the electrode portion 302*a* is formed in a shape that is abuttable against the region where the sheets 106B and 106C are welded, and an end surface of the electrode portion 302*a* used in this process is a projection formed in the shape of the bridge weld portion 101*b*.

Then, the bridge weld portion 101*b* is formed by bridge welding in a rectangular frame shape smaller than the outer peripheral edge shape of the air bags 101 using a high frequency welding machine, and the two second sheets 106B are integrally welded. In a similar manner, the two second sheets 106B and the second sheet 106B and the third sheet 106C are welded.

Note that one of the two sets of welded two second sheets 106B forms the eighth sheet member 106*b* of the first air bag 101 constituting the first outer layer 111 and the ninth sheet member 106*c* of the second air bag 101 constituting the first intermediate layer 112, the eighth sheet member and the ninth sheet member 106*c* face each other. And the other one of the two sets of welded two second sheets 106B forms the twelfth sheet member 106*f* of the third air bag 101 of the first intermediate layer 112 and the thirteenth sheet member 106*g* of the fourth air bag 101 of the second intermediate layer 113, the twelfth sheet member 106*f* and the thirteenth sheet member 106*g* face each other.

Additionally, the welded second sheet 106B and the third sheet 106C form the sixteenth sheet member 106*j* of the fifth air bag 101 of the second intermediate layer 113 and the seventeenth sheet member 106*k* of the sixth air bag 101 of the second outer layer 114, the sixteenth sheet member 106j and the seventeenth sheet member 106k face each other.

Next, the first outer layer 111 is formed (step ST34). Specifically, as illustrated in FIGS. 32 and 33, the positioning pin holes 311 of the two second sheets 106B bridge welded in step ST33 and the first sheet 106A are disposed at the positioning pins 301, and the bridge welded two second sheets 106B and the first sheet 106A are disposed in the lower mold 302. Note that the electrode portion 302a of the lower mold 302 used in this process is a projection with an end surface formed in the shape of the weld portion 101a.

At this time, as illustrated in FIG. 32, at least a portion of the second sheet 106B, which is disposed in the lower mold 302 side and facing a portion of the second sheet 106B and the first sheet 106A to be welded, escapes in a cavity 302b provided in the lower mold 302. Note that the lower mold 302 is provided with an electrode portion 302a, which is a projection constituting an electrode. Then, welding is performed on the outer peripheral edge shape of the air bags 101 using a high frequency welding machine to form the weld portion 101a. In this manner, the first outer layer 111 is formed.

Next, the second outer layer 114 is formed (step ST35). Specifically, as illustrated in FIG. 34, the positioning pin holes 311 of the second sheet 106B and the third sheet 106C bridge welded in step ST33 and the fourth sheet 106D welded with the connection portion 103 in step ST32 are disposed at the positioning pins 301, and the bridge welded second sheet 106B and the third sheet 106C as well as the fourth sheet 106D are disposed in the lower mold 302. Note that the electrode portion 302a of the lower mold 302 used in this process is a projection with an end surface formed in the shape of the weld portion 101a.

Also, at this time, as illustrated in FIG. 34, at least a portion of the second sheet 106B, facing a portion of the third sheet 106C and the fourth sheet 106D to be welded, escapes in the cavity 302b provided in the lower mold 302. Then, welding is performed on the outer peripheral edge shape of the air bags 101 using a high frequency welding machine to form the weld portion 101a. In this manner, the second outer layer 114 is formed.

Next, the target join portion 102 is formed on the second outer layer 114 that has been formed (step ST36). Specifically, as illustrated in FIG. 35, the positioning pin hole 311 of the second outer layer 114 is disposed at the positioning pin 301, and the second outer layer 114 formed at step ST35 is disposed in a press mold 401 with a shape that allows the outer peripheral edge shape of the sixth air bag 101, the target join portion 102, and the cutout portion 104 to be cut. Note that at this time, the second sheet 106B joined to the second outer layer 114 at the bridge weld portion 101b is disposed in the press mold 401 such that the second sheet 106B is not cut. Next, a contact plate is disposed on the upper surface of the second outer layer 114 and the press mold 401 and the contact plate are press-processed by a press processing machine. In this manner, the second outer layer 114 is cut in the outer peripheral edge shape of the sixth air bag 101, the target join portion 102, and the cutout portion 104, and the target join portion 102 is formed in the second outer layer 114.

Next, the first intermediate layer 112 and the second intermediate layer 113 are formed (step ST37). First, as illustrated in FIGS. 36 and 37, the positioning pin hole 311 of the two second sheets 106B, forming the twelfth sheet member 106f and the thirteenth sheet member 106g bridge welded in step ST33, and the positioning pin hole of an intermediate electrode 304 are disposed at the positioning pins 301 of an intermediate electrode setting jig 303, and the intermediate electrode 304 is set between the second sheet members 106B. The second sheet 106B, in which the intermediate electrode 304 is set, is detached from the intermediate electrode setting jig 303. Next, the second outer layer 114 with the second sheet 106B welded at the bridge weld portion 101b, the non-bridge welded two second sheets 106B, the two second sheets 106B set with the intermediate electrode 304, the non-bridge welded two second sheets 106B, and the first outer layer 111 with the second sheet 106B welded at the bridge weld portion 101b are sequentially stacked, and each positioning pin hole 311 is disposed at the positioning pins 301 of the lower mold 302. Note that the electrode portion 302a of the lower mold 302 used in this process is a projection with an end surface formed in the shape of the weld portion 101a. At this time, as illustrated in FIGS. 36 and 37, the outer peripheral edge of the air bag 101 of the second outer layer 114 and the target join portion 102 escape into the cavity 302b provided in the lower mold 302.

An upper mold 305 is disposed on the first sheet 106A of the first outer layer 111. The upper mold 305 is provided with an electrode portion 305a, which is a projection constituting an electrode. Note that the electrode portion 305a of the upper mold 305 used in this process is a projection with an end surface formed in the shape of the weld portion 101a.

In addition, the configuration may be such that the first outer layer 111 is disposed in the upper mold 305 in advance, and the upper mold 305 in which the first outer layer 111 is disposed is disposed on the second sheet 106B. At this time, as illustrated in FIG. 36, the outer peripheral edge of the air bag 101 of the first outer layer 111 escapes into a cavity 305b provided in the upper mold 305. Then, the four second sheets 106B between the lower mold 302 and the intermediate electrode 304 and the four second sheets 106B between the intermediate electrode 304 and the upper mold 305 are each welded in the outer peripheral edge shape of the air bags 101, and the weld portion 101a is formed. In this manner, the first intermediate layer 112 and the second intermediate layer 113 are formed. That is, the first outer layer 111, the first intermediate layer 112, the second intermediate layer 113, and the second outer layer 114, i.e. the six-layer air bags 101 are formed.

Next, the first outer layer 111, the first intermediate layer 112, and the second intermediate layer 113 that have been formed are finishing cut (step ST38). Specifically, as illustrated in FIGS. 38 and 39, the positioning pin hole 311 of the second outer layer 114 is disposed at the positioning pin of the press mold, the first to fifth air bags 101 are disposed, the contact plate is disposed on the upper surface of the first outer layer 111, and press processing using a press processing machine is performed. Thus, the outer peripheral edge shape of the first to fifth air bags 101 are cut. With these steps, the tensile cuff 74 is manufactured. Next, information such as a lot number is printed on a prescribed location on the tensile cuff 74 that has been manufactured (step ST39).

Next, as illustrated in FIG. 40, an example of a method for manufacturing the blood pressure measurement device 1 will be described.

First, the power feeding unit 8 is formed on the curler 5 (step ST41). The FPC constituting the wiring portion 8a and the power feeding terminal 8b is joined to the cover portion 5a and the recess 5c of the curler 5 by double-sided tape or the like and the cover 8c is joined to the recess 5c by double-sided tape of the like.

Next, the cuff structure 6 is joined to the curler 5 (step ST42). In a specific example, first, the back plate 72 is disposed in a jig for curving and heated in a heating furnace to heat treat the back plate 72 and curve it in a predetermined shape. Next, the joining layer 75, i.e., double-sided tape, is attached to a region of the fourth sheet member 86*d* of the pressing cuff 71 facing the curler 5 and the target join portion 82, and the pressing cuff 71 is attached to the curler 5. Then, double-sided tape is attached to the region of the sixth sheet member 96*b* of the sensing cuff 73 facing the back plate 72, and the sensing cuff 73 is attached to the back plate 72. Note that in these steps, the connection portion 84 of the pressing cuff 71 and the connection portion 93 of the sensing cuff 73 are inserted into the first hole portion 5*f*1 and the second hole portion 5*f*2 of the cover portion 5*a* of the curler 5.

Next, double-sided tape is attached to the region of the back plate 72 facing the pressing cuff 71, and the back plate 72 is attached to the first sheet member 86*a* of the pressing cuff 71. Then, double-sided tape is attached to the region of the eighteenth sheet member 106*l* of the tensile cuff 74 facing the curler 5 and the target join portion 102, and the tensile cuff 74 is attached to the curler 5 as well as the flow path body 83 of the pressing cuff 71 disposed on the inner surface of the curler 5 and the flow path body 92 of the sensing cuff 73. These steps join the cuff structure 6 to the curler 5.

Next, the sealing member 36 and the rear cover 35 are disposed on the cover portion 5*a* and the rear cover 35 is fixed to the cover portion 5*a* with the first joining members 35*a* (step ST43) to constitute a rear lid.

Then, the device body 3 is integrally assembled except for the rear cover 35 (step ST44). Next, the rear cover 35 is disposed on the end portion on the wrist 200 side of the outer case 31 of the device body 3, and the outer case 31 and the rear cover 35 are fixed with the second joining members 35*b* (step ST45). Then, the first belt 61 and the second belt 62 are assembled on the outer case 31 (step ST46). With these steps, the blood pressure measurement device 1 is manufactured.

Next, an example of measurement of a blood pressure value using the blood pressure measurement device 1 will be described using FIGS. 41 to 44. FIG. 41 is a flowchart illustrating an example of a blood pressure measurement using the blood pressure measurement device 1, illustrating both an operation of a user and an operation of the control unit 55. Additionally, FIGS. 42 to 44 illustrate an example of the user attaching the blood pressure measurement device 1 on the wrist 200.

First, the user attaches the blood pressure measurement device 1 to the wrist 200 (step ST51). As a specific example, for example, the user inserts one of the wrists 200 into the curler 5, as illustrated in FIG. 42.

At this time, in the blood pressure measurement device 1, the device body 3 and the sensing cuff 73 are disposed at opposite positions in the curler 5, and thus the sensing cuff 73 is disposed in a region on the hand palm-side of the wrist 200 in which the artery 210 resides. Thus, the device body 3 and the tensile cuff 74 are disposed on the hand back side of the wrist 200. Then, as illustrated in FIG. 43, the user passes the second belt 62 through the frame body 61*e* of the buckle 61*b* of the first belt 61 with the hand opposite to the hand on which the blood pressure measurement device 1 is disposed. The user then pulls the second belt 62 to bring the member on the inner circumferential surface side of the curler 5, that is, the cuff structure 6, into close contact with the wrist 200, and inserts the prong 61*f* into one of the small holes 62*a*. Thus, as illustrated in FIGS. 4 and 45, the first belt 61 and the second belt 62 are connected, and the blood pressure measurement device 1 is attached to the wrist 200.

Next, the user operates the operation unit 13 and inputs an instruction corresponding to the start of measurement of the blood pressure value. The operation unit 13, on which an input operation of the instruction has been performed, outputs an electrical signal corresponding to the start of the measurement to the control unit 55 (step ST52). The control unit 55 receives the electrical signal, and then for example, opens the first on-off valve 16A, the second on-off valve 16B, and the third on-off valve 16C, closes the fourth on-off valve 16D, and drives the pump 14 to supply compressed air to the pressing cuff 71, the sensing cuff 73, and the tensile cuff 74 through the first flow path 7*a*, the second flow path 7*b*, the third flow path 7*c*, and the fourth flow path 7*d* (step ST53). Thus, the pressing cuff 71, the sensing cuff 73, and the tensile cuff 74 start to be inflated.

The first pressure sensor 17A and the second pressure sensor 17B detect the pressures in the pressing cuff 71, the sensing cuff 73, and the tensile cuff 74, and output, to the control unit 55, electrical signals corresponding to the pressures (step ST54). On the basis of the received electrical signals, the control unit 55 determines whether the pressures in the internal spaces of the pressing cuff 71, the sensing cuff 73, and the tensile cuff 74 have reached a predetermined pressure for measurement of the blood pressure (step ST55). For example, in a case where the internal pressures of the pressing cuff 71 and the tensile cuff 74 have not reached the predetermined pressure and the internal pressure of the sensing cuff 73 has reached the predetermined pressure, the control unit 55 closes the first on-off valve 16A and supplies the compressed air through the second flow path 7*b*, the third flow path 7*c*, and the fourth flow path 7*d*.

When the internal pressures of the pressing cuff 71 and the tensile cuff 74 and the internal pressure of the sensing cuff 73 all have reached the predetermined pressure, the control unit 55 stops driving the pump 14 (YES in step ST55). At this time, as illustrated by the two-dot chain line in FIG. 4, the pressing cuff 71 and the tensile cuff 74 are sufficiently inflated, and the inflated pressing cuff 71 presses the back plate 72. Additionally, the tensile cuff 74 presses against the curler 5 in a direction away from the wrist 200, and then the belt 4, the curler 5, and the device body 3 move in a direction away from the wrist 200, and as a result, the pressing cuff 71, the back plate 72, and the sensing cuff 73 are pulled toward the wrist 200 side. In addition, when the belt 4, the curler 5, and the device body 3 move in a direction away from the wrist 200 due to the inflation of the tensile cuff 74, the belt 4 and the curler 5 move toward both lateral sides of the wrist 200, and the belt 4, the curler 5, and the device body 3 move in a state of close contact with both lateral sides of the wrist 200. Thus, the belt 4 and the curler 5, which are in close contact with the skin of the wrist 200, pull the skin on both lateral sides of the wrist 200 toward the hand back side. Note that the curler 5 may be configured to indirectly contact the skin of the wrist 200 with the sheet members 86 or 106 in between, for example, as long as the curler 5 can pull the skin of the wrist 200.

Furthermore, the sensing cuff 73 is inflated by being supplied with a predetermined amount of air such that the internal pressure equals the pressure required to measure blood pressure, and is pressed toward the wrist 200 by the back plate 72 that is pressed by the pressing cuff 71. Thus, the sensing cuff 73 presses the artery 210 in the wrist 200 and occludes the artery 210 as illustrated in FIG. 45.

Additionally, the control unit 55, for example, controls the third on-off valve 16C and repeats the opening and closing of the third on-off valve 16C, or adjusts the degree of opening of the third on-off valve 16C to pressurize a pressure of the internal space of the pressing cuff 71. In the process of pressurization, based on the electrical signal output by the second pressure sensor 17B, the control unit 55 obtains measurement results such as blood pressure values, for example, the systolic blood pressure and the diastolic blood pressure, and the heart rate and the like (step ST56). The control unit 55 outputs an image signal corresponding to the obtained measurement results to the display unit 12, and displays the measurement results on the display unit 12 (step ST57). In addition, after the end of the blood pressure measurement, the control unit 55 opens the first on-off valve 16A, the second on-off valve 16B, the third on-off valve 16C, and the fourth on-off valve 16D.

The display unit 12 receives the image signal, and then displays the measurement results on the screen. The user views the display unit 12 to confirm the measurement results. After the measurement is complete, the user removes the prong 61f from the small hole 62a, removes the second belt 62 from the frame body 61e, and pulls out the wrist 200 from the curler 5, thus detaching the blood pressure measurement device 1 from the wrist 200.

The blood pressure measurement device 1 according to an embodiment with such a configuration, in manufacturing the tensile cuff 74 including six-layer air bags 101, the second and third air bags 101, i.e., the first intermediate layer 112, and the fourth and fifth air bags 101, i.e., the second intermediate layer 113, are formed by welding the four sheet members 106 (second sheets 106B) all together. This allows the number of processes required for welding to form the air bags 101 of the tensile cuff 74 to be reduced.

Also, in such welding of the first intermediate layer 112 and the second intermediate layer 113, the four sheet members 106 each can be welded with a simple configuration in which the intermediate electrode 304 is disposed between the twelfth sheet member 106f (second sheet 106B) constituting the third air bag 101 and the thirteenth sheet member 106g (second sheet 106B) constituting the fourth air bag 101. Additionally, the first outer layer 111 and the second outer layer 114, which are not welded when the first intermediate layer 112 and the second intermediate layer 113 are welded, can escape into the cavities 302b and 305b of the lower mold 302 and the upper mold 305. Accordingly, the method for manufacturing the tensile cuff 74 is made to be easier manufacturing, and because the lower mold 302, the upper mold 305, and the intermediate electrode 304 can be used as an electrode for welding, the manufacturing device can be given a simpler configuration. Additionally, by using the lower mold 302, the upper mold 305, and the intermediate electrode 304, the first intermediate layer 112 and the second intermediate layer 113 can be welded at the same time, which further reduces the manufacturing processes.

Also, each of the opposing eighth sheet member 106b (second sheet 106B) of the first air bag 101 and the ninth sheet member 106c (second sheet 106B) of the second air bag 101, the opposing twelfth sheet member 106f (second sheet 106B) of the third air bag 101 and the thirteenth sheet member 106g (second sheet 106B) of the fourth air bag 101, and the sixteenth sheet member 106j (second sheet 106B) of the fifth air bag 101 and the seventeenth sheet member 106k (third sheet 106C) of the sixth air bag 101 are bridge welded together in advance. Thus, the air bags 101 can be easily formed without needing to weld together the formed air bags 101. Additionally, for bridge welding to weld together the sheet members 106 of adjacent air bags 101, only three section are welded in the stacking direction, allowing the processes for welding to join together the air bags 101 to be reduced.

With this method for manufacturing the tensile cuff 74, the manufacturing processes can be reduced, and manufacture is made easy. Additionally, in the first intermediate layer 112 and the second intermediate layer 113, because the second and third air bags 101 and the fourth and fifth air bags 101 are integrally constituted by the weld portion 101a constituting the outer peripheral edge of the air bags 101, even in a case of six-layer bag-like structures, the weld portion of the outer peripheral edge of the air bags 101 are four sections. That is, even in a configuration including six-layer air bags 101, the tensile cuff 74 has a four-layer structure constituted of the two outer layers 111 and 114 and the two intermediate layers 112 and 113. Thus, the second air bag 101 and the third air bag 101 as well as the fourth air bag 101 and the fifth air bag 101 are suppressed from deforming in the direction orthogonal to the stacking direction. As a result, with the tensile cuff 74, lateral bulging in the tensile cuff 74 can be prevented when the blood pressure measurement device 1 is attached on the wrist 200 and inflated.

Also, before the first intermediate layer 112 and the second intermediate layer 113 are formed, the first outer layer 111 and the second outer layer 114 are formed in advance. Then, in forming the first outer layer 111, the forming is performed such that a seventh sheet member 106a (first sheet 106A), which is separate, is welded to the eighth sheet member 106b (second sheet 106B) that is one of the two bridge-welded sheet members 106b and 106c. Thus, the ninth sheet member 106c of the two bridge-welded sheet members 106b and 106c, which is the other one not welded when the first outer layer 111 is formed, is only disposed in the cavity 302b of the lower mold 302 to escape from the electrode portion 302a. Thus, the first outer layer 111 can be easily formed.

In a similar manner, in forming the second outer layer 114, the forming is performed such that an eighteenth sheet member 106l (fourth sheet 106D), which is separate, is welded to the seventeenth sheet member 106k (third sheet 106C) that is one of the two bridge-welded sheet members 106j and 106k. Thus, the sixteenth sheet member 106j of the two bridge-welded sheet members 106j and 106k, which is the other one not welded when the second outer layer 114 is formed, is only disposed in the cavity 302b of the lower mold 302 to escape from the electrode portion 302a. This makes it easier to manufacture the second outer layer 114.

More specifically describing, in case where the first intermediate layer 112 and the second intermediate layer 113 are formed and subsequently the first outer layer 111 and the second outer layer 114 are formed, a portion, which is not welded in forming the first outer layer 111 and the second outer layer 114, needs to escape into the cavity 302b of the lower mold 302, and thus setting in the lower mold 302 is complicated. In contrast, forming the first outer layer 111 and the second outer layer 114 as in the present embodiment makes forming the tensile cuff 74 simple because only one sheet member 106 needs to escape.

As described above, according to a method for manufacturing the tensile cuff 74 used in the blood pressure measurement device 1 according to the present embodiment, lateral bulging of the tensile cuff 74 can be prevented and the manufacturing processes can be reduced.

Note that the present invention is not limited to the embodiments described above. In the examples described above, the tensile cuff 74 including six-layer air bags 101 and the method for manufacturing the tensile cuff 74 have been described. However, no such limitation is intended. In other words, the cuff may be formed from at least four air bags 101, with two of the air bags 101 being formed from at least four sheet members 106. In the case of such a configuration, the two adjacent air bags 101 can be formed by integrally welding the four sheet members 106. Thus, the welding processes can be reduced and deformation in the direction orthogonal to the stacking direction of the two adjacent air bags 101 can be suppressed.

In the example described above, a method for manufacturing a cuff for a blood pressure measurement device has been described using an example of manufacturing the tensile cuff 74. However, no such limitation is intended. For example, the pressing cuff 71 may be configured to be formed from four air bags 81 and be formed using the method for manufacturing described above.

That is, the present invention is not limited to the embodiments described above, and various modifications can be made in an implementation stage within a range that does not depart from the gist of the present invention. Furthermore, each of the embodiments may be implemented in combination as appropriate to the extent possible, and in this case, combined effects can be obtained. Also, the embodiments described above include various stages of invention, and various inventions may be extracted by appropriately combining the described plurality of disclosed constituent elements.

REFERENCE SIGNS LIST

1 Blood pressure measurement device
3 Device body
4 Belt
5 Curler
5*a* Cover portion
5*b* Escape portion
5*c* Recess
5*d* Insert member
5*e* Screw hole
5*f* Hole portion
5*f*1 First hole portion
5*f*2 Second hole portion
5*f*3 Third hole portion
6 Cuff structure
7 Fluid circuit
7*a* First flow path
7*b* Second flow path
7*c* Third flow path
7*d* Fourth flow path
8 Power feeding unit
8*a* Wiring portion
8*b* Power feeding terminal
8*c* Cover
11 Case
12 Display unit
13 Operation unit
14 Pump
15 Flow path portion
16 On-off valve
16A First on-off valve
16B Second on-off valve
16C Third on-off valve
16D Fourth on-off valve
17 Pressure sensor
17A First pressure sensor
17B Second pressure sensor
18 Power supply unit
19 Vibration motor
20 Control substrate
31 Outer case
31*a* Lug
31*b* Spring rod
32 Windshield
33 Base
35 Rear cover
35*a* First joining member
35*b* Second joining member
35*c* Hole portion
35*d* Hole portion
36 Sealing member
41 Button
42 Sensor
43 Touch panel
51 Substrate
52 Acceleration sensor
53 Communication unit
54 Storage unit
55 Control unit
56 Main CPU
57 Sub-CPU
61 First belt
61*a* Belt portion
61*b* Buckle
61*c* First hole portion
61*d* Second hole portion
61*e* Frame body
61*f* Prong
62 Second belt
62*a* Small hole
62*b* Third hole portion
71 pressing cuff
72 Back plate
72*a* Groove
73 Sensing cuff
74 Tensile cuff
75 Joining layer
81 Air bag (bag-like structure)
81*a* Weld portion
81*b* Bridge weld portion
82 Target join portion
83 Flow path body
83*a* Weld portion
84 Connection portion
86 Sheet member
86*a* First sheet member
86*b* Second sheet member
86*b*1 Opening
86*c* Third sheet member
86*c*1 Opening
86*d* Fourth sheet member
86*d*1 Hole portion
91 Air bag (bag-like structure)
91*a* Weld portion
91*b* Junction margin
92 Flow path body
92*a* Weld portion
93 Connection portion
96 Sheet member
96*a* Fifth sheet member
96*b* Sixth sheet member
96*b*1 Hole portion
101 Air bag (bag-like structure)
101*a* Weld portion
101*b* Bridge weld portion
102 Target join portion
102*a* Escape portion
103 Connection portion 104 Cutout portion
106 Sheet member
106A First sheet (sheet member)
106B Second sheet (sheet member)
106C Third sheet (sheet member)
106D Fourth sheet (sheet member)
106a Seventh sheet member
106b Eighth sheet member
106b1 Opening
106c Ninth sheet member
106c1 Opening
106d Tenth sheet member
106d1 Opening
106e Eleventh sheet member
106e1 Opening
106f Twelfth sheet member
106f1 Opening
106g Thirteenth sheet member
106g1 Opening
106h Fourteenth sheet member
106h1 Opening
106i Fifteenth sheet member
106i1 Opening
106j Sixteenth sheet member
106j1 Opening
106k Seventeenth sheet member
106k1 Opening
106l Eighteenth sheet member
106l1 Hole portion
111 First outer layer
112 First intermediate layer
113 Second intermediate layer
114 Second outer layer
200 Wrist
210 Artery
301 Positioning pin
302 Lower mold
302a Electrode portion
302b Cavity
303 Intermediate electrode setting jig
304 Intermediate electrode
305 Upper mold
305a Electrode portion
305b Cavity
311 Positioning pin hole
401 Press mold

The invention claimed is:

1. A method for manufacturing a cuff for a blood pressure measurement device, the cuff comprising:
a first outer layer including a first bag-like structure having a first bag shape, the first bag-like structure comprising a first sheet member and a second sheet member having a first inflatable space therebetween;
a first intermediate layer having a second bag shape and stacked on the first outer layer, the first intermediate layer including a second bag-like structure and a third bag-like structure, the second bag-like structure comprising a third sheet member and a fourth sheet member having a second inflatable space therebetween, and the third bag-like structure comprising a fifth sheet member and a sixth sheet member having a third inflatable space therebetween;
a second intermediate layer having a third bag shape and stacked on the first intermediate layer, the second intermediate layer including a fourth bag-like structure and a fifth bag-like structure, the fourth bag-like structure comprising a seventh sheet member and an eighth sheet member having a fourth inflatable space therebetween, and the fifth bag-like structure comprising a ninth sheet member and a tenth sheet member having a fifth inflatable space therebetween; and
a second outer layer having a fourth bag shape and stacked on the second intermediate layer, the second outer layer including a sixth bag-like structure comprising an eleventh sheet member and a twelfth sheet member having an inflatable sheet therebetween, the method of manufacturing the cuff comprising:
welding together outer peripheral edges of the first and second sheet members to form the first outer layer and welding together outer peripheral edges of eleventh and twelfth sheet members to form the second outer layer;
bridge welding together inside from outer peripheral edges of each of the sheet members:
the second sheet member to the third sheet member to form a first bridge weld therebetween,
the sixth sheet member to the seventh sheet member to form a second bridge weld therebetween, and
the tenth sheet member to the eleventh sheet member to form a third bridge weld therebetween;
disposing the fourth sheet member and the fifth sheet member between the third sheet member bridge welded with the second sheet member and between the sixth sheet member bridge welded with the seventh sheet member;
disposing the eighth sheet member and the ninth sheet member between the seventh sheet member bridge welded with the sixth sheet member and between the tenth sheet member bridge welded with the eleventh sheet member; and
welding together the outer peripheral edges of the third, fourth, fifth, and sixth sheet members to form the first intermediate layer and welding together the outer peripheral edges of the seventh, eighth, ninth, and tenth sheet members to form the second intermediate layer,
wherein first, second, and third bridge welds surround openings formed in each of the sheet members forming the bridge welds.

2. The method for manufacturing the cuff for the blood pressure measurement device according to claim 1, wherein welding to form the first and second intermediate layers further comprises:
disposing an intermediate electrode having a plate-like shape between the sixth sheet member and the seventh sheet;
disposing the sheet members of the first intermediate layer and the sheet member of the second intermediate layer between a lower mold and an upper mold; and
welding to form the first intermediate layer and the second intermediate layer using the lower mold, the intermediate electrode, and the upper mold.

3. The method for manufacturing the cuff for the blood pressure measurement device according to claim 2, further comprising:
welding the first intermediate layer and the second intermediate layer at the same time.

4. The method for manufacturing a cuff for a blood pressure measurement device according to claim 2,
wherein welding the first intermediate layer and the second intermediate layer with the lower mold, the intermediate electrode, and the upper mold occurs after the first outer layer and the second outer layer are formed.

5. A method for manufacturing a cuff for a blood pressure measurement device, comprising:

disposing a first sheet member and a second sheet member for forming a first bag-like structure, the first bag-like structure having a first inflatable space between the first sheet member and the second sheet member;

welding together the first and second sheet members at their outer peripheral edges to form the first bag-like structure in a first bag shape with a first peripheral weld;

disposing a third sheet member and a fourth sheet member for forming a second bag-like structure, the second bag-like structure having a second inflatable space between the third sheet member and the fourth sheet member;

disposing a fifth sheet member and a sixth sheet member for forming a third bag-like structure, the third bag-like structure having a third inflatable space between the fifth sheet member and the sixth sheet member;

welding together the third sheet member, the fourth sheet member, the fifth sheet member and the sixth sheet member at their outer peripheral edges to form the second bag-like structure and the third bag-like structure as a unitary structure in a second bag shape with a second peripheral weld, the unitary structure having the third sheet member and the sixth sheet member as outer layers;

stacking the first bag-like structure on the unitary structure; and bridge welding inside from the outer peripheral edges of the second sheet member and the third sheet member, to form a bridge weld between the second sheet member in the first bag-like structure and the third sheet member in the unitary structure;

wherein openings are formed in a portion of the second and third sheet members, and the bridge weld surrounds the openings.

\* \* \* \* \*